United States Patent
Iwai et al.

(10) Patent No.: US 9,134,109 B2
(45) Date of Patent: *Sep. 15, 2015

(54) PHASE IMAGE ACQUISITION DEVICE

(75) Inventors: Hidenao Iwai, Hamamatsu (JP);
Masatoshi Fujimoto, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 163 days.

This patent is subject to a terminal disclaimer.

(21) Appl. No.: 13/695,330

(22) PCT Filed: May 2, 2011

(86) PCT No.: PCT/JP2011/060562
§ 371 (c)(1),
(2), (4) Date: Dec. 17, 2012

(87) PCT Pub. No.: WO2011/136382
PCT Pub. Date: Nov. 3, 2011

(65) Prior Publication Data
US 2013/0094027 A1   Apr. 18, 2013

(30) Foreign Application Priority Data
Apr. 30, 2010 (JP) ................. 2010-105671

(51) Int. Cl.
*G01B 9/02* (2006.01)
*G01N 21/41* (2006.01)
(Continued)

(52) U.S. Cl.
CPC ............ *G01B 9/02045* (2013.01); *G01N 21/41* (2013.01); *G02B 21/14* (2013.01);
(Continued)

(58) Field of Classification Search
CPC ........... G01B 9/02045; G01B 9/02084; G01N 21/41; G02B 21/14; G02B 27/52; G03H 1/0443; G03H 2001/0447; G03H 2001/045; G03H 2001/0471; G03H 2210/62
USPC .......... 356/450, 457, 458, 484, 486; 359/370, 359/371
See application file for complete search history.

(56) References Cited

U.S. PATENT DOCUMENTS

| 5,501,226 A | 3/1996 | Petersen et al. |
| 5,549,114 A | 8/1996 | Petersen et al. |

(Continued)

FOREIGN PATENT DOCUMENTS

| CN | 1135043 | 11/1996 |
| CN | 1542411 | 11/2004 |

(Continued)

OTHER PUBLICATIONS

F. LE Clerc et al., "Numerical heterodyne holography with two-dimensional photodetector arrays", OPTICS LETTER, May 15, 2000, pp. 716-718, vol. 25, No. 10.

(Continued)

*Primary Examiner* — Michael A Lyons
(74) *Attorney, Agent, or Firm* — Drinker Biddle & Reath LLP

(57) ABSTRACT

Provided is an observation device which can obtain a phase image of a moving object rapidly with high sensitivity even when using a photodetector having a slow read-out speed per pixel. The observation device 1 comprises a light source 10, a first modulator 20, a second modulator 30, a lens 40, a beam splitter 41, a photodetector 46, and an arithmetic unit 50. The lens 40 receives scattered light generated by a moving object 2 and forms a Fourier transform image of the object 2. The photodetector 46 outputs data representing a sum in a v direction of data temporally changing at a frequency corresponding to a Doppler shift frequency of the light having reached each position on a light-receiving surface through the lens 40 at each position in a u direction at each time. The arithmetic unit 50 obtains an image of the object 2 according to the output of the photodetector 46.

28 Claims, 63 Drawing Sheets

(51) Int. Cl.
*G02B 21/14* (2006.01)
*G02B 27/52* (2006.01)
*G03H 1/04* (2006.01)
*G03H 1/08* (2006.01)

(52) U.S. Cl.
CPC .............. *G02B 27/52* (2013.01); *G03H 1/0443* (2013.01); *G03H 1/0866* (2013.01); *G03H 2001/045* (2013.01); *G03H 2001/0447* (2013.01); *G03H 2001/0463* (2013.01); *G03H 2210/62* (2013.01)

(56) References Cited

U.S. PATENT DOCUMENTS

| | | | |
|---|---|---|---|
| 5,684,588 A * | 11/1997 | Khoury et al. ................ | 356/458 |
| 6,246,495 B1 | 6/2001 | Yamaguchi | |
| 6,330,086 B1 * | 12/2001 | Collot et al. .................... | 359/9 |
| 6,485,413 B1 | 11/2002 | Boppart et al. | |
| 7,405,834 B1 | 7/2008 | Marron et al. | |
| 2005/0046857 A1 * | 3/2005 | Bingham et al. ............. | 356/457 |
| 2008/0049231 A1 | 2/2008 | Bachalo et al. | |
| 2008/0144041 A1 * | 6/2008 | Muenter ...................... | 356/484 |
| 2009/0086191 A1 | 4/2009 | Bristol | |
| 2010/0317975 A1 | 12/2010 | Yelin et al. | |
| 2013/0063729 A1 * | 3/2013 | Iwai et al. .................... | 356/486 |

FOREIGN PATENT DOCUMENTS

| | | |
|---|---|---|
| JP | 8-206086 A | 8/1996 |
| JP | 2003-527577 A | 9/2003 |
| JP | 3471556 B2 | 12/2003 |
| JP | 2004-105708 | 4/2004 |
| JP | 2007-504444 | 3/2007 |
| JP | 2007-508540 | 4/2007 |
| WO | WO 98/52021 | 11/1998 |
| WO | WO 01/36901 | 5/2001 |

OTHER PUBLICATIONS

Gabriel Popescu et al., "Fourier phase microscopy for investigation of biological structures and dynamics", OPTICS LETTERS, Nov. 1, 2004, pp. 2503-2505, vol. 29, No. 21.

Gabriel Popescu et al., "Diffraction phase microscopy for quantifying cell structure and dynamics", OPTICS LETTERS, Mar. 15, 2006, pp. 775-777, vol. 31, No. 6.

Yoshiaki Sasaki et al., "Fundamental Imaging Properties of Transillumination Laser CT Using Optical Fiber Applicable to Bio-Medical Sensing", IEEE SENSORS JOURNAL, Oct. 2003, pp. 658-667, vol. 3. No. 5.

U.S. Office Action dated Aug. 8, 2014 that issued in U.S. Appl. No. 13/695,344 including Double Patenting Rejections on pp. 5-8.

* cited by examiner

Fig.18
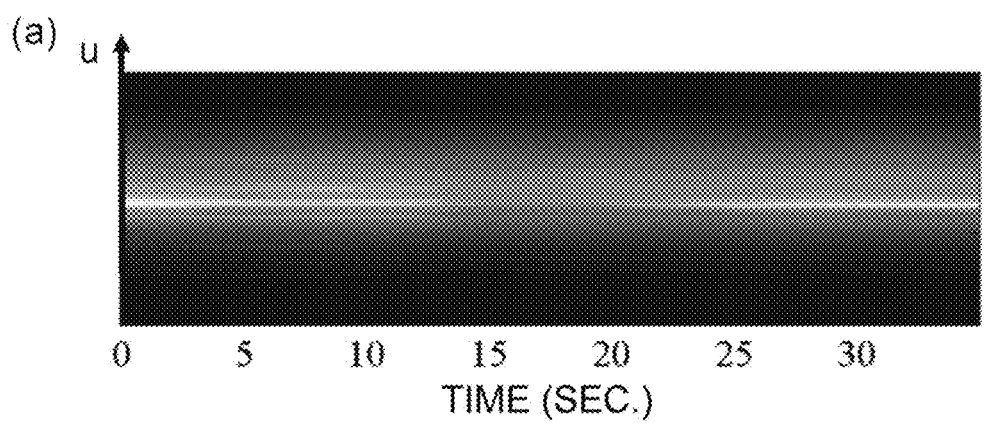
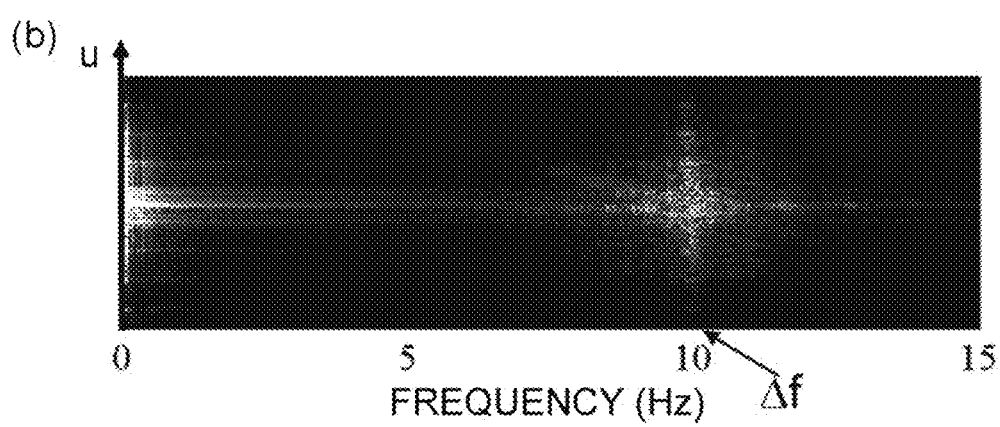
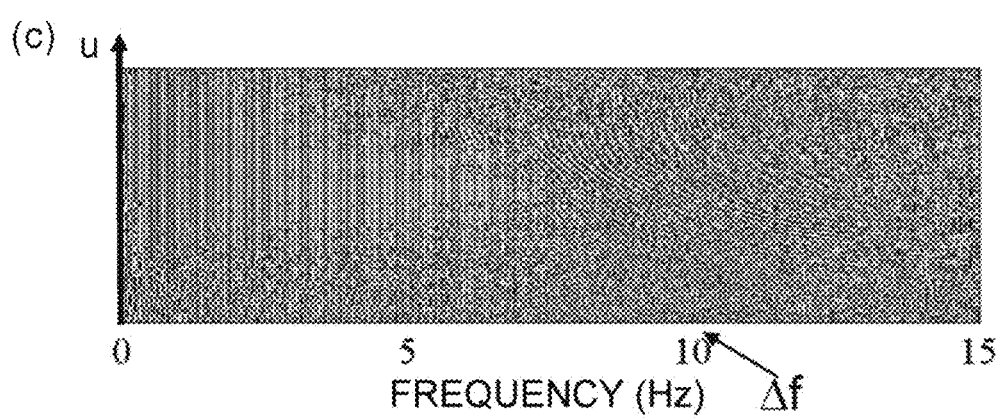

Fig.19
(a)
(b)
(c)
(d)
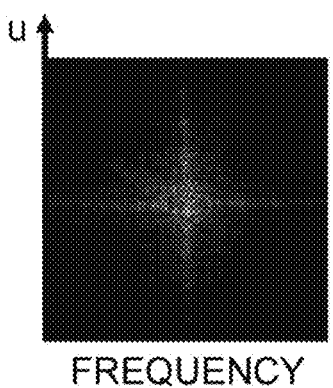
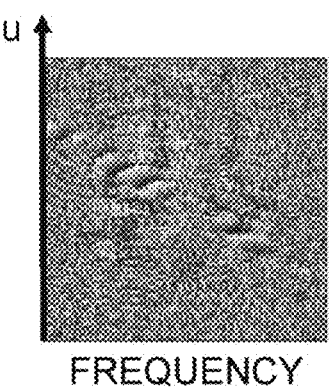
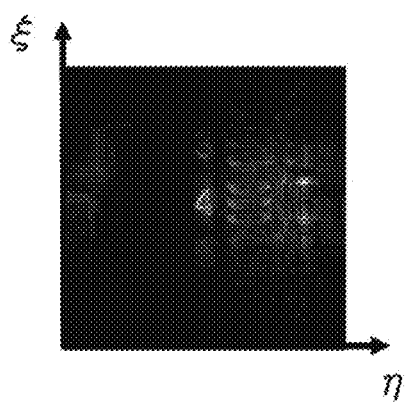
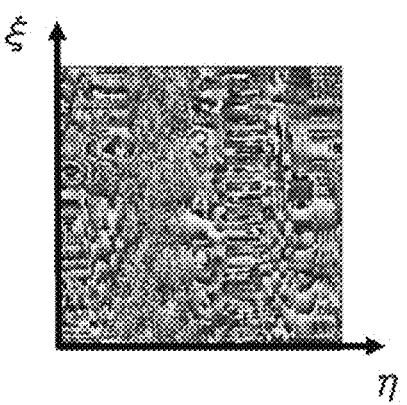

PHASE IMAGE ACQUISITION DEVICE

TECHNICAL FIELD

The present invention relates to an observation device for observing a phase image of an object.

BACKGROUND ART

Colorless, transparent objects (phase objects) such as cells and glass bodies, which are hard to observe according to an intensity distribution (amplitude image) of transmitted light occurring when the objects are irradiated with light, are observed according to a phase distribution (phase image) of the transmitted light. Examples of devices for observing the phase image of such an object include phase contrast microscopes and differential interference microscopes. However, these devices cannot obtain quantitative information about the optical thickness of the objects.

As techniques for obtaining quantitative information by observing a phase image of an object, those using phase shift methods described in Patent Literature 1 and Non Patent Literature 1 have been known. In observation devices based on these phase shift methods, light having a wavelength $\lambda$ emitted from a light source is split in two, one split light is transmitted through the object so as to become object light, the other split light is used as reference light, and a two-dimensional image formed by interference between the object light and reference light is captured. While changing the optical path length of the reference light in increments of $\lambda/4$, four two-dimensional images are obtained, which are then subjected to a predetermined arithmetic operation, so as to yield amplitude and phase images of the object.

CITATION LIST

Patent Literature

Patent Literature 1: Japanese Patent Publication No. 3471556

Non Patent Literature

Non Patent Literature 1: F. Le Clerc, et al, "Numerical heterodyne holography with two-dimensional photodetector arrays," Optics Letters, Vol. 25, No. 10, pp. 716-718, (2000).

SUMMARY OF INVENTION

Technical Problem

In the observation devices using the phase shift methods described in Patent Literature 1 and Non Patent Literature 1, it is necessary for the object to stand still while obtaining four two-dimensional images. For obtaining a phase image of a moving object, it is necessary to obtain four two-dimensional images in a period during which the object can be presumed to stand still by using a two-dimensional photodetector array having such a high frame rate as to enable high-speed imaging. However, the photodetector capable of high-speed imaging is expensive or has such a small number of pixels that it is poor in spatial resolution. Its exposure time, even at the longest, falls within a period during which the object can be presumed to stand still, so that the image quality is poor also in terms of SN ratio, and the sensitivity is low.

For solving the problems mentioned above, it is an object of the present invention to provide an observation device which can obtain a phase image of a moving object even when using a two-dimensional photodetector array having a slow read-out speed per pixel. For example, it is an object to provide an observation device which can obtain a phase image of an object moving rapidly at a speed which is n times that of a two-dimensional detector having m×n pixels in vertical and horizontal directions, become effective in multiple exposure of the object moving within a field of view, improve the SN ratio, and enhance the sensitivity.

Solution to Problem

The observation device in accordance with one aspect of the present invention comprises (1) a light source for irradiating a moving object with light; (2) a detection unit, letting a first direction be a direction on a predetermined plane yielding a fixed Doppler shift effect caused by a movement of the object in light having reached the predetermined plane in scattered light generated by the object upon irradiation with the light by the light source while being perpendicular to a moving direction of the object and a second direction be a direction orthogonal to the first direction on the predetermined plane while being parallel to the moving direction of the object, for outputting data representing a sum in the second direction of data temporally changing at a frequency corresponding to a Doppler shift frequency of the light having reached each position on the predetermined plane at each position in the first direction at each time; and (3) an arithmetic unit for performing a one-dimensional Fourier transform with respect to a time variable of data employing the position in the first direction on the predetermined plane and time as variables and a two-dimensional Fourier transform of the Fourier-transformed data, so as to yield data obtained by the two-dimensional Fourier transform as an image of the object. Here, the first direction is a direction perpendicular to a moving direction of the object, while the second direction is a direction parallel to the moving direction of the object.

In the observation device in accordance of the present invention, the moving object is irradiated with light by the light source, so as to generate scattered light. The scattered light incurs a Doppler shift by an amount corresponding to the scattering direction. The scattered light is received by the detection unit. In the light having reached a predetermined plane, a direction yielding a fixed Doppler shift effect caused by the movement of the object is defined as the first direction, and a direction orthogonal to the first direction on the predetermined plane is defined as the second direction. Data representing a sum in the second direction of data temporally changing at a frequency corresponding to a Doppler shift frequency of the light having reached each position on the predetermined plane through an optical system is issued at each time from the detection unit at each position in the first direction. The arithmetic unit performs a Fourier transform with respect to a time variable of data employing the position in the first direction and time as variables and a two-dimensional Fourier transform of the Fourier-transformed data, whereby data obtained by the two-dimensional Fourier transform is yielded as an image of the object.

The detection unit includes (a) an optical system for receiving a light emitted from the light source and splitting thus received light in two behind of the object so as to yield first light and second light, modulating the second light with a modulator, and then causing a heterodyne interference between the first light and the modulated second light on the predetermined plane; and (b) a photodetector having a light-receiving surface on the predetermined plane and a pixel array structure in the first direction on the light-receiving surface.

The arithmetic unit may comprise a first Fourier transform device for performing a one-dimensional Fourier transform with respect to the time variable and a second Fourier transform unit for performing the two-dimensional Fourier transform, while the second Fourier transform unit may comprise a third Fourier transform device for performing a one-dimensional Fourier transform with respect to a temporal frequency and a fourth Fourier transform device for performing a one-dimensional Fourier transform with respect to the first direction.

The observation device in accordance with the present invention may further comprise a lens arranged between the light source and the detection unit, the light-receiving surface of the detection unit being arranged on a back focal plane in the first direction of the lens and serving as a back focal plane in the second direction of the lens, while the light source, lens, detection unit, first Fourier transform device, third Fourier transform device, and fourth Fourier transform device are arranged in sequence.

The observation device in accordance with the present invention may further comprise a lens arranged between the light source and the detection unit, the light-receiving surface of the detection unit being arranged on a plane where a Fraunhofer diffraction image of the object is formed by the lens in the first direction and serving as a plane where a Fraunhofer diffraction image of the object is formed in the second direction, while the light source, lens, detection unit, first Fourier transform device, third Fourier transform device, and fourth Fourier transform device are arranged in sequence.

The observation device in accordance with the present invention may further comprise a lens arranged between the light source and the detection unit, the light-receiving surface of the detection unit being arranged on a plane where a Fraunhofer diffraction image of the object is formed by the lens in the first direction and serving as a plane where an image of the object is formed in the second direction, while the light source, lens, detection unit, first Fourier transform device, third Fourier transform device, and fourth Fourier transform device are arranged in sequence.

The observation device in accordance with the present invention may further comprise a lens arranged between the light source and the detection unit, the light-receiving surface of the detection unit being arranged on a plane where a Fraunhofer diffraction image of the object is formed by the lens in the first direction and serving as a plane where a Fresnel diffraction image of the object is formed in the second direction, while the light source, lens, detection unit, first Fourier transform device, third Fourier transform device, and fourth Fourier transform device are arranged in sequence.

The observation device in accordance with the present invention may further comprise a lens arranged between the light source and the detection unit, the light-receiving surface of the detection unit being arranged on a plane where an image of the object is formed by the lens in the first direction and serving as a plane where a Fraunhofer diffraction image of the object is formed in the second direction, while the light source, lens, detection unit, first Fourier transform device, fourth Fourier transform device, third Fourier transform device, and fourth Fourier transform device are arranged in sequence, the lens performing a one-dimensional Fourier transform with respect to the first direction.

The observation device in accordance with the present invention may further comprise a lens arranged between the light source and the detection unit, the light-receiving surface of the detection unit being arranged on a plane where an image of the object is formed by the lens in the first direction and serving as a plane where an image of the object is formed in the second direction, while the light source, lens, detection unit, first Fourier transform device, fourth Fourier transform device, third Fourier transform device, and fourth Fourier transform device are arranged in sequence, the lens performing a one-dimensional Fourier transform with respect to the first direction.

The observation device in accordance with the present invention may further comprise a lens arranged between the light source and the detection unit, the light-receiving surface of the detection unit being arranged on a plane where an image of the object is formed by the lens in the first direction and serving as a plane where a Fresnel diffraction image of the object is formed in the second direction, while the light source, lens, detection unit, first Fourier transform device, fourth Fourier transform device, third Fourier transform device, and fourth Fourier transform device are arranged in sequence, the lens performing a one-dimensional Fourier transform with respect to the first direction.

The observation device in accordance with the present invention may further comprise a lens arranged between the light source and the detection unit, the light-receiving surface of the detection unit being arranged on a plane where a Fresnel diffraction image of the object is formed by the lens in the first direction and serving as a plane where a Fraunhofer diffraction image of the object is formed in the second direction, while the light source, lens, detection unit, first Fourier transform device, third Fourier transform device, fourth Fourier transform device, and fourth Fourier transform device are arranged in sequence.

The observation device in accordance with the present invention may further comprise a lens arranged between the light source and the detection unit, the light-receiving surface of the detection unit being arranged on a plane where a Fresnel diffraction image of the object is formed by the lens in the first direction and serving as a plane where an image of the object is formed in the second direction, while the light source, lens, detection unit, first Fourier transform device, third Fourier transform device, fourth Fourier transform device, and fourth Fourier transform device are arranged in sequence.

The observation device in accordance with the present invention may further comprise a lens arranged between the light source and the detection unit, the light-receiving surface of the detection unit being arranged on a plane where a Fresnel diffraction image of the object is formed by the lens in the first direction and serving as a plane where a Fresnel diffraction image of the object is formed in the second direction, while the light source, lens, detection unit, first Fourier transform device, third Fourier transform device, fourth Fourier transform device, and fourth Fourier transform device are arranged in sequence.

The observation device in accordance with the present invention may further comprise a lens arranged between the light source and the detection unit, the light-receiving surface of the detection unit being arranged on a plane where a Fresnel diffraction image of the object is formed by the lens in the first direction and serving as a plane where a Fresnel diffraction image of the object is formed in the second direction, while the light source, lens, detection unit, first Fourier transform device, fourth Fourier transform device, third Fourier transform device, and fourth Fourier transform device are arranged in sequence.

The observation device in accordance with another aspect of the present invention comprises a light source for irradiating a moving object with light; a detection unit, letting a first direction be a direction on a predetermined plane yielding a fixed Doppler shift effect caused by a movement of the object in light having reached the predetermined plane in scattered light generated by the object upon irradiation with the light by the light source while being perpendicular to a moving direction of the object and a second direction be a direction orthogonal to the first direction on the predetermined plane while being parallel to the moving direction of the object, for outputting data representing a sum in the second direction of data temporally changing at a frequency corresponding to a Doppler shift frequency of the light having reached each position on the predetermined plane at each position in the first direction at each time; and an arithmetic unit for performing, for data employing a position in the first direction on the predetermined plane and time as variables, a one-dimensional Fourier transform with respect to a time variable, a one-dimensional Fourier transform with respect to the temporal frequency, and a one-dimensional Fourier transform with respect to the first direction, so as to yield data obtained by the one-dimensional Fourier transforms as an image of the object; wherein the detection unit includes an optical system for receiving a light emitted from the light source and splitting thus received light in two behind of the object so as to yield first light and second light, modulating the second light with a modulator, and then causing a heterodyne interference between the first light and the modulated second light on the predetermined plane; and a photodetector having a light receiving surface on the predetermined plane and a pixel array structure in the first direction on the light-receiving surface.

The observation device in accordance with the present invention may further comprise a lens arranged between the light source and the detection unit, the light-receiving surface of the detection unit being arranged on a plane where an image of the object is formed by the lens in the first direction and serving as a plane where an image of the object is formed in the second direction, while the light source, lens, detection unit, first Fourier transform device, and third Fourier transform device are arranged in sequence, the lens including an action to perform a one-dimensional Fourier transform of the diffracted light from the object 2 with respect to the first direction.

The observation device in accordance with the present invention may further comprise a lens arranged between the light source and the detection unit, the light-receiving surface of the detection unit being arranged on a plane where an image of the object is formed by the lens in the first direction and serving as a plane where a Fraunhofer diffraction image of the object is formed in the second direction, while the light source, lens, detection unit, first Fourier transform device, and third Fourier transform device are arranged in sequence, the lens including an action to perform a one-dimensional Fourier transform of the diffracted light from the object 2 with respect to the first direction.

The observation device in accordance with the present invention may further comprise a lens arranged between the light source and the detection unit, the light-receiving surface of the detection unit being arranged on a plane where an image of the object is formed by the lens in the first direction and serving as a plane where a Fresnel diffraction image of the object is formed in the second direction, while the light source, lens, detection unit, first Fourier transform device, and third Fourier transform device are arranged in sequence, the lens including an action to perform a one-dimensional Fourier transform of the diffracted light from the object 2 with respect to the first direction.

In the observation device in accordance with the present invention, the arithmetic unit may further comprise an initial phase correction device for correcting an initial phase included in the data obtained by the one-dimensional Fourier transform with respect to the time variable.

The observation device in accordance with the present invention may include a plurality of detection units, the arithmetic unit further comprising a summing device for yielding a sum of outputs from the plurality of detection units.

The observation device in accordance with the present invention may further comprise a converter for performing a Fourier transform or Fresnel transform with respect to the second direction.

The arithmetic unit may perform a two-dimensional Fourier transform of data in a region including a range of a Nyquist frequency in upper and lower region of a difference frequency between first and second modulation frequencies in the data obtained by the one-dimensional Fourier transform with respect to the time variable.

The arithmetic unit may perform a one-dimensional Fourier transform with respect to the frequency and a one-dimensional Fourier transform with respect to the first direction of data in a region including a range of a Nyquist frequency in upper and lower region of a difference frequency between first and second modulation frequencies in the data obtained by the one-dimensional Fourier transform with respect to the time variable.

The observation device in accordance with the present invention may further comprise a speed detector for detecting a moving speed of the object. In this case, during the one-dimensional Fourier transform with respect to the time variable or the two-dimensional Fourier transform, the arithmetic unit corrects a change in the speed of the object according to the speed of the object detected by the speed detector.

In the observation device in accordance with the present invention, the irradiation of the object with the light may be performed in an optical arrangement of transmitted illumination or reflected illumination. In the observation device in accordance with the present invention, the light source may be a light source for generating light in a single longitudinal mode or a light source for generating broadband light, and may be a mode-locked laser in the latter case.

Advantageous Effects of Invention

The present invention can obtain a phase image of a moving object even when using a photodetector having a slow read-out speed per pixel. For example, a phase image of a moving object can be obtained rapidly at a speed which is n times that of a two-dimensional detector having m×n pixels in vertical and horizontal directions. It can also be effective in performing multiple exposure of the object moving within a field of view, thereby improving the SN ratio and enhancing the sensitivity.

BRIEF DESCRIPTION OF DRAWINGS

FIG. 18 is a diagram illustrating data obtained by the first example;

FIG. 19 is a data obtained by the first example;

DESCRIPTION OF EMBODIMENTS

Figure 1:
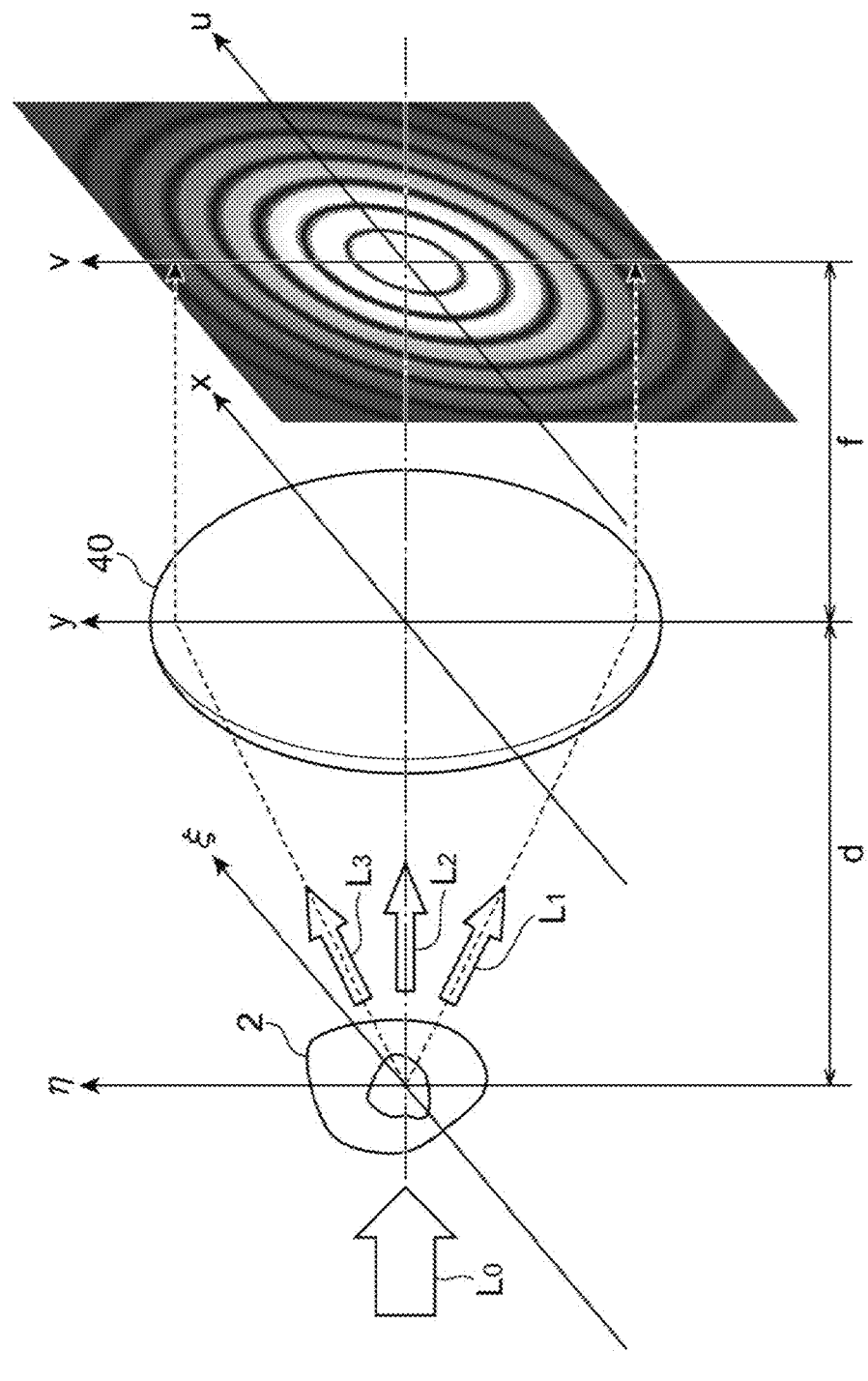
FIG. 1 is a diagram for explaining a principle of acquiring a phase image of an object by the observation device in accordance with an embodiment.

In the following, modes for carrying out the present invention will be explained in detail with reference to the accompanying drawings. In the drawings, the same constituents will be referred to with the same signs while omitting their overlapping descriptions.

The observation device in accordance with an embodiment utilizes a Doppler shift effect generated when a moving object is irradiated with light, a fixed relationship between an diffraction direction of scattered light generated by the object and the Doppler shift frequency in particular, so as to acquire a phase image of the object. First, fundamental matters concerning the acquisition of the phase image of the object by the observation device in accordance with this embodiment will be explained with reference to FIGS. 1 to 7.

FIG. 1 is a diagram for explaining a principle of acquiring a phase image of an object by the observation device in accordance with this embodiment. This diagram illustrates $\xi\eta$, xy, and uv coordinate systems. Each of the $\xi$, $\eta$, x, y, u, and v axes is perpendicular to the optical axis of a lens 40. The $\xi$, x, and u axes are parallel to each other. The $\eta$, y, and v axes are parallel to each other. An object 2 to be observed exists on the $\xi\eta$ plane. The lens 40 exists on the xy plane. The back focal plane of the lens 40 coincides with the uv plane. The distance between the $\xi\eta$ and xy planes is d. The distance between the xy and uv planes coincides with the focal length f of the lens 40.

The object 2 is assumed to move in the $-\eta$ direction on the $\xi\eta$ plane. Suppose that the object 2 is irradiated with light $L_0$ advancing in a direction $\zeta$ perpendicular to the $\xi\eta$ plane. An example of the light $L_0$ is a plane wave. Scattered light beams $L_1$ to $L_3$ generated by the object 2 upon irradiation with the light $L_0$ advance in various directions and incur a Doppler shift as the object 2 moves. The scattered light $L_1$ having a scattering direction vector component in the same direction as the moving direction of the object 2 rises in its optical frequency. The scattered light $L_2$ having no scattering direction vector component in the moving direction of the object 2 does not change in its optical frequency. The scattered light $L_3$ having a scattering direction vector component in a direction opposite from the moving direction of the object 2 decreases in its optical frequency. These scattered light beams $L_1$ to $L_3$ reach the uv plane through the lens 40.

Figure 2:
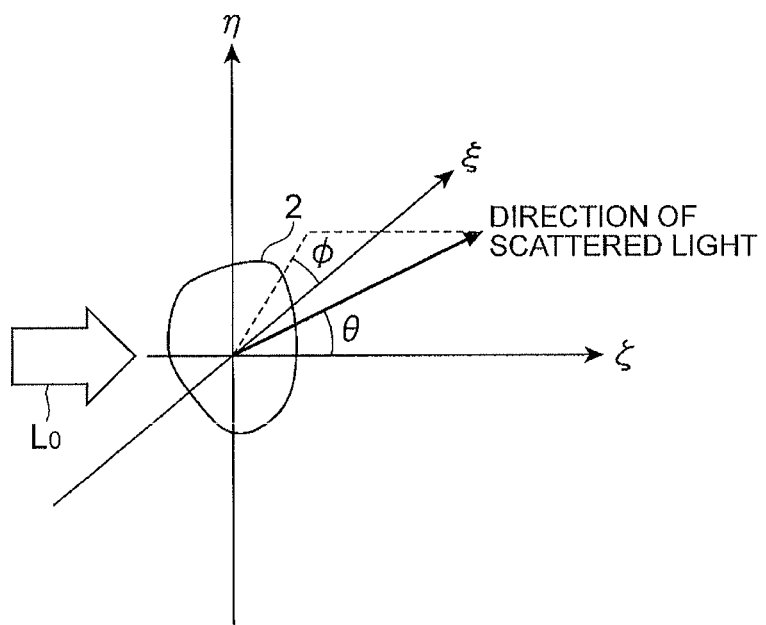
FIG. 2 is a diagram for explaining a scattering direction of scattered light generated by the object.

FIG. 2 is a diagram for explaining a scattering direction of scattered light generated by the object. For expressing the scattering direction of the scattered light generated by the object 2, it must be described by two variables, i.e., elevation angle $\theta$ and azimuth $\phi$. A point source of light assumed to be arranged within the object 2 is defined as the origin of the $\xi\eta\zeta$ coordinate system. The angle formed between the direction vector of the scattered light from the point source located at the origin and the $\zeta$ axis is defused as the elevation angle $\theta$. The angle formed between a projected vector of the scattering direction vector on the $\xi\eta$ plane and the $\xi$ axis is defined as the azimuth $\phi$.

Figure 3:
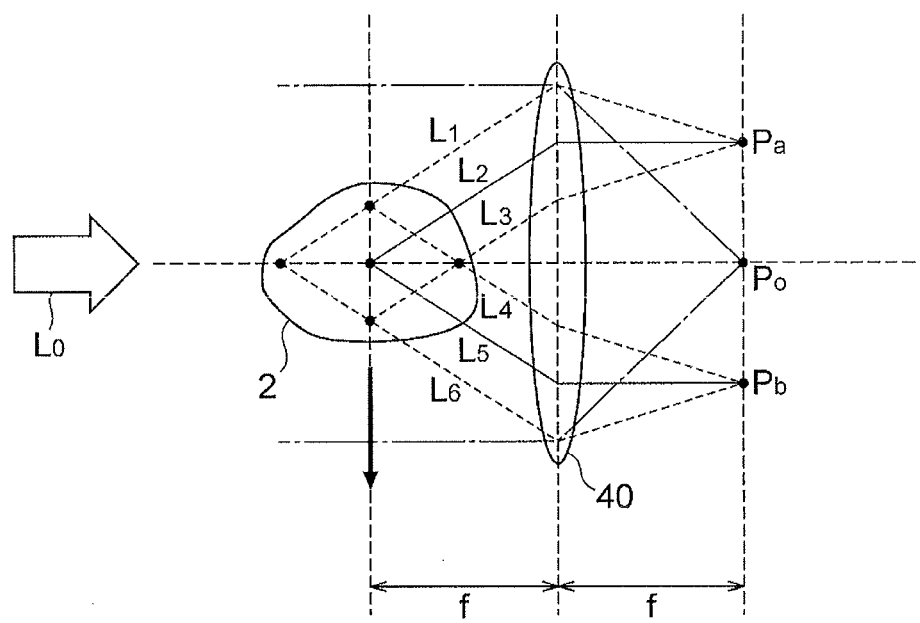
FIG. 3 is a diagram for explaining positions at which the scattered light generated by the object reaches a back focal plane of a lens.

FIG. 3 is a diagram for explaining positions at which the scattered light generated by the object reaches the back focal plane of the lens. The scattered light generated when the object 2 is irradiated with the light $L_0$ can be regarded as the secondary wave emitted from a point source assumed to be arranged within the object 2 according to Huygens' principle. In this diagram, five virtual point sources are arranged within the object 2. These point sources may exist not only on the front focal plane of the lens 40 but also in front and rear thereof.

Scattered light beams $L_1$ to $L_3$ having a fixed set of elevation angle $\theta$ and azimuth $\phi$ in the light emitted from the point sources reach one point $P_a$ on the back focal plane of the lens 40. Scattered light beams $L_4$ to $L_6$ having another fixed set of elevation angle $\theta$ and azimuth $\phi$ in the light emitted from the point light sources reach another point $P_b$ on the back focal plane of the lens 40. The light beams $L_2$, $L_5$ are those emitted from the point source on the front focal point of the lens 40 and thus advance in parallel with the optical axis of the lens 40 after entering the lens 40. In the light $L_0$, the part not scattered by the object 2 advances in parallel with the optical axis of the lens 40, so as to enter the lens 40, thereby being converged at a back focal position Po of the lens 40.

When the object 2 moves in the $-\eta$ direction, the optical frequencies observed at the points $P_a$ and $P_b$ are lower and higher than the original optical frequency $f_b$, respectively, under the Doppler shift effect. Since the scattering angle (elevation angle $\theta$, azimuth $\phi$) is expanded on the back focal plane of the lens, the images on back focal of the lens plane are also referred to as angular spectrum. A light beam having a large elevation angle is converged at a position far from the center point Po on the back focal plane of the lens. In sum, scattered light beams having the same scattering angle is converged at a single point on the back focal plane of the lens even when coming from different virtual point sources.

Figure 4:
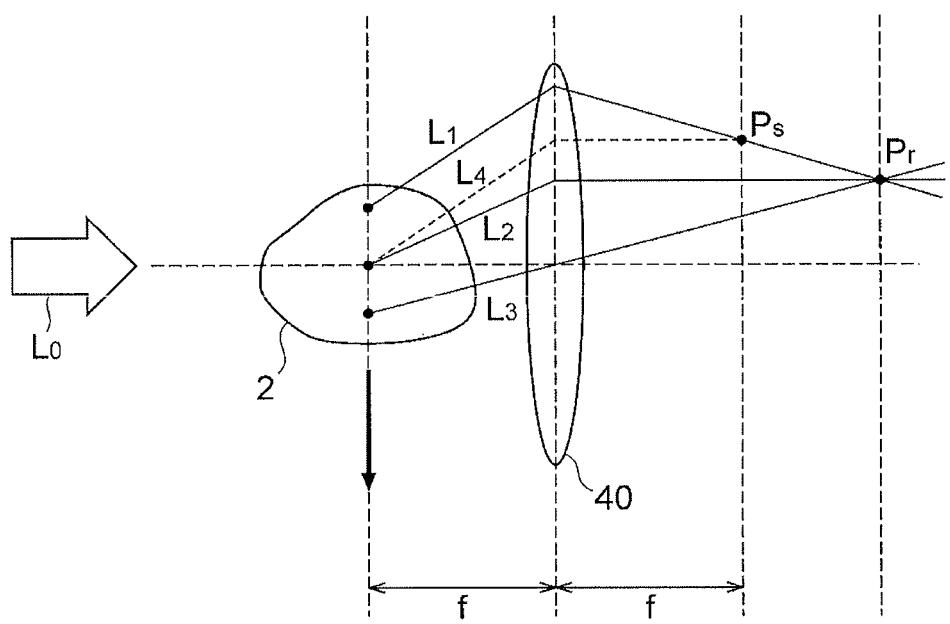
FIG. 4 is a diagram for further explaining the positions at which the scattered light generated by the object reaches the back focal plane of the lens.

FIG. 4 is a diagram for further explaining the positions at which the scattered light generated by the object reaches the back focal plane of the lens. Here, scattered light beams $L_1$ to $L_3$ are assumed to be emitted at different scattering angles from different virtual point sources on the front focal plane of the lens in the object 2. Scattered light $L_4$ emitted from a virtual point light source at the front focal point of the lens 40 advances in parallel with the optical axis of the lens 40 after entering the lens 40, thereby passing a point $P_s$ on the back focal plane of the lens 40. The scattered light $L_1$ emitted from a given virtual point source on the front focal plane of the lens 40 passes the point $P_s$ on the back focal plane of the lens 40 when its scattering angle is the same as that of the scattered light $L_4$ emitted from the virtual point light source at the front focal point of the lens 40. The scattered light $L_2$ emitted from the virtual light source on the front focal point of the lens 40 has a scattering angle different from that of the scattering light $L_4$ and thus does not pass through the point $P_s$ while advancing in parallel with the optical axis of the lens 40 after entering the lens 40. The scattered light $L_3$ emitted from another virtual point source on the front focal plane of the lens 40 does not change its advancing direction before and after entering the lens 40 when assumed to pass through the center of the lens 40. Finally, the light beams $L_1$ to $L_3$ are converged at a point $P_r$ further behind the back focal plane of the lens. Scattered light beams having different scattering angles do not intersect at a single point on the back focal plane of the lens.

Figure 5:
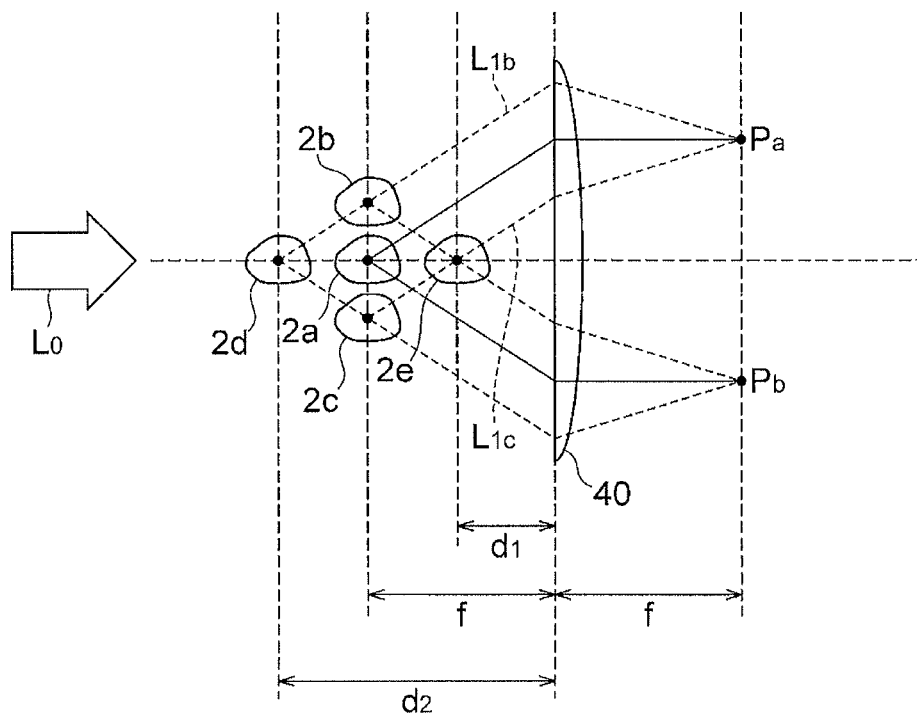
FIG. 5 is a diagram for explaining the positions at which the scattered light generated by the object reaches the back focal plane of the lens when the object moves.

FIG. 5 is a diagram for explaining the positions at which the scattered light generated by the object reaches the back focal plane of the lens when the object moves. Here, objects 2a to 2e located to respective positions are illustrated. The objects 2a to 2e are assumed to include virtual point sources therein. The virtual point source in the object 2a exists at the front focal point of the lens. The virtual point sources in the objects 2b, 2c are located above and below the position of the virtual point source in the object 2a, respectively. The virtual point sources in the objects 2d, 2e are located in upper and lower region of the position of the virtual point source in the object 2a, respectively. Since the objects 2a to 2e are irradiated with spatially uniform light $L_0$, scattered light beams generated at the respective point sources in the objects 2a to 2e have a fixed intensity distribution in an angle spectrum. That is, even when the object 2 locates at different position, the angle spectrum on the lens back focal plane yields a fixed intensity distribution.

The light changes in its phase as the object 2 locates at different position. For example, the optical path length difference between the path lengths by which the light beams $L_{1b}$, $L_{1c}$ emitted from the respective point sources in the objects 2b, 2c on the front focal plane of the lens reach the point $P_a$ on the back focal plane of the lens. The optical path length by which the light $L_{1b}$ generated by the point source in the object 2b reaches the entrance surface of the lens 40 and the optical path length by which the light $L_{1c}$ generated by the point light source in the object 2c reaches the entrance surface of the lens 40 are equal to each other. However, the optical path lengths of the light beams $L_{1b}$, $L_{1c}$ from the entrance surface of the lens 40 to the point $P_a$ differ from each other because of differences in thickness of the lens 40. As the object 2 moves at a constant velocity, the optical path length difference changes linearly with time.

Figure 6:
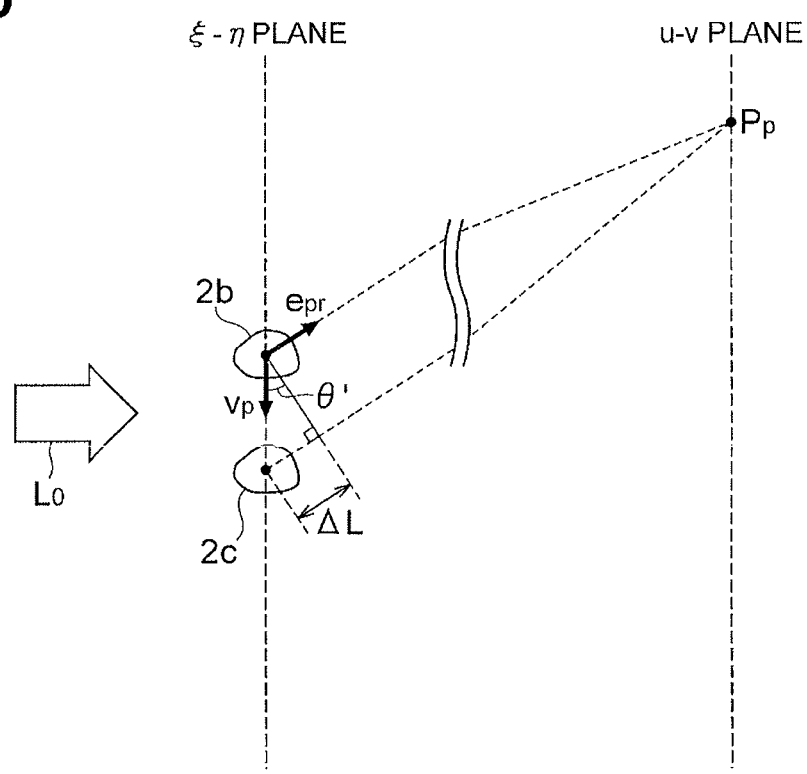
FIG. 6 is a diagram for explaining changes that occur in the optical path length until scattered light generated by the object reaches the back focal plane of the lens when the object moves.

FIG. 6 is a diagram for explaining changes in optical path length by which scattered light generated by the object reaches the back focal plane of the lens when the object moves. Assumed here is a case where scattered light is observed at infinity without using the lens 40. When the object 2 moves from the position of the object 2b to that of the object 2c, observing the scattered light at the point $P_a$ on the front focal plane of the lens is equal to observing it at infinity.

When the object 2 moves in the $-\eta$ direction on the $\xi\eta$ plane, the amount of change $\Delta L$ per unit time in optical path length by which the scattered light generated by the object 2 reaches a point $P_p$ on the uv plane is represented by the following expression (1). Here, $e_{pr}$ is the scattering direction unit vector, while $v_p$ is the velocity vector of the object 2. Using the amount of change $\Delta L$ per unit time in optical path length, the phase difference, i.e., amount of change in optical frequency $f_d$, is represented by the following expression (2). Here, $\lambda$ is the wavelength of light. When observing the scattered light at the position $P_p$ on the uv plane, the optical path length of the scattered light reaching the position $P_p$ changes as the object 2 moves, thereby varying the optical frequency. This causes the Doppler shift.

[Math. 1]
$$\Delta L = e_{pr} \cdot v_p \quad (1)$$

[Math. 2]
$$f_d = \frac{\Delta L}{\lambda} \quad (2)$$
$$= \frac{e_{pr} \cdot v_p}{\lambda}$$

The Doppler shift can also be explained in terms of "time shift" which is one of properties of Fourier transforms. Let $g(x)$ and $G(k)$ be the complex amplitude of and Fourier transform of the object 2, respectively. When the object 2 moves from position $x_0$ to position $(x_0+x)$, the Fourier transform of the object 2 after the movement is represented by the following expression (3). The term in the exponential function in the right side of the expression (3) represents the phase. As the object 2 moves, the phase rotates in proportion to the wave number vector k, thereby causing a frequency shift. Letting $\phi$ be the phase in the exponential function, the frequency shift $f_d$ is represented by the following expression (4). Here, $e_{pr}$ is the unit vector of the wave number vector k. Here, $v_p$ represents the time derivative of the position x, i.e., the velocity of the object 2. The expression (4) coincides with the above-mentioned frequency shift expression (2) explained from the optical path length change per unit time.

[Math. 3]
$$G'(k) = \exp(ikx)G(k) \quad (3)$$

[Math. 4]
$$f_d = \frac{1}{2\pi} \frac{\partial \phi(t)}{\partial t} \quad (4)$$
$$= \frac{1}{2\pi} \frac{\partial (k \cdot x)}{\partial t}$$
$$= \frac{e_{pr} \cdot v_p}{\lambda}$$

Figure 7:
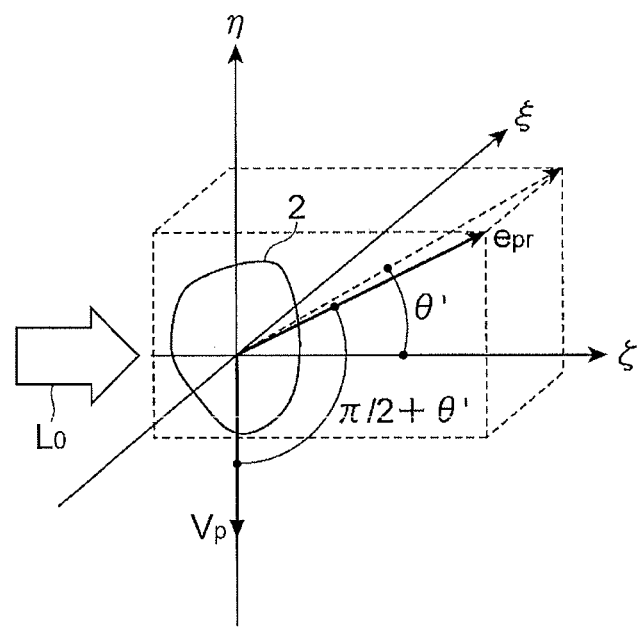
FIG. 7 is a diagram for explaining an angle formed between a scattering direction unit vector of the scattered light generated by the object and a velocity vector of the moving object.

FIG. 7 is a diagram for explaining an angle formed between a scattering direction unit vector of the scattered light generated by the object and a velocity vector of the object 2. Let $\theta'$ be the angle formed between the projection of the scattering direction unit vector $e_{pr}$ on the $\eta\zeta$ plane and the $\zeta$ axis. Here, the angle formed between the scattering direction unit vector $e_{pr}$ and the velocity vector $v_p$ of the object 2 is $\theta'+\pi/2$. Therefore, the inner product of the scattering vector and velocity vector in the right side of the expression (2) or (4) is represented by the following expression (5). Here, V is the moving speed of the object 2. Since the numerical aperture NA of the lens 40 is defined by $\sin\theta'$, a Nyquist frequency $f_{nyq}$ for obtaining a blur-free image is represented by the following expression (6).

[Math. 5]
$$f_d = \frac{e_{pr} \cdot v_p}{\lambda} \quad (5)$$
$$= \frac{V}{\lambda}\cos(\theta' + \pi/2)$$
$$= -\frac{V}{\lambda}\sin\theta'$$

-continued

[Math. 6]

$$f_{nyq} = \frac{V}{\lambda}NA \quad (6)$$

Next, employing specific values, the amount of change in optical frequency $f_d$ caused by the Doppler shift is estimated. Assuming that the object 2 is caused to flow by a commercially available flow cytometer at present, let the moving speed of the object 2 be 1 m/s. The light $L_O$ irradiating the object 2 is assumed to be HeNe laser light having a wavelength of 633 nm. Suppose that the lens 40 has an NA of 0.45 and a magnification equivalent to 20×. When thus constructed lens 40 is used, the maximum value of the sine of the scattering angle θ' with respect to the velocity vector $v_p$ becomes 0.45. Therefore, the maximum Doppler shift frequency is estimated to be 710 kHz from the expression (5). When the speed is 100 μm/s, a maximum Doppler shift frequency of 71 Hz is observed.

Through the lens 40 having a focal length f, the scattered light having the scattering angle θ' reaches the position represented by the following expression (7) on the uv plane. Therefore, using the expressions (5) and (7) and the approximate equation of $\tan\theta' \approx \sin\theta'$, which holds when the angle θ' is small, the Doppler shift frequency $f_d$ can be expressed as a function of a v-coordinate value as in the following expression (8). It is expressed by the following expression (9) when no approximation is used.

[Math. 7]

$$v = f\tan\theta' \quad (7)$$

[Math. 8]

$$f_d = -\frac{V}{\lambda}\frac{v}{f} \quad (8)$$

[Math. 9]

$$f_d = -\frac{V}{\lambda}\sin\left(\arctan\frac{v}{f}\right) \quad (9)$$

Figure 8:
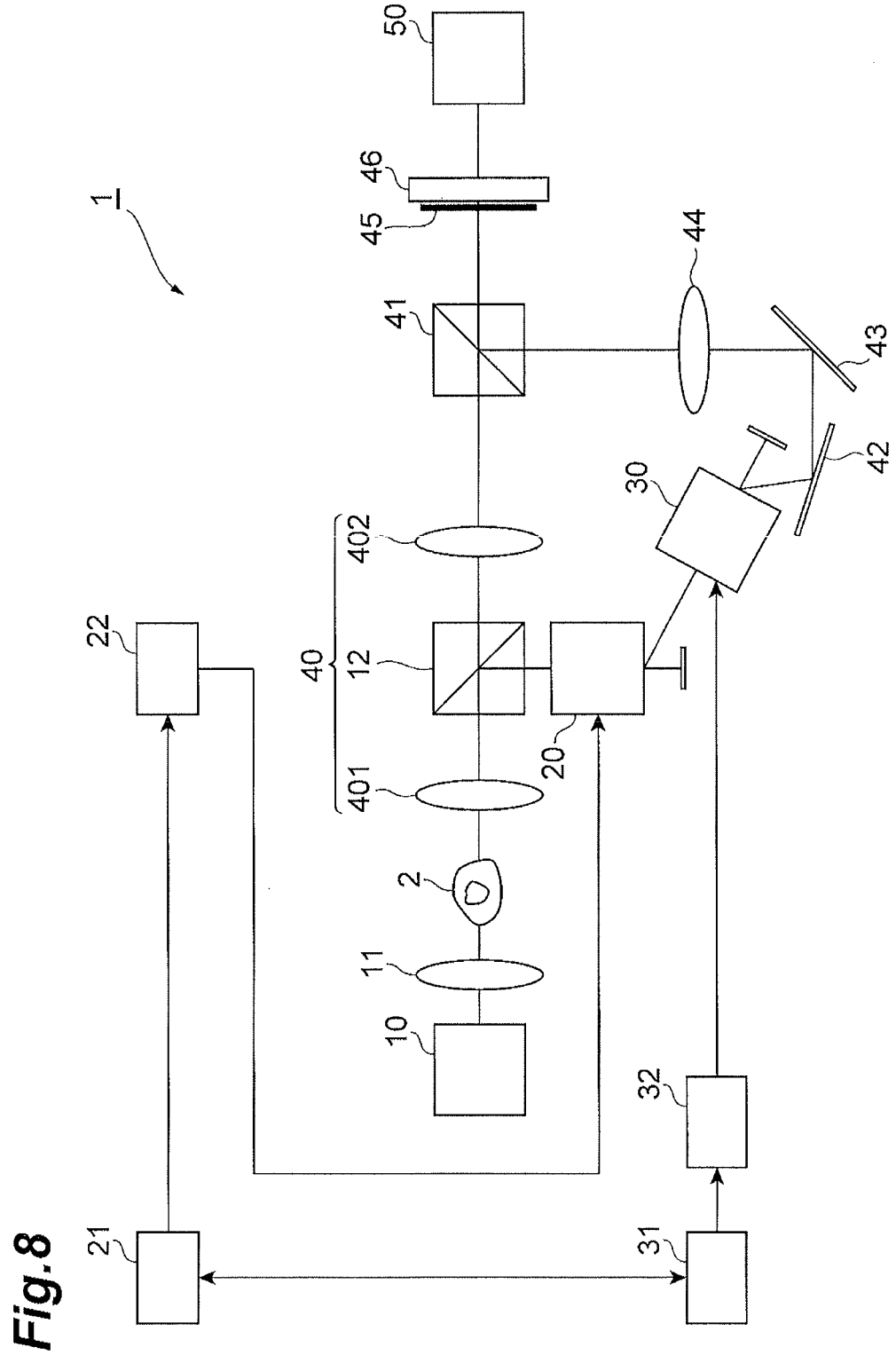
FIG. 8 is a diagram illustrating a structure of an observation device 1 in accordance with the embodiment.
Figure 9:
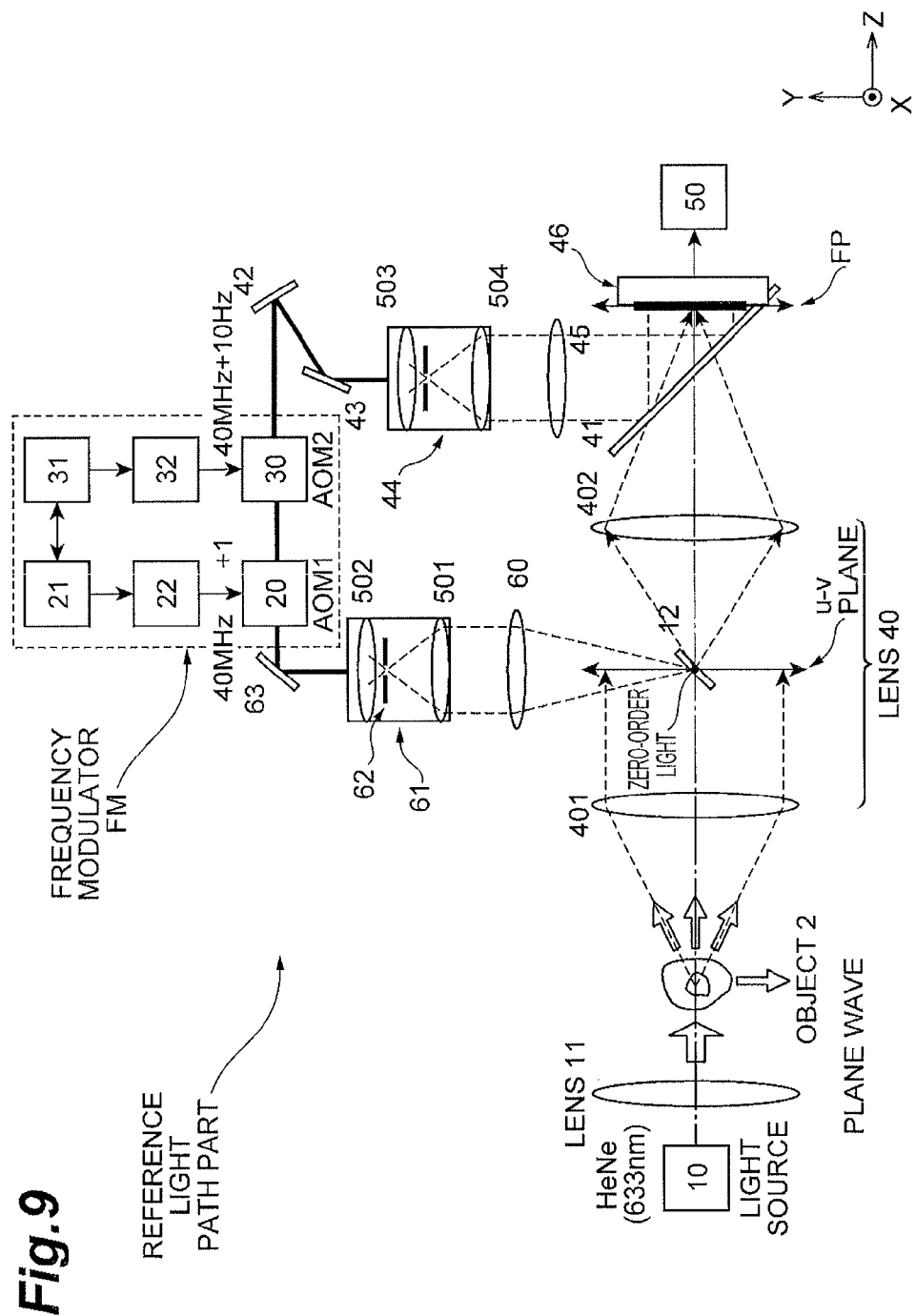
FIG. 9 is a diagram illustrating a detailed structure of the observation device 1 in accordance with the embodiment.

The observation device 1 in accordance with this embodiment acquires a phase image of the object 2 according to the principle explained in the foregoing. FIG. 8 is a diagram illustrating a structure of the observation device 1 in accordance with this embodiment. The observation device 1 in accordance with this embodiment comprises a light source 10, an illumination lens 11, a beam splitter 12, a first modulator 20, a first signal generator 21, a first amplifier 22, a second modulator 30, a second signal generator 31, a second amplifier 32, the lens 40, a beam splitter 41, mirrors 42, 43, a lens 44, a neutral density filter 45, a photodetector 46, and an arithmetic unit 50. The lens 40 is constituted by lenses 401, 402. FIG. 9 is a diagram illustrating the foregoing structure of the observation device 1 more specifically.

The light source 10, an example of which is an HeNe laser light source, outputs light (optical frequency $f_b$) for irradiating the object 2. The beam splitter 12 is arranged between the lenses 401, 402. The beam splitter 12 receives the light emitted from the light source 10, splits thus received light in two, and outputs the first light to the beam splitter 41 through the lens 402 and the second light to the first modulator 20. An example of the first and second modulators 20, 30 is an acousto-optic device. The first modulator 20 is provided with a first modulation signal amplified by the first amplifier 22 after being issued from the first signal generator 21, diffracts the light emitted from the light source 10, and outputs thus diffracted light to the second modulator 30. The second signal modulator 30 is provided with a second modulation signal amplified by the second amplifier 32 after being issued from the second signal generator 31, diffracts the light emitted from the first modulator 20, and outputs thus diffracted light to the mirror 42.

An example of the respective intensities of the first and second modulation signals fed to the first and second modulators 20, 30 is 29 dBm. The frequencies (first and second modulation frequencies) of the first and second modulation signals slightly differ from each other. For example, the first and second modulation frequencies are 40 MHz and 40.000010 MHz, respectively, which yield a difference Δf of 10 Hz therebetween. Each of the first and second modulation signals is a sine wave. The first and second signal generators 21, 31 are connected to each other by wiring in order to synchronize them.

Figure 12:
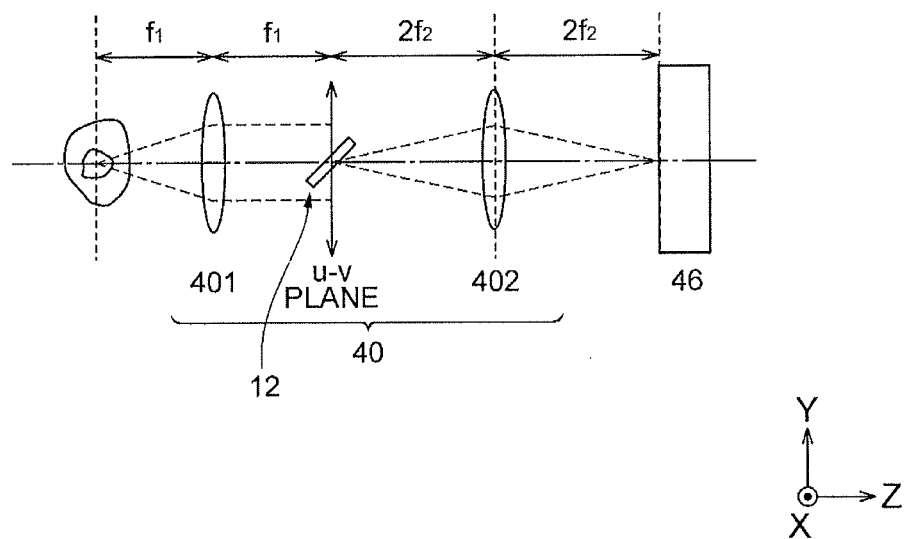
FIG. 12 is a diagram illustrating a structural example of the lens 40 included in the observation device 1 of the embodiment.

The lens 40 receives the scattered light generated by the object 2 upon irradiation with the light from the lens 11 and forms a Fourier transform image of the object 2. FIG. 12 illustrates the structure of the lens 40. As illustrated in FIG. 12, the lens 40 is constituted by the lenses 401, 402, between which the beam splitter 12 is arranged. Dotted lines in FIG. 12 illustrate how an image is formed.

As illustrated in FIG. 12, a Fraunhofer diffraction image of the object is obtained on the back focal plane of the lens 401. At the center of the Fraunhofer diffraction image of the object on the back focal plane of the lens 401, light unaffected or less influenced by scattering appears. The light concentrating at the center of the Fraunhofer diffraction image is referred to as zero-order light. The zero-order light and the diffracted light that can be regarded as the zero-order light are light components which are unaffected or less influenced by scattering. In this specification, these light components are referred to as substantially zero-order light. The substantially zero-order light is diffracted light having such a scattering direction unit vector $e_{pr}$ that the Doppler shift frequency $f_d$ represented by the above-mentioned expression (2) becomes substantially 0 when the scattering direction unit vector $e_{pr}$ and the velocity vector $v_p$ of the object 2 are substantially orthogonal to each other.

That is, the Doppler shift frequency $f_d$ of the substantially zero-order light having passed through the object 2 is substantially zero. The beam splitter 12, which is arranged on the back focal plane of the lens 401, extracts the substantially zero-order light from the light having passed through the object 2. The beam splitter 12 splits the light issued from the lens 401 in two and outputs one of them as the first light to the lens 402. On the other hand, as illustrated in FIG. 9, the beam splitter 12 guides the reflected substantially zero-order light as the second light to the first modulator 20 through lenses 60, 61, a pinhole 62, and a mirror 63.

The front focal plane of the lens 60 coincides with the back focal plane of the lens 401 (uv plane). The lens 60 outputs as collimatedlight the substantially zero-order light issued from the beam splitter 12. The collimatedlight emitted from the lens 60 has its beam diameter expanded and reduced by the lens 61. The lens 61 represents a so-called 4f optical system constituted by two lenses, i.e., lenses 501, 502. The 4f optical system is an optical system in which the back focal plane of the lens 501 coincides with the front focal plane of the lens 502, so that an image on the front focal plane of the lens 501 is formed on the back focal plane of the lens 502.

The pinhole 62 is arranged on the back focal plane of the lens 501. The size of the pinhole 62 can be changed, so as to adjust the purity of a zero-order component in the substantially zero-order light extracted by the beam splitter 12. The purity of the zero-order light component becomes higher and lower when the pinhole diameter is smaller and larger, respectively. The second light is fed into the first modulator by way of the mirror 63 after the beam diameter and the purity of the zero-order light component are adjusted by the lens 61 and the pinhole 62.

The lens 11 collimates the light emitted from the light source 10 and irradiates the object 2 with the collimated light. The lens 44 collimates the light successively reflected by the mirrors 42, 43 after being issued from the second modulator 30 and outputs it to the beam splitter 41. The lens 44 is constituted by lenses 503, 504, which employs the structure of a 4f optical system. After being adjusted to a desirable beam diameter by the lens 44, the light is fed to the beam splitter 41.

The beam splitter 41 makes the respective light beams arriving from the lenses 40, 44 incident on the light-receiving surface of the photodetector 46 and causes a heterodyne interference between the light beams on the light-receiving surface. That is, the light passing through the object 2 after being emitted from the light source 10 is received by the beam splitter 12 and split thereby in two so as to yield first light and second light, the second light is modulated by the modulators 20, 30, and then the beam splitter 41 causes a heterodyne interference between the first light and the modulated second light on a predetermined plane. The neutral density filter 45 is arranged in front of the light-receiving surface of the photodetector 46. The frequency of the light incident on the light-receiving surface of the photodetector 46 after being issued from the second modulator 30 becomes $f_b+\Delta f$, where $\Delta f$ is the difference frequency between the first and second modulation frequencies.

Assuming that the object 2 moves in the $-\eta$ direction on the $\xi\eta$ plane, the first direction yielding a fixed Doppler shift frequency concerning the movement of the object 2 in the light having reached the light-receiving surface of the photodetector 46 through the lens 40 is the u direction parallel to the $\xi$ axis. That is, the first direction is a direction perpendicular to the moving direction of the object 2. The second direction orthogonal to the first direction on the light-receiving surface is the v direction parallel to the $\eta$ axis. That is, the second direction is a direction parallel to the moving direction of the object 2. The photodetector 46 can output data representing a sum in the second direction (v direction) of data temporally changing at a frequency corresponding to a Doppler shift frequency of the light having reached each position on the light-receiving surface through the lens 40 at each position in the first direction (u direction) at each time.

The photodetector 46 preferably has a pixel array structure in the first direction (u direction), while each pixel preferably has a photosensitive region elongated in the second direction (v direction). The light-receiving surface of the photodetector 46 may be arranged on the back focal plane in the first direction of the lens 40 while coinciding with the back focal plane in the second direction of the lens 40 (a first arrangement example which will be explained later), may be an image plane (imaging plane) where an image of the object 2 is formed by the lens 40 in the first direction while coinciding with arranged on a plane where an image of the object 2 is formed in the second direction (second and fifth arrangement examples), or may be arranged on a given plane (Fresnel diffraction plane) perpendicular to the optical axis in front or rear of the lens 40 in each of the first and second directions (third and sixth arrangement examples).

The light-receiving surface of the photodetector 46 may be arranged on a plane where Fraunhofer diffraction images of the object are formed in the first and second directions by the lens 40 (seventh arrangement example); a plane where a Fraunhofer diffraction image of the object is formed in the first direction by the lens 40, which is also a plane where an image of the object is formed in the second direction (eighth arrangement example); or a plane where Fraunhofer and Fresnel diffraction images of the object are formed in the first and second directions, respectively, by the lens 40 (ninth arrangement example).

The light-receiving surface of the photodetector 46 may be arranged on a plane where an image of the object is formed in the first direction by the lens 40, which is also a plane where a Fraunhofer diffraction image of the object is formed in the second direction (tenth arrangement example); may be arranged on a plane where images of the object are formed in the first and second directions by the lens 40 (eleventh arrangement example); or may be arranged on a plane where an image of the object is formed in the first direction by the lens 40, which is also a plane where a Fresnel diffraction image of the object is formed in the second direction (twelfth example).

The light-receiving surface of the photodetector 46 may be arranged on a plane where Fresnel and Fraunhofer diffraction images of the object are formed in the first and second directions, respectively, by the lens 40 (thirteenth arrangement example); a plane where a Fresnel diffraction image of the object is formed in the first direction by the lens 40, which is also a plane where an image of the object is formed in the second direction (fourteenth arrangement example); or a plane where Fresnel diffraction images of the object are formed in the first and second directions by the lens 40 (fifteenth arrangement example).

The arithmetic unit 50 performs a predetermined arithmetic operation of data, issued from the photodetector 46, employing the position in the first direction (u direction) on the light-receiving surface and time as variables, so as to obtain an image of the object 2. For carrying out this operation, the arithmetic unit 50 comprises a first Fourier transform device 51 for performing a one-dimensional Fourier transform with respect to a time variable and a second Fourier transform unit 52 for performing a two-dimensional Fourier transform. The second Fourier transform unit 52 comprises a third Fourier transform device 53 for performing a one-dimensional Fourier transform with respect to the frequency and a fourth Fourier transform device 54 for performing a one-dimensional Fourier transform with respect to the first direction. Details of the arithmetic operation will be explained later.

Figure 10:
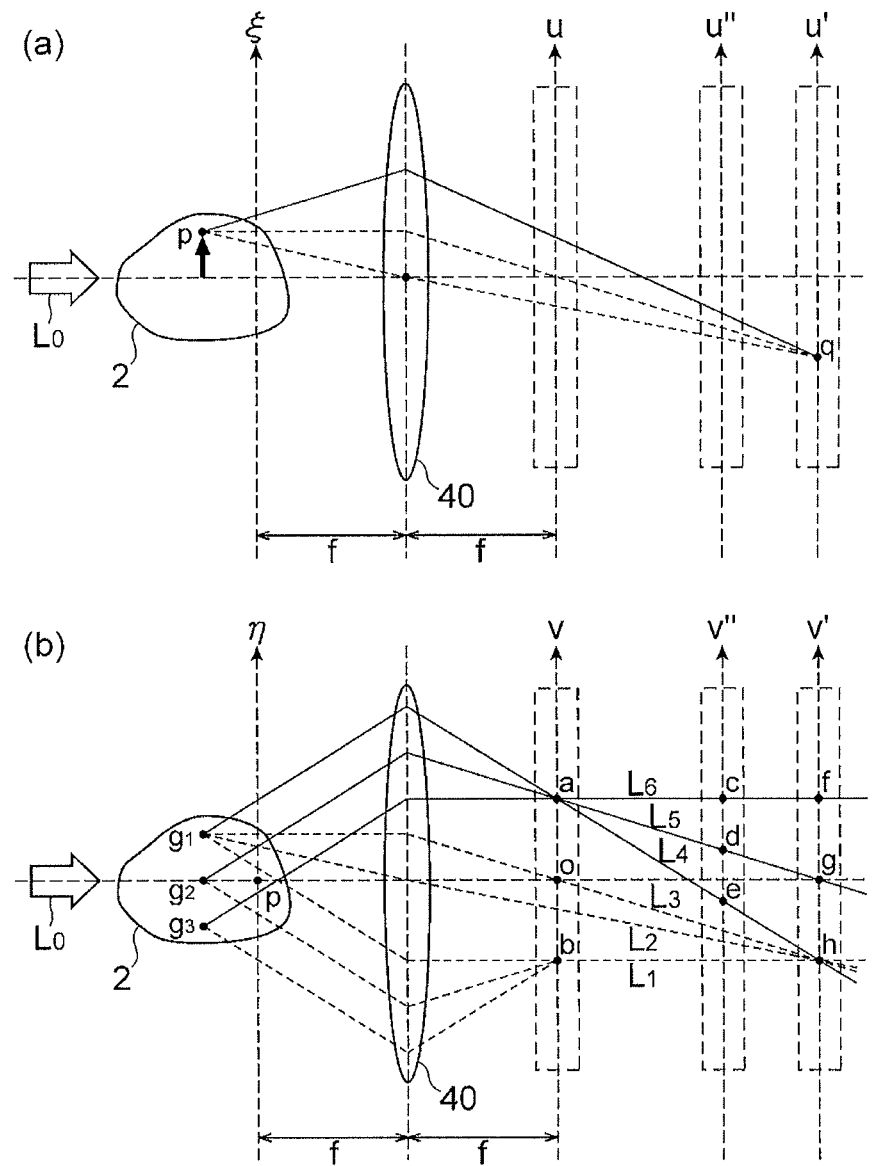
FIG. 10 is a diagram illustrating a positional relationship among an object 2, a lens 40, and a photodetector 46 in the observation device 1 in accordance with the embodiment.

FIG. 10 is a diagram illustrating a positional relationship among the object 2, lens 40, and photodetector 46 in the observation device 1 in accordance with this embodiment. In this diagram, parts (a) and (b) are views seen in the $\eta$ and $\xi$ directions, respectively. The diagram illustrates a $\xi\eta$ coordinate system having an origin at the front focal point of the lens 40, an xy coordinate system having an origin at the center of the lens 40, a uv coordinate system having an origin at the back focal point of the lens 40, a u'v' coordinate system having an origin at the imaging plane center position produced by the lens 40, and a u"v" coordinate system having an origin at a given position on the optical axis of the lens 40. The light-receiving surface of the photodetector 46 coincides with the uv, u'v', and u"v" planes in the first, second, and third arrangement examples, respectively.

As illustrated in part (b) of the diagram, light beams $L_4$ to $L_6$ generated at the same angle in virtual point sources $g_1$ to $g_3$ in the object 2 intersect at one point a on the uv plane, which is the back focal plane of the lens, and then diverge, so as to reach points h, g, and f on the u'v' plane, which is the imaging plane of the lens. The light beams $L_4$ to $L_6$ have the same scattering angle θ' and thus incur the same frequency shift by Doppler effect.

A difference between respective signals received by the photodetector 46 in the first and second arrangement examples will now be explained. In the first arrangement example, a frequency shift is observed with regularity in the v direction, while a one-to-one relationship exists between the position in the v direction and the frequency shift amount. In the second arrangement example, on the other hand, no frequency shift is arranged with regularity in the v' direction, and no one-to-one relationship exists between the position in the v' direction and the frequency shift amount.

For placing irregularly arranged frequency shift in the v' direction in order (i.e., in such an order that they are observed on the light-receiving surface of the photodetector 46 in the first arrangement example) in the second arrangement example, a Fourier transform is performed after combining (summing) the waveforms observed at the points f, g, and h on the u'v' plane; this makes their frequency linear (regular), while yielding their amplitude and phase.

Figure 13:
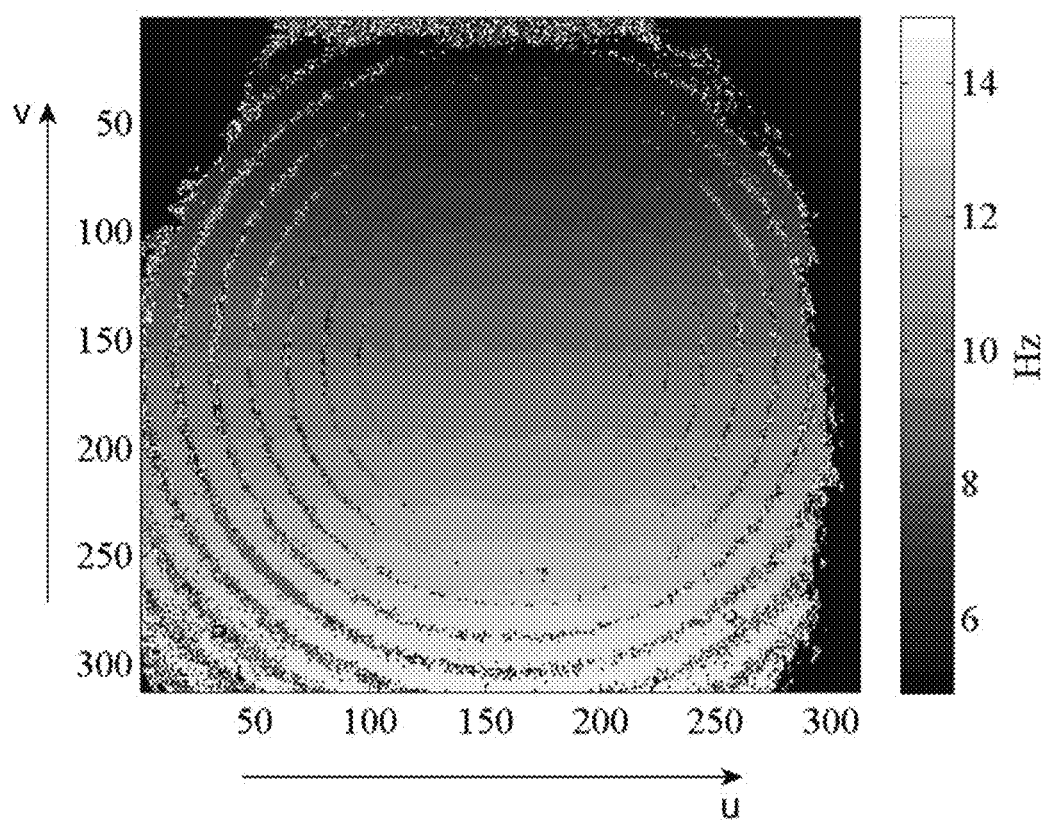
FIG. 13 is a diagram illustrating an example of frequency distributions in interference images captured by the photodetector 46 when employing the first arrangement example in the observation device 1 of the embodiment.

This is equivalent to the fact that the amplitude and phase at each frequency are obtained by a Fourier transform after summing waveforms $h_1$, $h_2$, and $h_3$ in the v direction as illustrated in the graph in FIG. 13 in the first arrangement example in which frequency shifts are arranged with regularity in the v direction on the light-receiving surface of the photodetector 46 as well. In other words, as long as the photodetector 46 has a light-receiving surface in such a size as to cover the scattered light incurring a Doppler shift caused by the object 2, there are no changes in obtained signals regardless of where the photodetector 46 receives light, and the distribution obtained on the light-receiving surface of the photodetector 46 in the first arrangement example can be restored since it is encoded with the frequency.

On the other hand, as illustrated in part (a) of FIG. 10, no Doppler shift is incurred with respect to the u direction, so that the distribution cannot be restored by arithmetic operations and the like even when signals are integrated in the u direction. Because of the foregoing, the photodetector 46 is required to have a pixel array structure in the u direction but not in the v direction.

Figure 11:
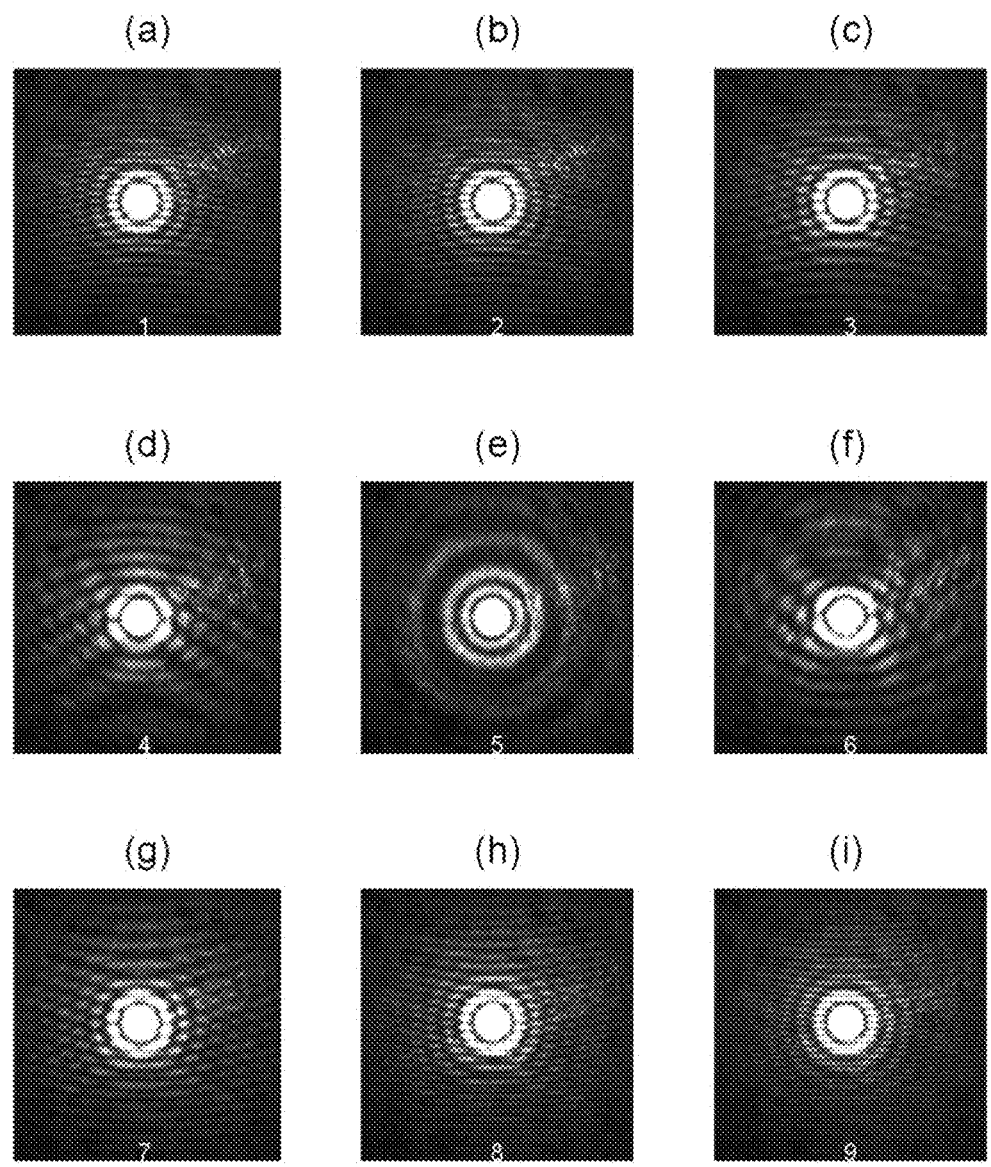
FIG. 11 is a diagram illustrating examples of interference images captured by the photodetector 46 when employing a first arrangement example in the observation device 1 of the embodiment.

FIG. 11 is a examples of interference images captured by the photodetector 46 when employing the first arrangement example in the observation device 1 of this embodiment. Here, the object 2, for which one having a circular aperture with a diameter of 50 μm was employed, was moved at a velocity of 30 μm/s. The light-receiving surface of the photodetector 46, for which a two-dimensional CCD camera was used, was arranged on the back focal plane of the lens 40. As the lens 40, one having a structure including an objective lens 401 (having a magnification of 20×) and a relay lens 402 (having a focal length of 30 mm) as illustrated in FIG. 12 was used, while an image on the back focal plane located within the objective lens 401 was formed on the light-receiving surface of the photodetector 46 by the relay lens 402.

Parts (a) to (i) in FIG. 11 illustrate respective interference images captured at intervals of 1 sec in sequence. As can be seen from the images, a diffraction pattern (so-called airy disk pattern) caused by the circular aperture does not change, though interference fringes vary as time passes. This phenomenon empirically shows that only the phase changes while the intensity distribution of angular spectrum of scattered light reaching the back focal plane of the lens is constant even when the object 2 moves in the −η direction on the ξη plane as explained with reference to FIG. 5.

FIG. 13 is an example of frequency distributions in interference images captured by the photodetector 46 when employing the first arrangement example in the observation device 1 of the embodiment. Here, the object 2, for which one having a circular aperture with a diameter of 200 μm was employed, was moved at a velocity of 100 μm/s. The light-receiving surface of the photodetector 46, for which a two-dimensional CCD camera was used, was arranged on the back focal plane of the lens 40. As the lens 40, one constructed as illustrated in FIG. 12 (but with a different magnification) was used. As illustrated in FIG. 13, the frequency changes along the v direction (second direction) from 10 Hz as a center, which is the difference frequency Δf between the first and second modulation frequencies. This is the Doppler shift frequency itself. On the other hand, a frequency is fixed along the u direction (first direction).

Details of arithmetic operations in the arithmetic unit 50 in the respective cases employing the first to fifteenth arrangement examples in the observation device 1 in accordance with this embodiment will now be explained.

First Arrangement Example

In the first arrangement example, the light-receiving surface of the photodetector 46 is arranged on the back focal plane in the first direction of the lens 40, which is also the back focal plane (uv plane) in the second direction of the lens 40. Here, the Fourier transform image on the uv plane of an complex amplitude image g(ξ, η) of the object 2 on the plane ξη plane by the lens 40 is represented by the following expression (10). The expression (10) includes a term of a Fourier transform image G(u, v) of the object 2 and completely coincides with G(u, v) under the condition where d=f.

[Math. 10]

$$G''(u, v) = \frac{A\exp\left[j\frac{k}{2f}\left(1 - \frac{d}{f}\right)(u^2 + v^2)\right]}{j\lambda f} \int\int g(\xi, \eta)\exp\left[-j\frac{2\pi}{\lambda f}(\xi u + \eta v)\right]d\xi d\eta \quad (10)$$

In the structure of the observation device 1, the scattered light (having an optical frequency of $f_b - f_d$) transmitted through the lens 40 after having received a Doppler shift from the object 2 and the reference light (having an optical frequency of $f_b + \Delta f$) whose frequency is shifted by Δf from the optical frequency $f_b$ by the first and second modulators 20, 30 reach the uv plane (the light-receiving surface of the photodetector 46), which is the back focal plane of the lens 40, through the beam splitter 41. Because of a heterodyne interference between these light beams on the uv plane, a beat signal having the difference frequency $(\Delta f + f_d)$ between the respective optical frequencies of the scattered light and reference light is observed at each position on the uv plane. The optical frequency change amount $f_d$ of the scattered light caused by the Doppler shift can be expressed as a function of the v-coordinate value as in the above-mentioned expression (8).

Figure 14:
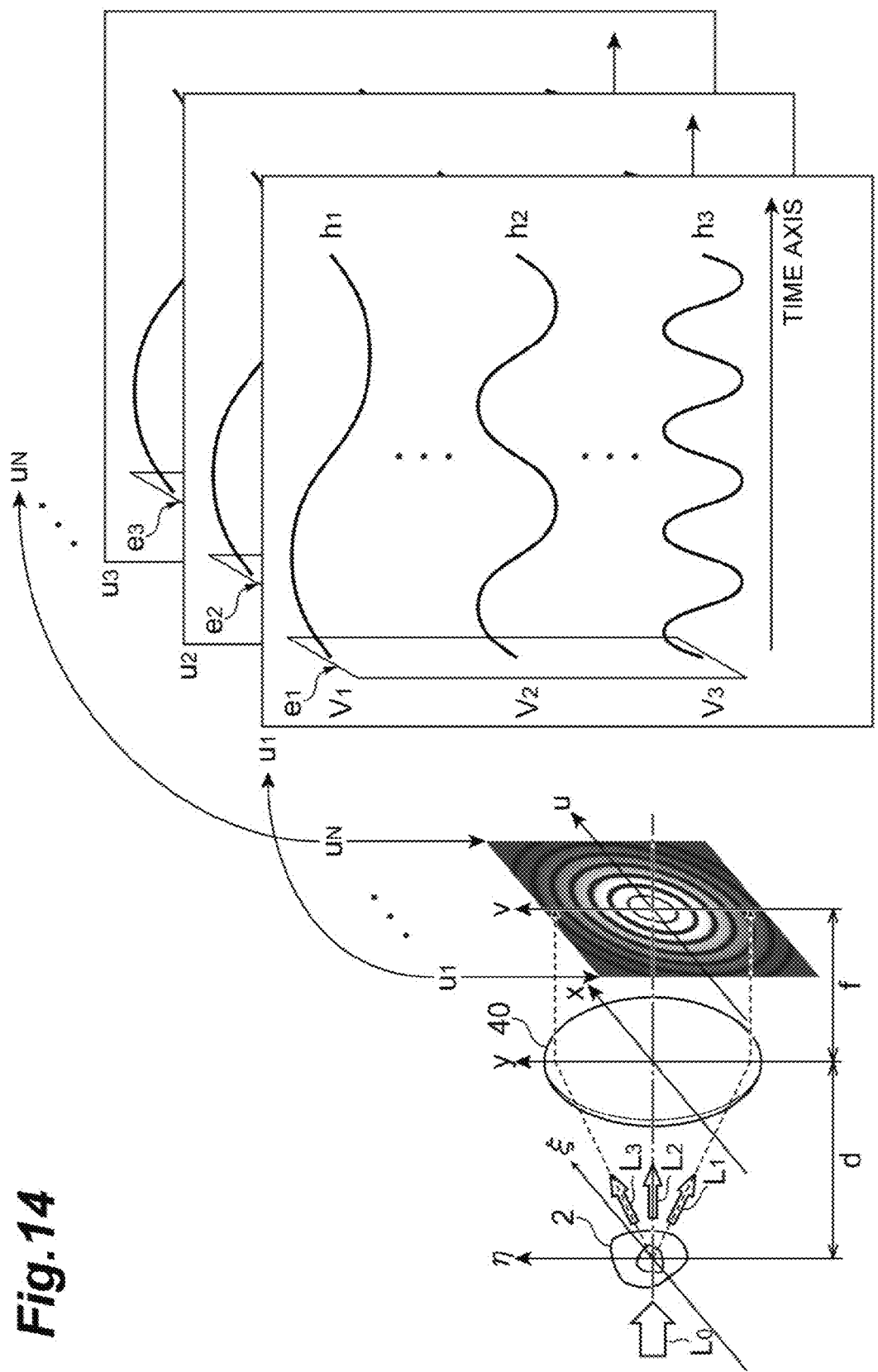
FIG. 14 is a diagram schematically illustrating signals observed on a uv plane when employing the first arrangement example in the observation device 1 of the embodiment.

FIG. 14 is a diagram schematically illustrating signals observed on the uv plane when employing the first arrangement example in the observation device 1 of this embodiment. This diagram schematically illustrates temporal waveforms of respective signals at positions $v_1$, $v_2$, $v_3$ on a line parallel to the v direction with respect to $u_n$ (n=1 to N) on the uv plane. Since the object 2 moves in the $-\eta$ direction on the $\xi\eta$ plane, a signal $h_1$ having a frequency $(\Delta f-|f_d|)$ lower than $\Delta f$ is obtained at a position $(u_n, v_1)$ where the v-coordinate value $v_1$ is positive on the uv plane. A signal $h_2$ having a frequency $\Delta f$ is obtained at a position $(u_n, v_2)$ where the v-coordinate value $v_2$ is 0 on the uv plane. A signal $h_3$ having a frequency $(\Delta f+|f_d|)$ higher than $\Delta f$ is obtained at a position $(u_n, v_3)$ where the v-coordinate value $v_3$ is negative on the uv plane.

Figure 15:
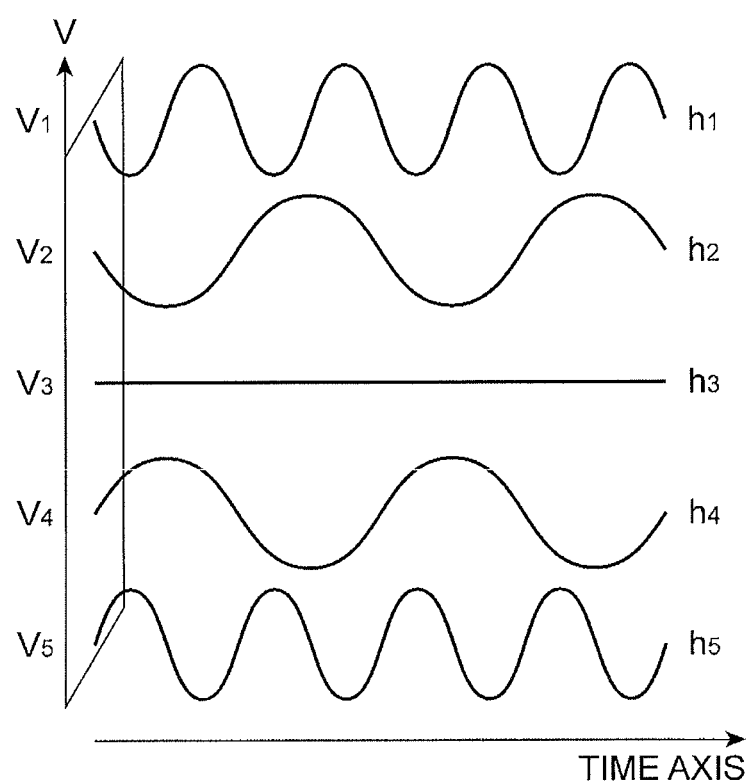
FIG. 15 is a diagram schematically illustrating signals observed on the uv plane when there is no frequency shift caused by modulators 20, 30 ($\Delta f=0$) while employing the first arrangement example in the observation device 1 of the embodiment.

For an example, FIG. 15 schematically illustrates signals observed on the uv plane when there is no frequency shift caused by the modulators 20, 30 ($\Delta f=0$) while employing the first arrangement example in the observation device 1 of this embodiment. In this case, a DC signal $h_3$ is obtained at a position $(u_n, v_3)$ where the v-coordinate value $v_3$ is 0 on the uv plane. Two positions $(u_n, v_1)$, $(u_n, v_5)$ whose v-coordinate values have the same absolute value with different signs (positive or negative) on the uv plane yield respective signals $h_1$, $h_5$ having the same frequency with phases differing from each other by $\pi$. Similarly, two positions $(u_n, v_2)$, $(u_n, v_4)$ whose v-coordinate values have the same absolute value with different signs (positive or negative) on the uv plane yield respective signals $h_2$, $h_4$ having the same frequency with phases differing from each other by $\pi$.

When the first arrangement example is employed in the observation device 1 of this embodiment, the signal $h_n$ observed at a position $(u_n, v)$ on the uv plane, which is the back focal plane of the lens, has a frequency $\Delta f+f_d=\Delta f(V/\lambda f)$ v. That is, the signal $h_n$ observed at the position $(u_n, v)$ varies depending on the v-coordinate value. The v-coordinate value and the frequency are related to each other. Therefore, when a signal $s_1(u_n, t)$ representing the sum of signals $h_1$ to $h_N$ on a line parallel to the v direction is obtained for given $u_n$, the signal (amplitude, phase) at each position $(u_n, v)$ can be specified by analyzing the frequency of the signal $s_1(u_n, t)$.

Figure 16:
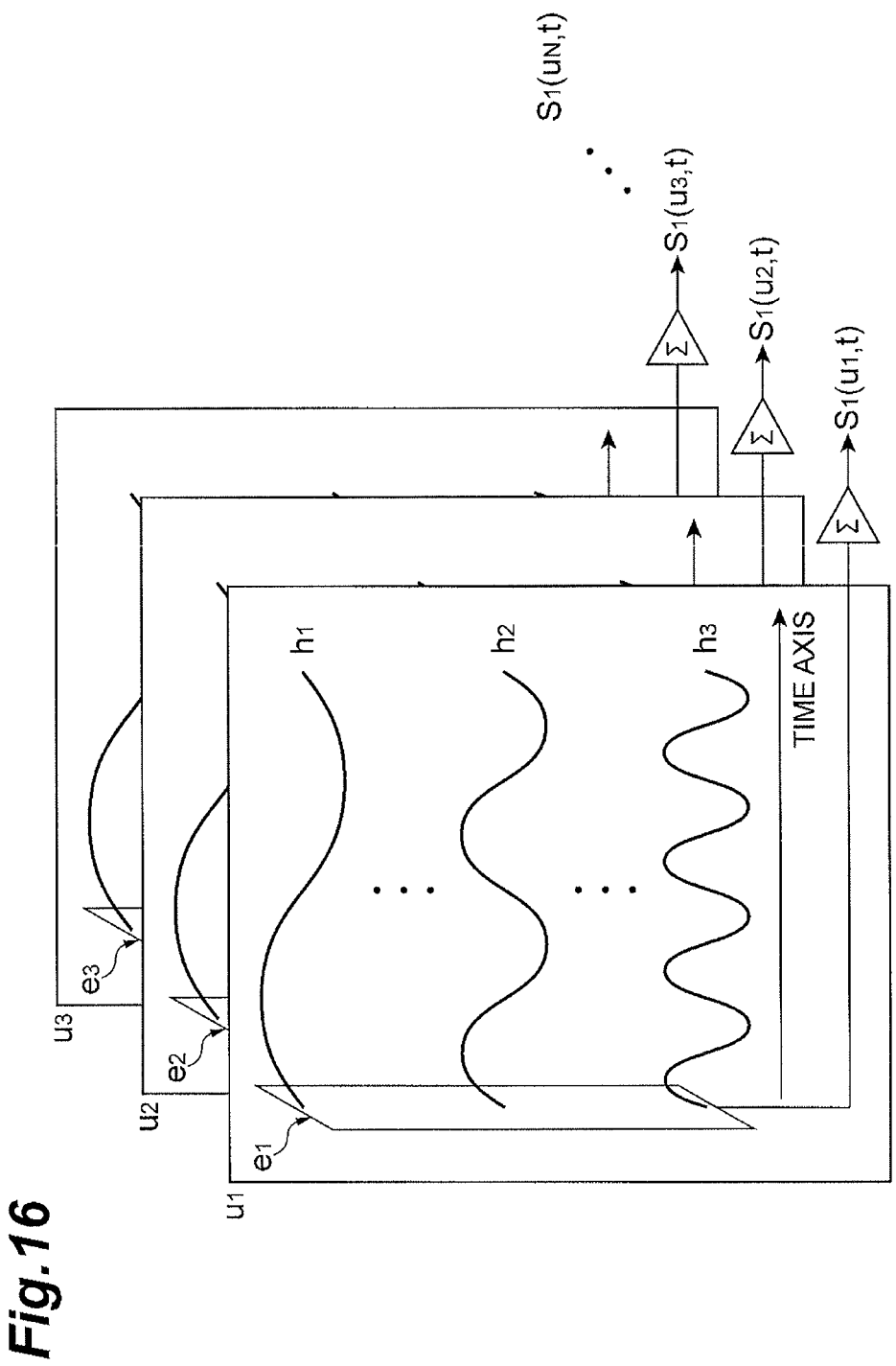
FIG. 16 is a diagram schematically illustrating an operation for obtaining a signal $s_1(u_n,t)$ representing the sum of signals $h_1$ to $h_N$ on a line parallel to a v direction for each $u_n$ when employing the first arrangement example in the observation device 1 of the embodiment.

FIG. 16 is a diagram schematically illustrating an operation for obtaining the signal $s_1(u_n, t)$ representing the sum of signals $h_1$ to $h_N$ on a line parallel to the v direction for each $u_n$ when employing the first arrangement example in the observation device 1 of this embodiment. In this diagram, sigma $\Sigma$ represents an arithmetic operation for the sum of signals $h_1$ to $h_N$. The signal $s_1(u, t)$ indicating the sum of signals $h(v)$ on a line parallel to the v direction with respect to a given u-coordinate value is represented by the following expression (11). Here, $G(u, v)$ is a Fourier transform image (complex amplitude) of the object 2 obtained on the uv plane. Sign $\angle$ represents the phase of the complex amplitude. Here, $\phi_0$ indicates the initial phase resulting from optical conditions of scattered light and reference light. $A_0$ represents the distribution in intensity of scattered light and reference light. Here, t is a time variable. The term of DC components is omitted.

[Math. 11]

$$s_1(u, t) = \int h(v)dv$$
$$= \int A_0(u, v)|G(u, v)|\cos\begin{matrix}(2\pi(\Delta f + f_d)t + \\ \angle G(u, v) + \phi_0(u, v))\end{matrix}dv \quad (11)$$

As the photodetector 46, one having a pixel array structure in which pixels $e_1$ to $e_n$ are arranged in the u direction, while the pixel $e_n$ corresponding to each $u_n$ has a photosensitive region elongated in the v direction, is favorably used as mentioned above. The signal issued from the pixel $e_n$ in the pixel array structure corresponds to the signal $s_1(u_n, t)$ represented by the above-mentioned expression (11).

The above-mentioned expression (11) is represented in complex notation by the following expression (12). Here, $\Delta\omega$ indicates $\Delta f$ in terms of angular frequency, and $\Delta\omega=2\pi\Delta d$. Here, $\omega_d$ indicates $f_d$ in terms of angular frequency, and $\omega_d=2\pi f_d$. Here, $v=a\omega_d$, and $a=\lambda f/(2\pi V)$. $A_0$ and $\phi_0$ are omitted in the expression (12). $A_0$ and $\phi_0$ will also be omitted in the following mathematical expressions.

[Math. 12]

$$s_1(u,t)=a\exp(i\Delta\omega t)\int G(u,a\omega)\exp(i\omega_d t)d\omega_d \quad (12)$$

In the right side of the expression (12), the exponential function $\exp(i\Delta\omega t)$ in front of the integral sign means that the function subsequent thereto is modulated by the frequency $\Delta\omega$. Specifically, it means that a frequency shift occurs by the frequency $\Delta\omega$ in the frequency region. This frequency shift can empirically be confirmed by the fact that a frequency shift to a frequency of 10 Hz occurs as illustrated in parts (b) and (c) of FIG. 18. The integral sign in the expression (12) indicates an inverse Fourier transform of the complex amplitude $G(u, v)$ with respect to the variable v or $\omega_d$.

A one-dimensional Fourier transform of the signal $s_1(u, t)$ with respect to the time variable t is represented by the following expression (13). The rightmost side of the expression (13) indicates a signal of $G(u, v)$, which is a two-dimensional Fourier transform image of the complex amplitude image $g(\xi, \eta)$ of the object 2, shifted by a frequency of $\Delta v=a\Delta\omega$.

[Math. 13]

$$\int s(u,t)\exp(-i\omega t)dt=aG(u,a(\Delta\omega+\omega))=aG(u,\Delta v+v) \quad (13)$$

An example (first example) in the first arrangement example will now be explained. As the photodetector 46, a digital CCD camera having 640×480 pixels, capable of capturing images at 30 frames/s, was used in the first example. Using this photodetector 46, images were captured at fixed time intervals, and image data captured at each time were fed into a personal computer (PC). An arithmetic operation by the PC determined the sum of the signals issued from the each pixel on a line parallel to the v direction with respect to a given u-coordinate value, thereby yielding data of the signal $s_1(u, t)$.

Figure 17:
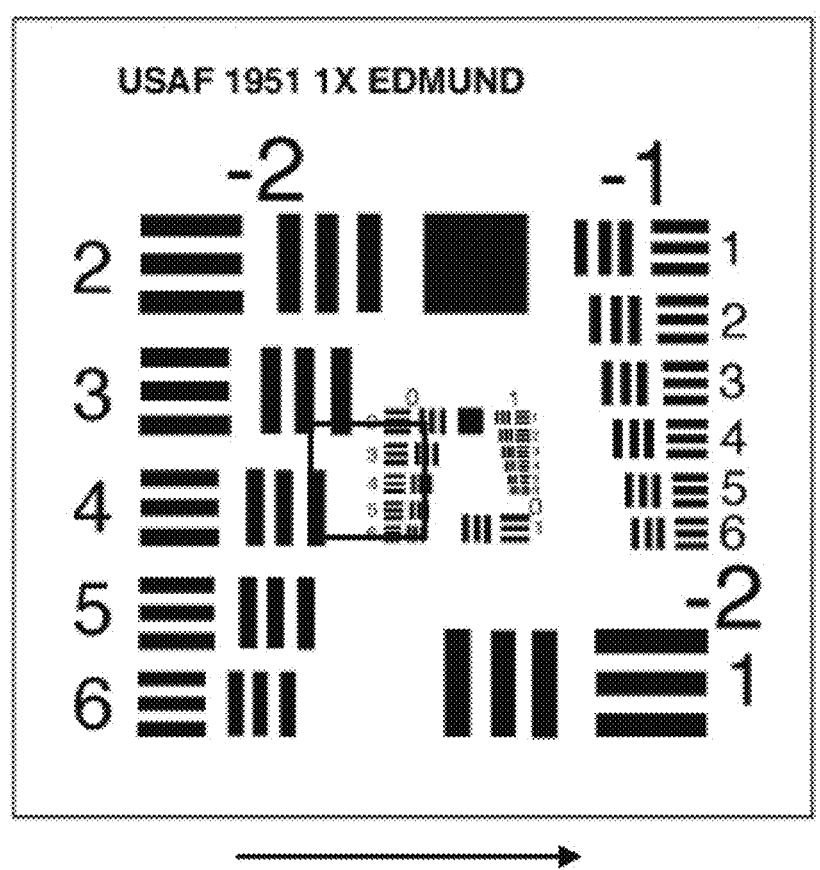
FIG. 17 is a diagram illustrating the object 2 used in a first example.

FIG. 17 is a diagram illustrating the object 2 used in the first example. The object 2 used in the first example is one in which chromium was vapor-deposited on a transparent glass sheet having a thickness of about 1.5 mm, so as to draw the depicted pattern. Black regions in the diagram are light-transmitting regions, while the white region is a light-shielding region where chromium was vapor-deposited. The object 2 was moved in the direction of the depicted arrow at a speed of 100 µm/s by a motorized actuator (LTA-HS manufactured by Newport Corporation).

FIG. 18 is a diagram illustrating data obtained by the first example. Part (a) of the diagram, whose horizontal and vertical axis indicate the time variable t and variable u, respectively, illustrates data of the signal $s_1(u, t)$. Part (b) of the diagram, whose horizontal and vertical axis indicate the frequency and the variable u, respectively, illustrates the amplitude of data obtained by a one-dimensional Fourier transform with respect to the time variable t of the data of the signal $s_1(u, t)$ in the part (a) of the diagram. Part (c) of the diagram, whose horizontal and vertical axis indicate the frequency and the variable u, respectively, illustrates the phase of the data obtained by the one-dimensional Fourier transform with respect to the time variable t of the data of the signal $s_1(u, t)$ in the part (a) of the diagram.

The parts (b) and (c) in the diagram are obtained by the one-dimensional Fourier transform (the above-mentioned expression (13)) with respect to the time variable t of the data of the signal $s_1(u, t)$ illustrated in the part (a) of the diagram. In this example, the difference M between the first and second modulation frequencies is 10 Hz, whereby it is seen in the parts (b) and (c) of the diagram that the Fourier transform image G(u, v) is obtained about the difference signal $\Delta f=10$ Hz acting as the center. This is caused by the modulation term $\exp(i\Delta\omega t)$ in the above-mentioned expression (12).

Figure 20:
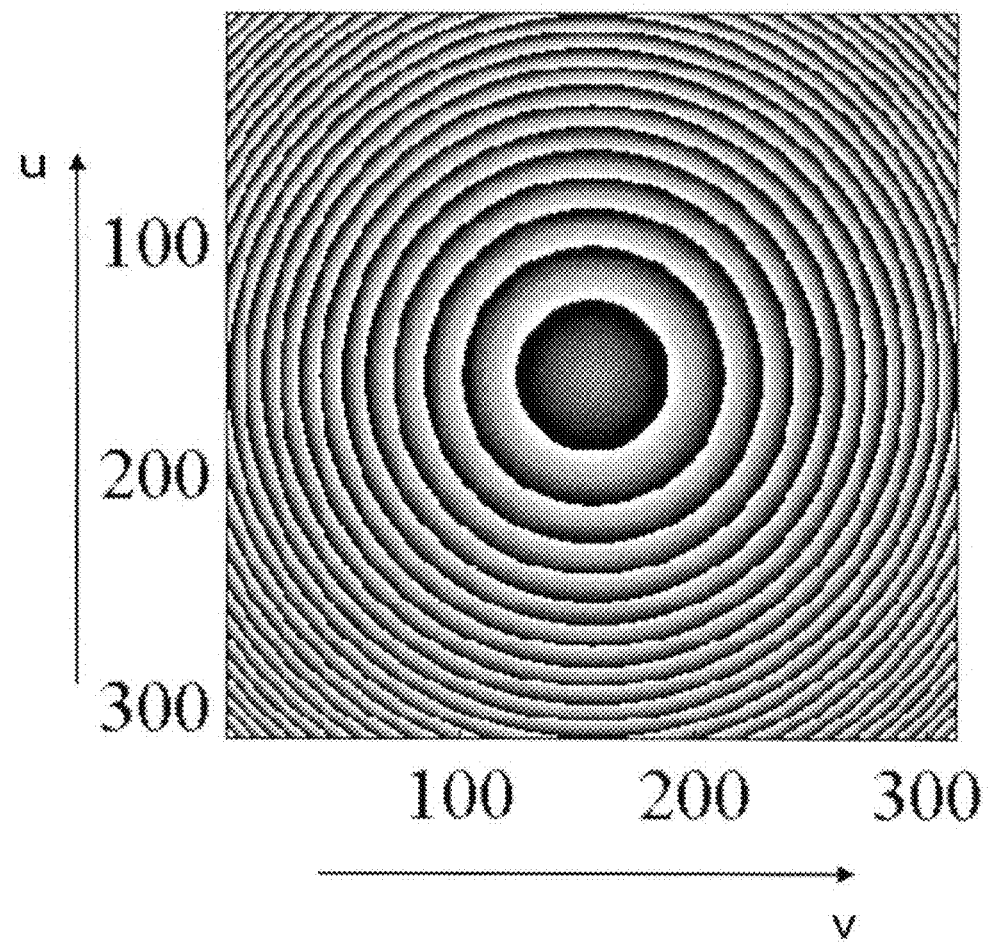
FIG. 20 is a diagram illustrating an initial phase $\phi_O$ in the first example.

FIG. 19 is also a diagram illustrating data obtained by the first example. FIG. 19(a) illustrates amplitude data cutting out a fixed area centered at the difference signal $\Delta f=10$ Hz from the phase data of FIG. 18(b). FIG. 19(b) illustrates phase data cutting out a fixed area centered at the difference signal $\Delta f=10$ Hz from the amplitude data of FIG. 18(c). The fixed area cut out here is a region including the range of a Nyquist frequency $f_{nyq}$ represented by the above-mentioned expression (6) in upper and lower region of the difference frequency $\Delta f$. This cutting operation yields the G(u, v) represented in the following expression (14). The phase data in FIG. 19(b) are those obtained after calibration with the initial phase $\phi_0$ illustrated in FIG. 20. This calibration does not affect the amplitude data in FIG. 19(a).

[Math. 14]

$$G(u, \Delta\omega+\omega_d) \Rightarrow G(u, \omega_d) \quad (14)$$

FIG. 19(c) illustrates the amplitude of data obtained by a two-dimensional Fourier transform of the complex amplitude image G(u, v) represented by the parts (a) and (b) of FIG. 19. FIG. 19(d) illustrates the phase of the data obtained by the two-dimensional Fourier transform of the complex amplitude image G(u, v) represented by the parts (a) and (b) of FIG. 19. As illustrated by the following expression (15), the parts (c) and (d) in FIG. 19 represent the complex amplitude image $g(\xi, \eta)$ of the object 2 obtained by the two-dimensional Fourier transform of the complex amplitude image G(u, v) represented by the parts (a) and (b) of FIG. 19.

[Math. 15]

$$\iint G(u, \omega_d)\exp(i(u\xi+v\eta))dudv = g(\xi, \eta) \quad (15)$$

In the first arrangement example in which the light-receiving surface of the photodetector 46 is arranged on the back focal plane in the first direction of the lens 40, which is also the back focal plane (uv plane) in the second direction of the lens 40 in the structure of the observation device 1 in accordance with this embodiment, the arithmetic unit 50 performs the foregoing arithmetic processing, so as to obtain the image of the object 2. That is, the arithmetic unit 50 acquires data of the signal $s_1(u, t)$ employing the position u on the uv plane and the time t as variables, performs a one-dimensional Fourier transform of the data of the signal $s_1(u, t)$ with respect to the time variable t (the above-mentioned expression (13)), cuts out data in a region including the range of a Nyquist frequency $f_{nyq}$ in upper and lower region of the difference frequency $\Delta f$ from the data obtained by the one-dimensional Fourier transform (the above-mentioned expression (14)), and performs a two-dimensional Fourier transform of thus cut-out data (the above-mentioned expression (15)), thereby yielding the image $g(\xi, \eta)$ of the object 2.

Figure 21:
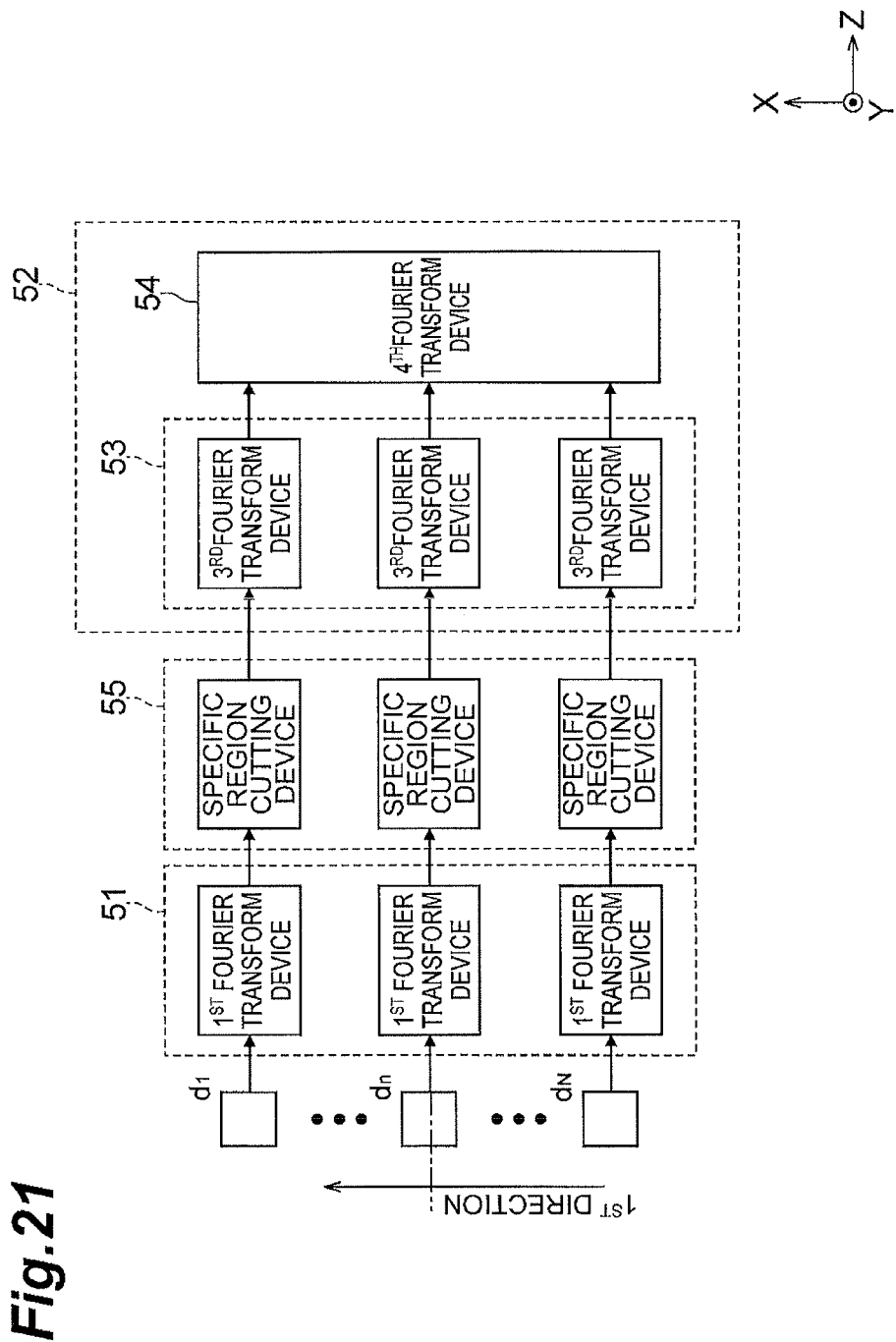
FIG. 21 is a block diagram illustrating structures of the photodetector 46 and an arithmetic unit 50 in the first arrangement example.

FIG. 21 is a diagram illustrating structures of the photodetector 46 and arithmetic unit 50 in the first arrangement example performing the foregoing arithmetic processing. The arithmetic unit 50 comprises a first Fourier transform device 51, a second Fourier transform unit 52, and a specific region cutting device 55. The second Fourier transform unit 52 includes a third Fourier transform device 53 and a fourth Fourier transform device 54. The first Fourier transform device 51 performs a one-dimensional Fourier transform of data of the signal $s_1(u, t)$ employing the position u on the uv plane and the time t as variables with respect to the time variable t (Fourier transform with respect to the time in the above-mentioned expression (13)). The specific region cutting device 55 cuts out data in a region including the range of a Nyquist frequency $f_{nyq}$ in upper and lower region of the difference frequency $\Delta f$ from the data G obtained by the one-dimensional Fourier transform (the above-mentioned expression (14)). The third Fourier transform device 53 performs a one-dimensional Fourier transform of thus cut-out data with respect to the temporal frequency $\omega_d$ (Fourier transform with respect to the temporal frequency $\omega_d$ in the above-mentioned expression (15)). The fourth Fourier transform device 54 performs a Fourier transform with respect to the variable u (Fourier transform with respect to the variable u in the above-mentioned expression (15)). When attention is directed to the Fourier transform units, the first Fourier transform device 51, third Fourier transform device 53, and fourth Fourier transform device 54 are arranged in this order in the arithmetic unit 50 in the first arrangement example. The fourth Fourier transform device 54 is not restricted to the position mentioned above but may be arranged between the first and third Fourier transform devices 51, 53, or in front of the first Fourier transform device 51, for example. Using such arithmetic unit 50, the signal $s_1(u, t)$ is subjected to arithmetic operations, whereby the image $g(\xi, \eta)$ of the object 2 is obtained.

In the first arrangement example, the light-receiving surface of the photodetector 46 is only required to be arranged on a plane equivalent to the back focal plane of the lens 40 and thus may be arranged on a plane within a region which is sufficiently far from the object 2 so that Fraunhofer diffraction can occur.

In the foregoing first arrangement example, a two-dimensional CCD camera is used as the photodetector 46. For obtaining data of the signal $s_1(u, t)$, the photodetector 46 may have a one-dimensional pixel array structure instead of the two-dimensional pixel array structure. Therefore, the observation device 1 of this embodiment can obtain a phase image of the moving object 2 even when using the photodetector 46 having a one-dimensional pixel array structure and exhibiting a slow read-out speed per pixel.

For example, it can obtain a phase image of an object moving rapidly at a speed which is n times that of a two-dimensional detector having m×n pixels in vertical and horizontal directions. It can also be effective in multiple exposure of the object moving within a field of view, thereby improving the SN ratio and enhancing the sensitivity. Cameras (e.g., vision chips and profile sensors) equipped with in-chip arithmetic functions which can directly calculate a modulation frequency of detected light can also be utilized as the photodetector 46. Here, an image corresponding to the modulation frequency can be obtained directly, whereby the image illustrated in FIG. 1 can be displayed in real time. Further, the above-mentioned cameras equipped with the in-chip arithmetic functions can directly output a reconstructed speed image from the detector.

Second Arrangement Example

The second arrangement example will now be explained. In the second arrangement example, the light-receiving surface of the photodetector 46 is arranged on a plane where an image of the object 2 is formed in the first direction by the lens 40, which is also a plane (u'v' plane) where an image of the object 2 is formed in the second direction by the lens 40. As illustrated in FIG. 10, light beams $L_1$ to $L_4$ reaching a point h on the imaging plane (u'v' plane) caused by the lens 40 are emitted from a common virtual point source $g_1$ within the object 2. These light beams $L_1$ to $L_4$ are emitted from the virtual point source $g_1$ at scattering angles $\theta'$ different from each other and thus yield Doppler shift frequencies $f_d$ different from each other.

Figure 22:
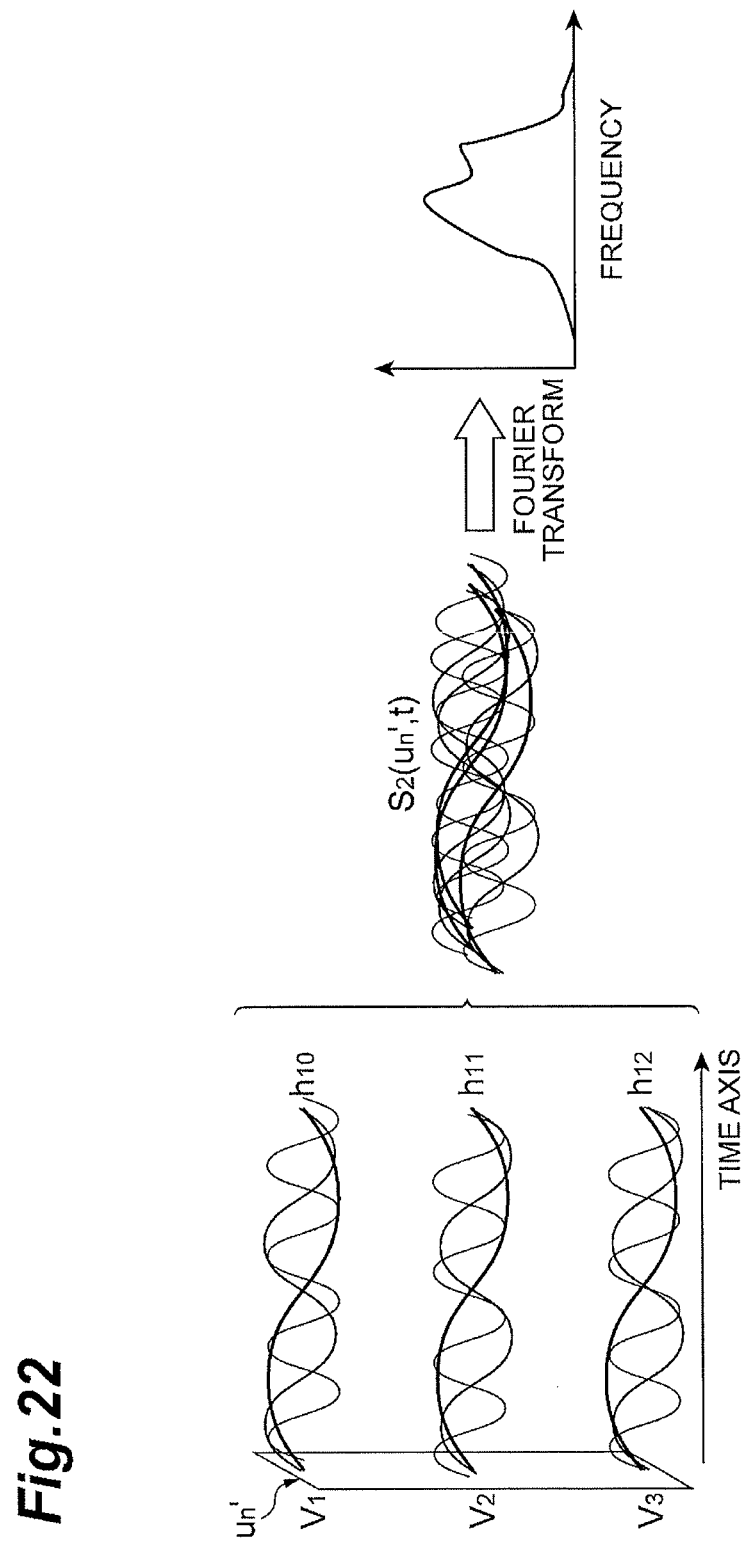
FIG. 22 is a diagram schematically illustrating signals observed on a u'v' plane when employing a second arrangement example in the observation device 1 of this embodiment.

FIG. 22 is a diagram schematically illustrating signals observed on the u'v' plane when employing the second arrangement example in the observation device 1 of this embodiment. In the second arrangement example, scattered light beams having various frequencies are incident on the u'v' plane at each point. Therefore, as illustrated in the left side of the diagram, a beat signal h(u', v') obtained by a heterodyne interference between scattered light and reference light at each point on the u'v' plane includes various frequency components. Let $h_{10}$, $h_{11}$, and $h_{12}$ be respective signals observed at positions $(u'_n, v'_1)$, $(u'_n, v'_2)$, and $(u'_n, v'_3)$ on the u'v' plane. Let $s_2(u'_n, t)$ be a signal representing the sum of signals $h_{10}$ to $h_{12}$ on a line parallel to the v' direction with respect to given $u'_n$ (in the center of the diagram).

As illustrated in the right side of the diagram, a one-dimensional Fourier transform of the signal $s_2(u'_n, t)$ with respect to the time variable t yields a frequency distribution similar to that along the v direction on back focal plane of the lens (uv plane) in the first arrangement example. That is, the one-dimensional Fourier transform of the signal $s_2(u'_n, t)$ with respect to the time variable t converts an irregular frequency distribution on the u'v' plane (on the left in the diagram) into a regular frequency distribution (on the right in the diagram). Since the light-receiving surface of the photodetector 46 is arranged on the imaging plane (u'v' plane) caused by the lens 40, a Fourier transform of the signal $s_2(u'_n, t)$ with respect to the variable u' can yield the same distribution as that on the uv plane. More specifically concerning the u' direction, an optical Fourier transform by a lens 404 in FIG. 23 and an inverse Fourier transform by the arithmetic unit 50 carry out no Fourier transform in the u' direction, whereby a distribution with respect to the u direction in the first arrangement example is obtained.

That is, a two-dimensional Fourier transform image G(u, Δv+v) for a complex amplitude image g(ξ, η) of the object 2 can be obtained by the following expression (16). This Fourier transform. image G(u, Δv+v) is equivalent to that in the first arrangement example, whereby subsequent arithmetic processing similar to that in the first arrangement example can yield the complex amplitude image g(ξ, η) of the object 2.

[Math. 16]

$$\iint s_2(u',t)\exp(i(u'u+\omega t))du'dt = G(u,\Delta\omega+\omega_d) \quad (16)$$

In the second arrangement example in which the light-receiving surface of the photodetector 46 is arranged on a plane where an image of the object 2 is formed in the first direction by the lens 40, which is also a plane (u'v' plane) where an image of the object 2 is formed in the second direction in the structure of the observation device 1 in accordance with this embodiment, the arithmetic unit 50 performs the foregoing arithmetic processing, so as to obtain the image of the object 2. That is, the arithmetic unit 50 acquires data of the signal $s_2(u', t)$ employing the position u' on the u'v' plane and the time t as variables, performs a Fourier transform of the data of the signal $s_2(u', t)$ with respect to the variable u' and the time variable t (the above-mentioned expression (16)), cuts out data in a region including the range of a Nyquist frequency $f_{nyq}$ in upper and lower region of the difference frequency Δf from the data G obtained by the Fourier transform (the above-mentioned expression (14)), and performs a two-dimensional Fourier transform of thus cut-out data (the above-mentioned expression (15)), thereby yielding the image g(ξ, η) of the object 2.

Figure 24:
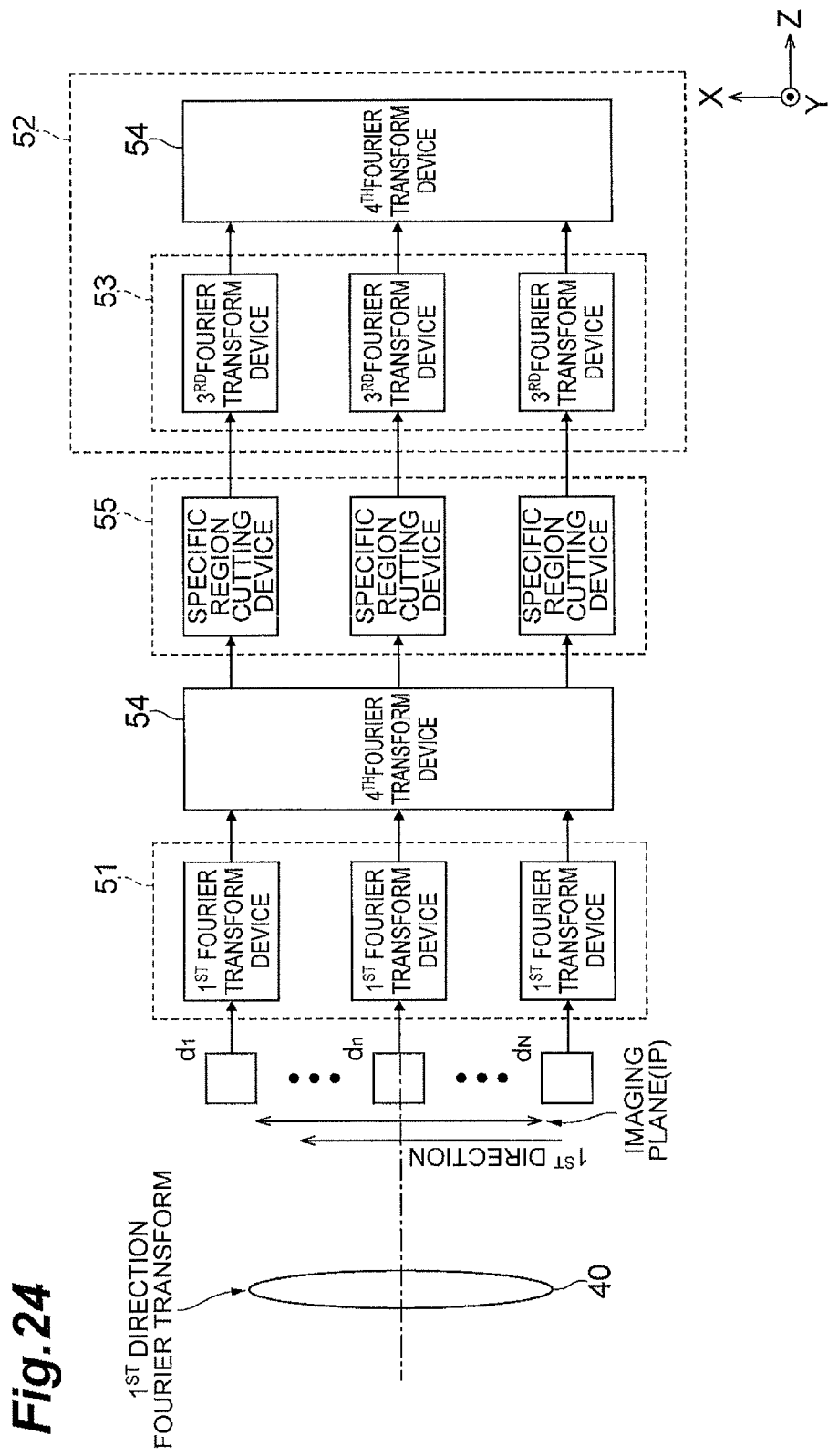
FIG. 24 is a block diagram illustrating structures of the lens 40, photodetector 46, and arithmetic unit 50 in the second arrangement example.

FIG. 24 is a diagram illustrating structures of the lens 40, photodetector 46, and arithmetic unit 50 in the second arrangement example performing the foregoing arithmetic processing. The arithmetic unit 50 comprises a first Fourier transform device 51, a second Fourier transform unit 52, and a specific region cutting device 55. The second Fourier transform unit 52 includes a third Fourier transform device 53 and a fourth Fourier transform device 54. The first Fourier transform device 51 performs a Fourier transform of data of the signal $s_2(u', t)$ employing the position u' on the u'v' plane and the time t as variables, optically Fourier-transformed by the lens 40, with respect to the time variable t (Fourier transform with respect to the time variable t in the above-mentioned expression (16)). The fourth Fourier transform device 54 arranged behind the first Fourier transform device 51 performs a Fourier transform of the data obtained by the preceding Fourier transform with respect to the variable u' (Fourier transform with respect to the variable u' in the above-mentioned expression (16)). The specific region cutting device 55 cuts out data in a region including the range of a Nyquist frequency $f_{nyq}$ in upper and lower region of the difference frequency Δf from the data G obtained by this Fourier transform (the above-mentioned expression (14)). The third Fourier transform device 53 performs a one-dimensional Fourier transform of thus cut-out data with respect to the temporal frequency $\omega_d$ (Fourier transform with respect to the temporal frequency $\omega_d$ in the above-mentioned expression (15)). The fourth Fourier transform device 54 arranged behind the third Fourier transform device 53 performs a Fourier transform with respect to the variable u (Fourier transform with respect to the variable u in the above-mentioned expression (15)). When attention is directed to the Fourier transform units, the first Fourier transform device 51, fourth Fourier transform device 54, third Fourier transform device 53, and fourth Fourier transform device 54 are arranged in this order in the arithmetic unit 50 in the second arrangement example. The fourth Fourier transform device 54 arranged behind the first Fourier transform device 51 is not restricted to this position but may be arranged between the third Fourier transform device 53 and the fourth Fourier transform device 54 arranged behind the third Fourier transform device 53, or in front of the first Fourier transform device 51, for example. The fourth Fourier transform device 54 arranged behind the third Fourier transform device 53 is not restricted to this position but may be arranged between the fourth Fourier transform device 54 arranged behind the first Fourier transform device 51 and the third Fourier transform device 53, or in front of the first Fourier transform device 51, for example. Using such arithmetic unit 50, the signal $s_2(u', t)$ is subjected to arithmetic operations, whereby the image g(ξ, η) of the object 2 is obtained.

Figure 23:
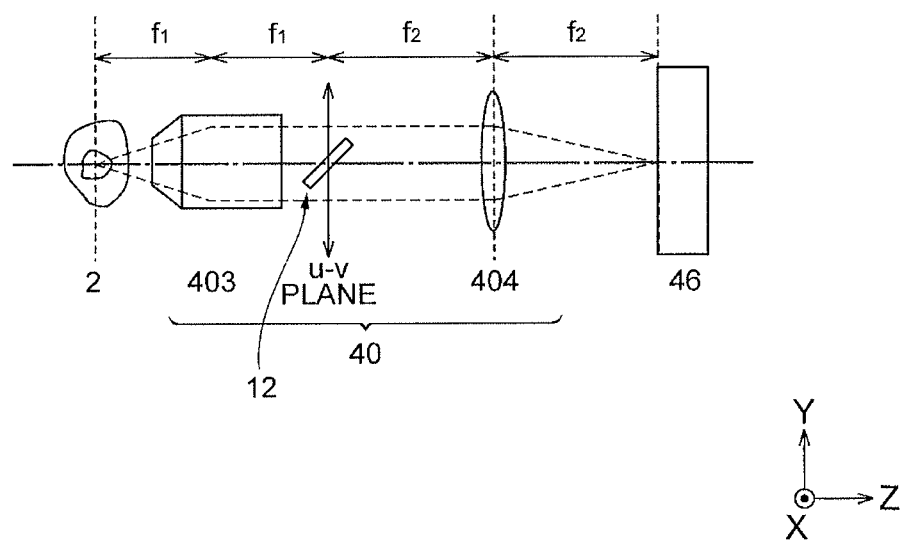
FIG. 23 is a diagram illustrating a structural example of the lens 40 in the second arrangement example.

An example (second example) in the second arrangement example will now be explained. In the second example, as the lens 40, one having a structure including an objective lens 403 (having a focal length $f_1$) and a lens 404 (whose focal length $f_2$=50 mm) as illustrated in FIG. 23 was used, while an image of the object 2 was formed on the light-receiving surface of the photodetector 46 by these two lenses 403, 404. As illustrated in FIG. 23, the beam splitter 12 was arranged between the lenses 403, 404. The beam splitter 12 was arranged on the back focal plane of the lens 403 constituting the lens 40 such as to split the substantially zero-order light in two. The light reflected by the beam splitter 12 was fed to the lens 60 as the second light.

Figure 25:
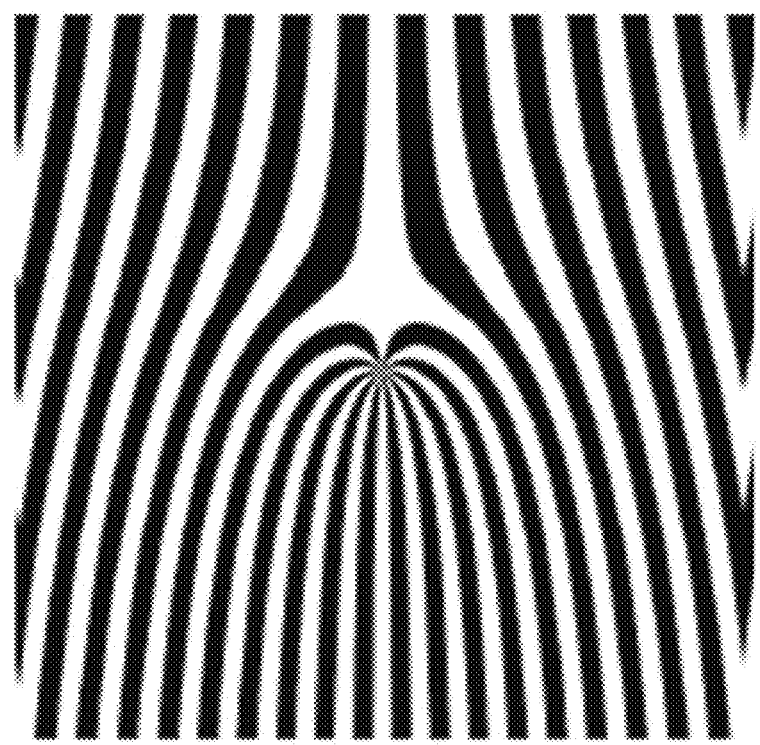
FIG. 25 is a diagram illustrating the object 2 used in a second example.

FIG. 25 is a diagram illustrating the object 2 used in the second example. The object 2 used in the second example was one in which the depicted pattern was drawn on a flat sheet made of PMMA. Depicted black regions were formed as depressions having a thickness of 633 nm±25 nm with respect to white regions. The size of the object 2 shown in FIG. 25 is 5 mm (L)×5 mm (W). The other conditions are the same as those in the first example.

Figure 26:
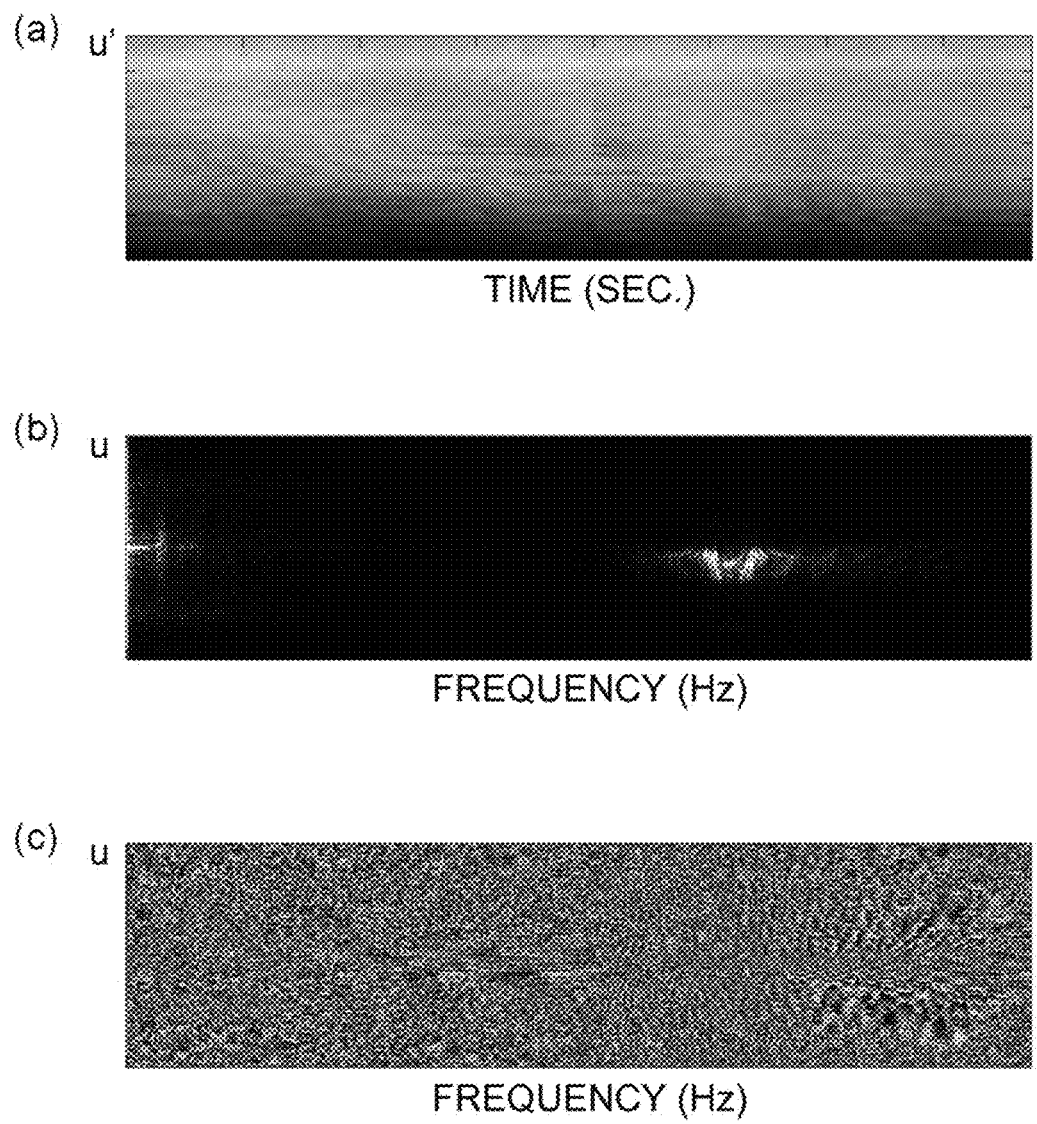
FIG. 26 is a diagram illustrating data obtained by the second example.

FIG. 26 is a diagram illustrating data obtained by the second example. Part (a) of the diagram, whose horizontal axis and vertical axis indicate the time variable t and variable u', respectively, illustrates data of the signal $s_2(u', t)$. Part (b) of the diagram, whose horizontal axis and vertical axis indicate the frequency and the variable u, respectively, illustrates the amplitude of data obtained by a Fourier transform with respect to the variable u' and time variable t of the data of the signal $s_2(u', t)$ in the part (a) of the diagram. Part (c) of the diagram, whose horizontal axis and vertical axis indicate the frequency and the variable u, respectively, illustrates the phase of the data obtained by the Fourier transform with respect to the variable u' and time variable t of the data of the signal $s_2(u', t)$ in the part (a) of the diagram.

The parts (b) and (c) in the diagram were obtained by the Fourier transform (the above-mentioned expression (16)) with respect to the variable u' and time variable t of the data of the signal $s_2(u', t)$ illustrated in the part (a) of the diagram. In this example, the difference $\Delta f$ between the first and second modulation frequencies was also 10 Hz, whereby it is seen in the parts (b) and (c) of the diagram that the Fourier transform image G(u, v) was obtained about the difference signal $\Delta f=10$ Hz acting as the center.

Figure 27:
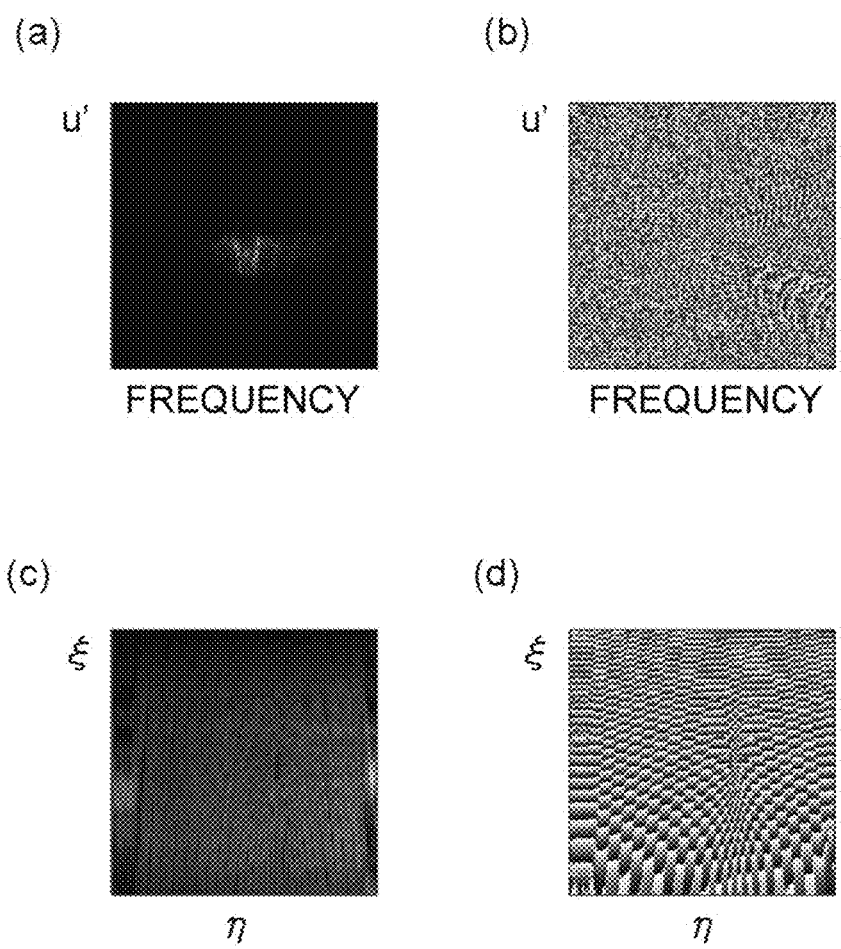
FIG. 27 is a diagram illustrating data obtained by the second example.

FIG. 27 is also a diagram illustrating data obtained by the second example. FIG. 27(a) illustrates amplitude data cutting out a fixed area centered at the difference signal $\Delta f=10$ Hz from the amplitude data of FIG. 26(b). FIG. 27(b) illustrates phase data cutting out a fixed area centered at the difference signal $\Delta f=10$ Hz from the phase data of FIG. 26(c). The fixed area cut out here is a region including the range of a Nyquist frequency $f_{nyq}$ represented by the above-mentioned expression (6) in upper and lower region of the difference frequency $\Delta f$.

The phase data in FIG. 27(b) are those calibrated with (subtracting) the initial phase $\phi'_0$. In the second arrangement example, the u' direction of $s_2(u', t)$ is an imaging direction, whereby the initial phase may be zero or a uniform distribution in the u' direction. In the v' direction, on the other hand, the data are calibrated with the initial phase under optical conditions of reference light and scattered light.

FIG. 27(c) illustrates the amplitude of data obtained by a two-dimensional Fourier transform of the complex amplitude image G(u, v) represented by the parts (a) and (b) of FIG. 27. FIG. 27(d) illustrates the phase of the data obtained by the two-dimensional Fourier transform of the complex amplitude image G(u, v) represented by the parts (a) and (b) of FIG. 27. The parts (c) and (d) in FIG. 27 represent the complex amplitude image $g(\xi, \eta)$ of the object 2 obtained by the two-dimensional Fourier transform of the complex amplitude image G(u, v) represented by the parts (a) and (b) of FIG. 27.

Third Arrangement Example

Figure 28:
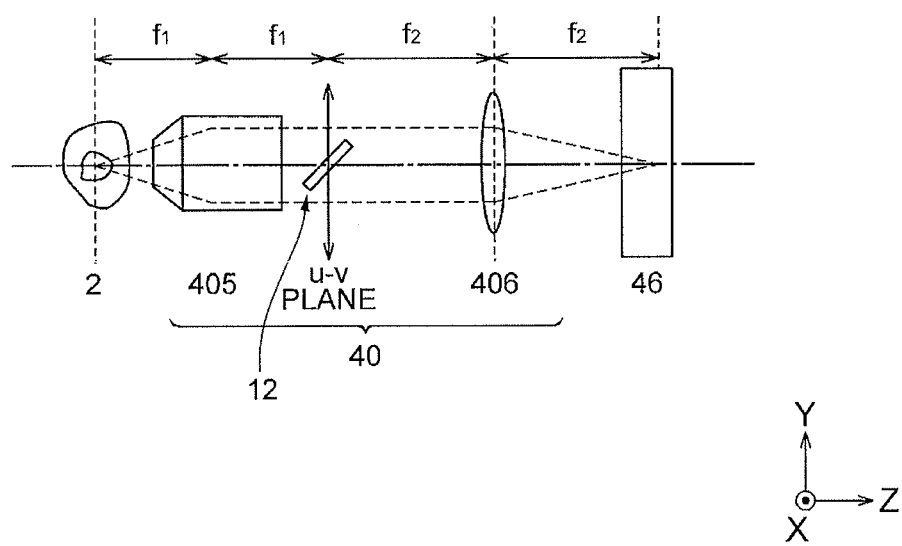
FIG. 28 is a diagram illustrating a structural example of the lens 40 in a third arrangement example.

The third arrangement example will now be explained. The third arrangement example uses the lens structure illustrated in FIG. 28. In the third arrangement example, as illustrated in FIG. 28, the beam splitter 12 is arranged on the back focal plane of a lens 405 so as to split the substantially zero-order light in two. The light reflected by the beam splitter 12 is fed to the lens 60 as the second light. In the third arrangement example, the light-receiving surface of the photodetector 46 is arranged on a u"v" plane which is a given plane perpendicular to the optical axis in front or rear of the lens 40 in both of the first and second directions. The u"v" plane is treated as a Fresnel diffraction plane. A Fresnel diffraction image g"(u", v") of the complex amplitude image $g(\xi, \eta)$ of the object 2 is represented by the following expression (17). The following expression (18) represents h in the expression (17). H is a Fourier transform of h. G is a Fourier transform of the complex amplitude image $g(\xi, \eta)$ of the object 2. $FT^{-1}$ is a sign representing an arithmetic operation of a two-dimensional inverse Fourier transform. The variable z in the expression is the gap (distance) between the $\xi\eta$ and u"v" planes. Here, k is the wave number, and $\lambda$ is the wavelength.

[Math. 17]

$$g''(u'', v'') = \int\int g(\xi, \eta)h(u'' - \xi, v'' - \eta)d\xi d\eta \qquad (17)$$
$$= FT^{-1}[G \cdot H]$$

[Math. 18]

$$h(u, v) = \frac{e^{ikz}}{i\lambda z}\exp\left[\frac{ik}{2z}(u^2 + v^2)\right] \qquad (18)$$

The expression (17) means that an inverse Fourier transform of the product of G(u, v) on the uv plane and H(u, v), equivalent to the image g"(u", v"), appears on the u"v" plane. In other words, the expression (17) means that a Fourier transform of the image g"(u", v") appearing on the u"v" plane yields the product of G and H.

Therefore, letting $s_3(u'', t)$ be a signal representing the sum of signals on a line parallel to the v" direction with respect to given $u''_n$ on the u"v" plane, a Fourier transform of data of the signal $s_3(u'', t)$ with respect to the variable u" and time variable t yields the product of G(u, v) on the uv plane and H(u) as illustrated in the following expression (19).

Here, H(u) represents a function which is uniform in the v direction in functions H obtained by a two-dimensional Fourier transform of the expression (18). More specifically concerning the u" direction, the Fourier transform with respect to the variable u" by the arithmetic unit 50 has the same effect as that of the optical Fourier transform arranging the lens 40 in FIG. 1, thereby yielding a distribution represented by d≠f in the expression (10). In the v" direction, on the other hand, the same distribution as with v in the first arrangement example is obtained because of the reason mentioned above.

[Math. 19]

$$\iint s_3(u'',t)\exp(i(u''u+\omega t))du''dt = G(u,\Delta\omega+\omega_d)\cdot H(u) \qquad (19)$$

For obtaining G(u, v) on the uv plane, the above-mentioned expression (19) is divided by H(u) as in the following expression (20). Subsequent arithmetic processing equivalent to that in the first arrangement example can yield the complex amplitude image $g(\xi, \eta)$ of the object 2.

[Math. 20]

$$G(u, \Delta\omega + \omega_d) = \frac{1}{H(u)}\int\int s_3(u'', t)\exp(i(u''u + \omega t))du''dt \qquad (20)$$

In the third arrangement example in which the light-receiving surface of the photodetector 46 is arranged on a given u"v" plane perpendicular to the optical axis in front or rear of the lens 40 in the structure of the observation device 1 in accordance with this embodiment, the arithmetic unit 50 performs the foregoing arithmetic processing, so as to obtain the image of the object 2. That is, the arithmetic unit 50 acquires data of the signal $s_3(u'', t)$ employing the position u" on the u"v" plane and the time t as variables, performs a Fourier transform of the data of the signal $s_3(u'', t)$ with respect to the variable u" and time variable t (the above-mentioned expression (19)), divides the data obtained by the Fourier transform by H, so as to yield G on the uv plane (the above-mentioned expression (20)), cuts out data in a region including the range of a Nyquist frequency $f_{nyq}$ in upper and lower region of the difference frequency Δf from thus obtained data G (the above-mentioned expression (14)), and performs a two-dimensional Fourier transform of thus cut-out data (the above-mentioned expression (15)), thereby yielding the image $g(\xi, \eta)$ of the object 2. For obtaining the complex amplitude image $g(\xi, \eta)$ in focus, the initial phase resulting from optical conditions of scattered light and reference light must be corrected as appropriate.

Figure 29:
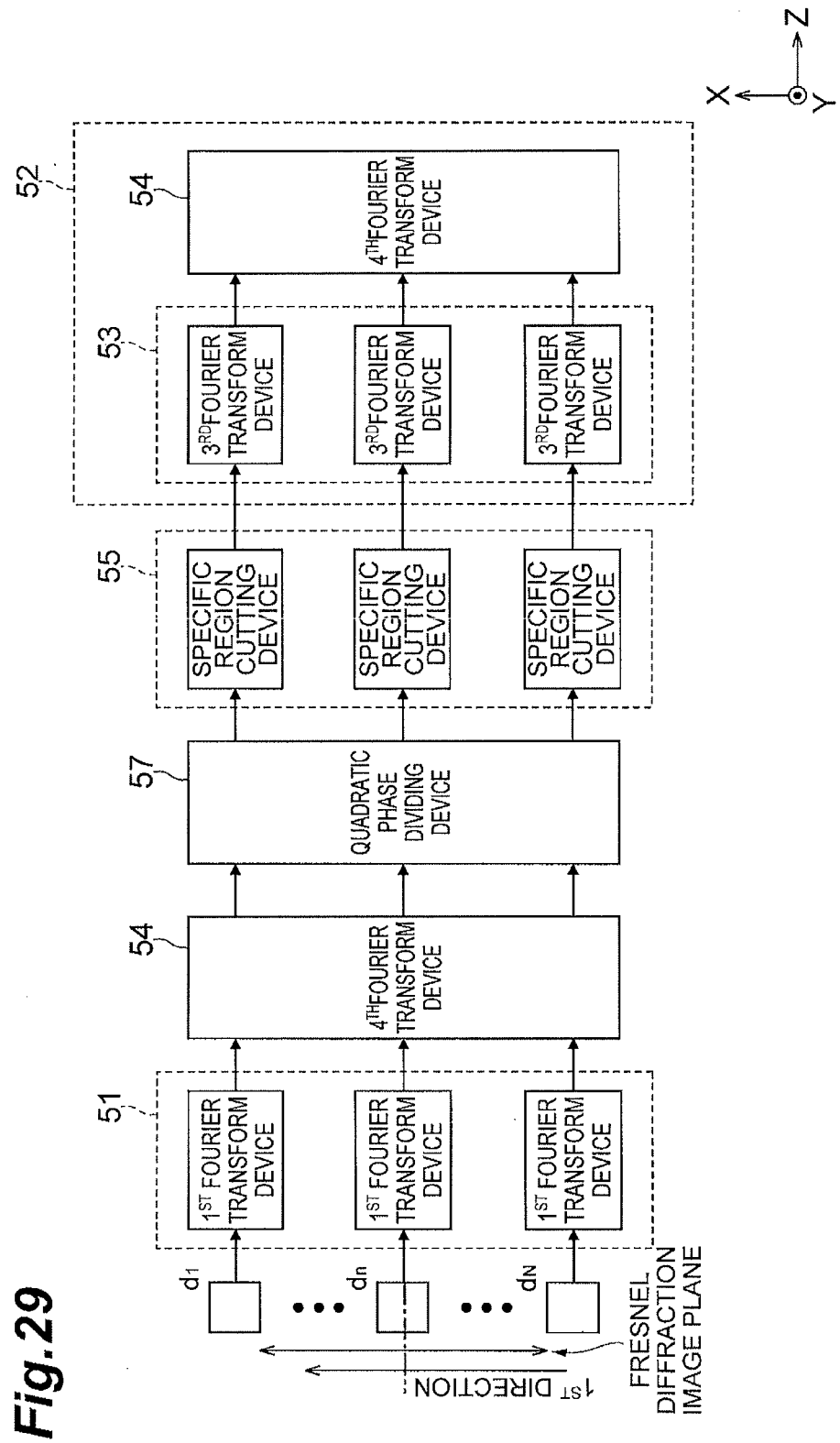
FIG. 29 is a block diagram illustrating structures of the photodetector 46 and arithmetic unit 50 in the third arrangement example.

FIG. 29 is a diagram illustrating structures of the photodetector 46 and arithmetic unit 50 in the third arrangement example performing the foregoing arithmetic processing. The arithmetic unit 50 comprises a first Fourier transform device 51, a second Fourier transform unit 52, a specific region cutting device 55, and a quadratic phase dividing device 57. The second Fourier transform unit 52 includes a third Fourier transform device 53 and a fourth Fourier transform device 54. The first Fourier transform device 51 performs a Fourier transform of the data of the signal $s_3(u'', t)$ employing the position u" on the u"v" plane and the time t as variables with respect to the time variable t (Fourier transform with respect to the time variable t in the above-mentioned expression (19)). The fourth Fourier transform device 54 arranged behind the first Fourier transform device 51 performs a Fourier transform with respect to the variable u" of the data obtained by the preceding Fourier transform (Fourier transform with respect to the variable u" in the above-mentioned expression (19)). The quadratic phase dividing device 57 divides the data obtained by the fourth Fourier transform device 54 by H, so as to yield G on the uv plane (the above-mentioned expression (20)). The specific region cutting device 55 cuts out data in a region including the range of a Nyquist frequency $f_{nyq}$ in upper and lower region of the difference frequency Δf from thus obtained data G (the above-mentioned expression (14)). The third Fourier transform device 53 performs a one-dimensional Fourier transform of thus cut-out data with respect to the temporal frequency $\omega_d$ (Fourier transform with respect to the temporal frequency $\omega_d$ in the above-mentioned expression (15)). The fourth Fourier transform device 54 arranged behind the third Fourier transform device 53 performs a Fourier transform with respect to the variable u (Fourier transform with respect to the variable u in the above-mentioned expression (15)). When attention is directed to the Fourier transform units, the first Fourier transform device 51, fourth Fourier transform device 54, third Fourier transform device 53, and fourth Fourier transform device 54 are arranged in this order in the arithmetic unit 50 in the third arrangement example. The fourth Fourier transform device 54 arranged behind the first Fourier transform device 51 is not restricted to this position but may be arranged between the third Fourier transform device 53 and the fourth Fourier transform device 54 arranged behind the third Fourier transform device 53, or in front of the first Fourier transform device 51, for example. The fourth Fourier transform device 54 arranged behind the third Fourier transform device 53 is not restricted to this position but may be arranged between the fourth Fourier transform device 54 arranged behind the first Fourier transform device 51 and the third Fourier transform device 53, or in front of the first Fourier transform device 51, for example. Using such arithmetic unit 50, the signal $s_3(u'', t)$ is subjected to arithmetic operations, whereby the image $g(\xi, \eta)$ of the object 2 is obtained.

A special case of the third arrangement example corresponds to the first or second arrangement example. That is, the second arrangement example corresponds to a case where H(u, v)=1 in the expression (17) in the third arrangement example. The first arrangement example corresponds to a case where the Fourier plane (Fraunhofer diffraction) is on the u"v" plane in the third arrangement example. The latter will be explained in the following.

Substituting the expression (18) into the expression (17) and expanding it yields the following expression (21). Letting z be infinity in the expression (21), the value of the exponential function within the integral in the right side is approximated by 1, whereby the expression (21) is approximated by the following expression (22). The expression (22) is equivalent to the expression (10). Therefore, a special case of the third arrangement example, i.e., a case where d=f in the expression (10), is the first arrangement example.

[Math. 21]

$$g''(u'', v'') = \frac{e^{ikz}}{i\lambda z} e^{i\frac{k}{2z}(u''^2+v''^2)} \int\int \left\{ g(\xi, \eta) e^{i\frac{k}{2z}(\xi^2+\eta^2)} \right\} e^{-i\frac{2\pi}{\lambda z}(u''\xi+v''\eta)} d\xi d\eta \quad (21)$$

[Math. 22]

$$g''(u'', v'') = \frac{e^{ikz}}{i\lambda z} e^{i\frac{k}{2z}(u''^2+v''^2)} \int\int g(\xi, \eta) e^{-i\frac{2\pi}{\lambda z}(u''\xi+v''\eta)} d\xi d\eta \quad (22)$$

Fourth Arrangement Example

In the foregoing first, second, and third arrangement examples, details of arithmetic operations have been explained while omitting the initial phase $\phi_0$ resulting from optical conditions of scattered light and reference light. A structure in which, as in the first arrangement example, the arithmetic unit 50 corrects the initial phase $\phi_0$ included in a one-dimensional Fourier transform with respect to a time variable in the observation device 1 in which the light-receiving surface of the photodetector 46 is arranged on the back focal plane in the first direction of the lens 40, which is also the back focal plane in the second direction of the lens 40, will now be explained in detail as a fourth arrangement example. The lens 40 in the fourth arrangement example has a lens structure similar to that of the lens 40 in the first arrangement example illustrated in FIG. 12.

Figure 30:
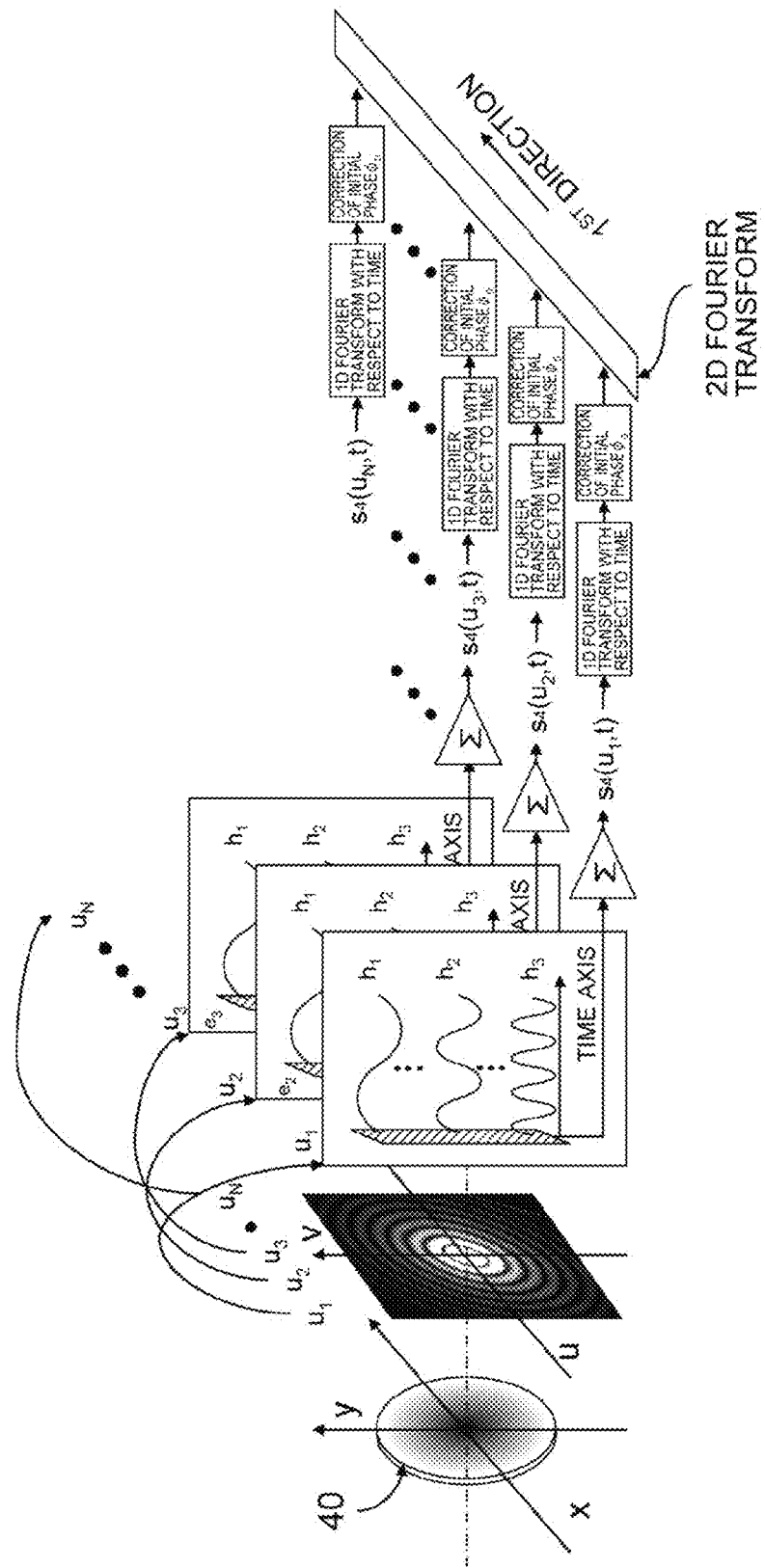
FIG. 30 is a schematic diagram of arithmetic operations performed by the arithmetic unit 50 in a fourth arrangement example.

FIG. 30 is a diagram schematically illustrating an operation for obtaining a signal $s_4(u_n, t)$ representing the sum of signals $h_1$ to $h_N$ on a line parallel to the v direction for each $u_n$ when the fourth arrangement example is employed in the observation device 1 of this embodiment. In FIG. 30, sign Σ represents an arithmetic operation for summing of signals $h_1$ to $h_N$. The signal $s_4(u, t)$ indicating the sum of signals h(v) on a line parallel to the v direction with respect to a given u-coordinate value is calculated as with $s_1$ represented by the expression (11).

When taking account of the initial phase $\phi_0$, which is omitted for yielding the expression (13) in the first arrangement example, a one-dimensional Fourier transform of the signal $s_4(u, t)$ employing the position u on the uv plane and the time t as variables with respect to the time variable t is performed by an arithmetic operation represented by the following expression (23) similar to that for $s_1(u, t)$.

[Math. 23]

$$\int s_4(u,t)\exp(-\omega t)dt = aG(u,\Delta v+v)\exp(i\phi_0) \quad (23)$$

When the left side of the expression (23) is represented as $S_4(u, \Delta v+v)$, multiplying both sides of the expression (23) by the term $\exp(-\phi_0)$ including the initial phase $\phi_0$ leaves the constant of proportionality a and function G alone in the right side of the expression (23) as with the right side of the expression (13). That is, the correction of the initial phase $\phi_0$ is equivalent to multiplying the signal $S_4(u, \Delta v+v)$ by $\exp(-i\phi_0)$.

Thus, multiplying the signal $S_4(u, \Delta v+v)$ by $\exp(-i\phi_0)$ can yield a two-dimensional Fourier transform image $G(u, \Delta v+v)$ for the complex amplitude image $g(\xi, \eta)$ of the object 2. This Fourier transform image $G(u, \Delta v+v)$ is equivalent to that in the first arrangement example, whereby subsequent arithmetic processing similar to that in the first arrangement example can yield the complex amplitude image $g(\xi, \eta)$ of the object 2.

In the fourth arrangement example in which the light-receiving surface of the photodetector 46 is arranged on the back focal plane (uv plane) of the lens 40 in the structure of the observation device 1 in accordance with this embodiment, the arithmetic unit 50 performs the foregoing arithmetic processing, so as to obtain the image of the object 2. That is, the arithmetic unit 50 acquires data of the signal $s_4(u, t)$ employing the position u on the uv plane and the time t as variables, performs a one-dimensional Fourier transform of the data of the signal $s_4(u, t)$ with respect to the time variable t (the above-mentioned expression (23)), corrects the data obtained by the one-dimensional Fourier transform with the initial phase $\phi_0$, cuts out data in a region including the range of a Nyquist frequency $f_{nyq}$ in upper and lower region of the difference frequency $\Delta f$ from thus corrected data G (the above-mentioned expression (14)), and performs a two-dimensional Fourier transform of thus cut-out data (the above-mentioned expression (15)), thereby yielding the image $g(\xi, \eta)$ of the object 2.

Figure 31:
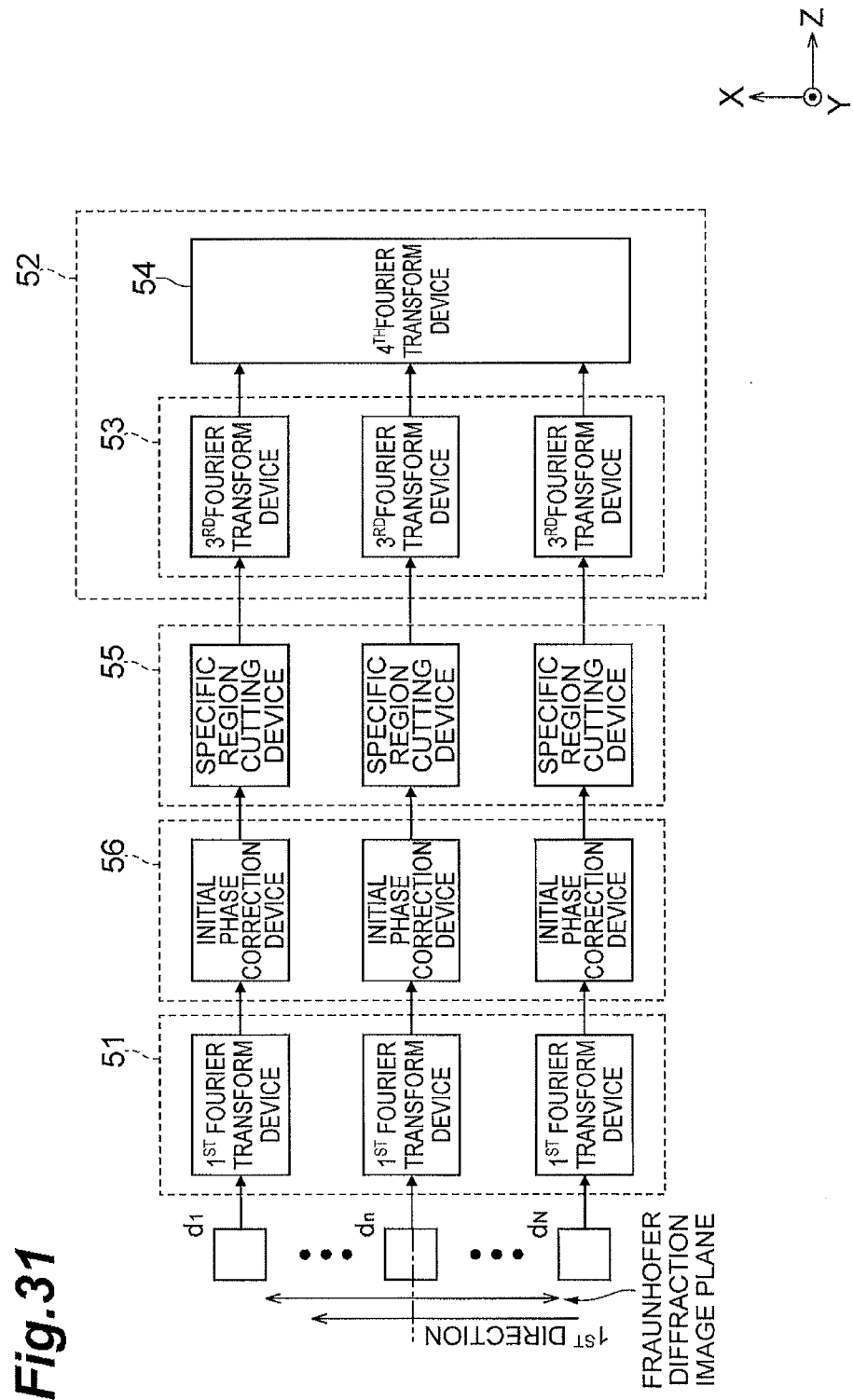
FIG. 31 is a block diagram illustrating structures of the photodetector 46 and arithmetic unit 50 in the fourth arrangement example.

FIG. 31 is a diagram illustrating the structure of the arithmetic unit 50 in the fourth arrangement example performing the foregoing arithmetic processing. The arithmetic unit 50 comprises a first Fourier transform device 51 for performing a one-dimensional Fourier transform of data of the signal $s_4(u, t)$ employing the position u on the uv plane and the time t as variables with respect to the time variable t (the above-mentioned expression (23)), an initial phase correction device 56 for correcting the data obtained by the one-dimensional Fourier transform with the initial phase $\phi_0$, a specific region cutting device 55 for cutting out data in a region including the range of a Nyquist frequency $f_{nyq}$ in upper and lower region of the difference frequency $\Delta f$ from thus corrected data G (the above-mentioned expression (14)), a third Fourier transform device 53 for performing a one-dimensional Fourier transform of thus cut-out data with respect to the temporal frequency $\omega_d$ (Fourier transform with respect to the temporal frequency $\omega_d$ in the above-mentioned expression (15)), and a fourth Fourier transform device 54 for performing a Fourier transform with respect to the variable u (Fourier transform with respect to the variable u in the above-mentioned expression (15)). When attention is directed to the Fourier transform units, the first Fourier transform device 51, third Fourier transform device 53, and fourth Fourier transform device 54 are arranged in this order in the arithmetic unit 50 in the fourth arrangement example. The fourth Fourier transform device 54 is not restricted to this position but may be arranged between the first Fourier transform device 51 and the third Fourier transform device 53, or in front of the first Fourier transform device 51, for example. Using such arithmetic unit 50, the signal $s_1(u, t)$ is subjected to arithmetic operations, whereby the image $g(\xi, \eta)$ of the object 2 is obtained.

As illustrated in the fourth arrangement example, correcting the initial phase $\phi_0$ resulting from optical conditions of reference light and scattered light can prevent the complex amplitude image $g(\xi, \eta)$ of the object 2 from being blurred by the initial phase $\phi_0$, whereby the complex amplitude image $g(\xi, \eta)$ in focus can be obtained. Though processing for correcting the initial phase $\phi_0$ has been explained in the arrangement examples in which the light-receiving surface of the photodetector 46 is arranged so as to coincide with the back focal plane of the lens 40 by way of example, the initial phase $\phi_0$ can be corrected by similar arithmetic operations in other arrangement examples as well. While all the following arrangement examples illustrate those in which the initial phase $\phi_0$ is corrected, the processing for correcting the initial phase $\phi_0$ is not always necessary.

Fifth Arrangement Example

In the second arrangement example explained above, the first Fourier transform device 51, fourth Fourier transform device 54, third Fourier transform device 53, and fourth Fourier transform device 54 are arranged in this order in the arithmetic unit 50. A structure in which, as in the second arrangement example, the arithmetic unit 50 is simplified in the observation device 1 in which the light-receiving surface of the photodetector 46 is arranged on a plane where an image of an object is formed in the first direction by the lens 40, which is also a plane (u'v' plane) on which the image of the object is formed in the second direction, will now be explained as the fifth arrangement example as compared with the second arrangement example. The lens 40 in the fifth example has a lens structure similar to that in the second arrangement example illustrated in FIG. 23.

The uv plane in FIG. 23 illustrates the back focal plane of the lens 403. In the second arrangement example, the light-receiving surface of the photodetector 46 is arranged on the back focal plane of the lens 404 having the front focal plane on the uv plane. In FIG. 23, X is the first direction and coincides with u'. Y is the second direction and coincides with v'. Z is a direction orthogonal to the first and second directions. The lenses 403, 404, each of which is a spherical lens, exhibit the same action in the X and Y directions. Since the X and Y directions are orthogonal to each other, Fourier transforms in the X and Y directions have no influences on each other and pose no problems mathematically even when considered independently from each other.

In FIG. 23, the action of the lens 404 in the second arrangement example is equivalent to optically performing respective one-dimensional Fourier transforms of an image appearing on the uv plane with respect to the variables u and v. The arithmetic unit 50 in the second arrangement example performs a first two-dimensional Fourier transform of the signal $s_2(u', t)$ by the expression (16), thereby yielding $G(u, \Delta\omega+\omega_d)$. The first two-dimensional Fourier transform is equivalent to performing respective one-dimensional Fourier transforms with respect to the time variable t and the variable u'.

The arithmetic unit 50 in the second arrangement example performs a second two-dimensional inverse Fourier transform of a distribution $G(u, \omega_d)$ cutting out a frequency region including the range of a Nyquist frequency $f_{nyq}$ in upper and lower region of the difference frequency $\Delta\omega$ acting as the center frequency from the data $G(u, \Delta\omega+\omega_d)$, so as to yield $g(u', t)$. The second two-dimensional Fourier transform is equivalent to performing respective one-dimensional Fourier transforms with respect to the temporal frequency $\omega_d$ and the variable u. That is, the arithmetic unit 50 in the second arrangement example performs the one-dimensional Fourier transform with respect to the variable u' in the first two-dimensional Fourier transform and the one-dimensional Fourier transform with respect to the variable u in the second two-dimensional Fourier transform, thereby doing no Fourier transform in the u' direction. Therefore, it can be said that redundancy in Fourier transforms exists in the u direction or u' direction (first direction) in the arithmetic unit 50 for receiving the output of the photodetector 46 in the second arrangement example.

Figure 32:
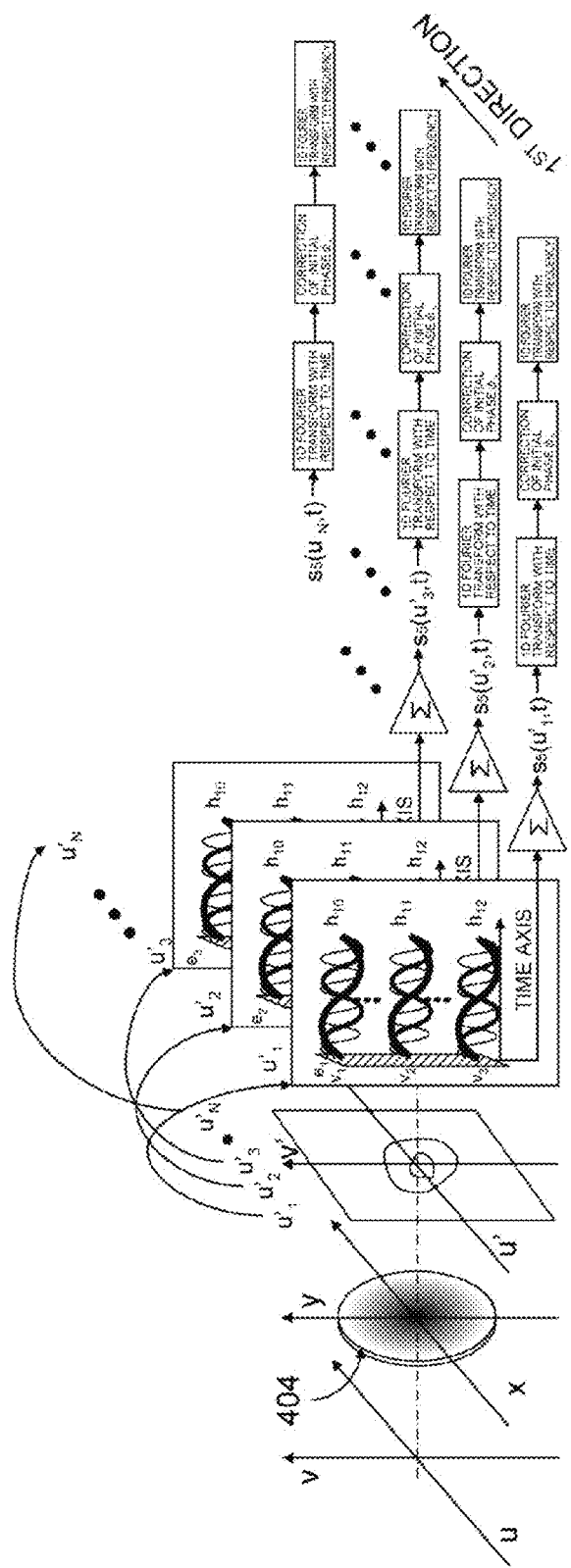
FIG. 32 is a schematic diagram of arithmetic operations performed by the arithmetic unit 50 in a fifth arrangement example.

FIG. 32 illustrates a schematic diagram of arithmetic operations performed by the arithmetic unit 50 in the fifth arrangement example reducing the number of Fourier transforms by simplifying the second arrangement example. In the fifth arrangement example in which the light-receiving surface of the photodetector 46 is arranged on a plane where an image of the object 2 is formed in the first direction by the lens 404, which is also a plane (u'v' plane) where an image of the object 2 is formed in the second direction in the observation device 1, the arithmetic unit 50 performs the following arithmetic processing, so as to obtain the image of the object 2. That is, the lens 404 constituting the lens 40 optically performs a Fourier transform in the first direction. The arithmetic unit 50 acquires data of the signal $s_5(u', t)$ employing the position u' on the uv plane and the time t as variables and performs a one-dimensional Fourier transform of the data of the signal $s_5(u', t)$ with respect to the time variable t (the above-mentioned expression (23)). It corrects the data obtained by the one-dimensional Fourier transform with the initial phase $\phi_0$ and cuts out data in a region including the range of a Nyquist frequency $f_{nyq}$ in upper and lower region of the difference frequency $\Delta f$ from thus corrected data G (the above-mentioned expression (14)). It performs a one-dimensional Fourier transform of thus cut-out data with respect to the temporal frequency $\omega_d$ (Fourier transform with respect to the temporal frequency $\omega_d$ in the above-mentioned expression (15)), thereby yielding the image $g(\xi, \eta)$ of the object 2.

Figure 33:
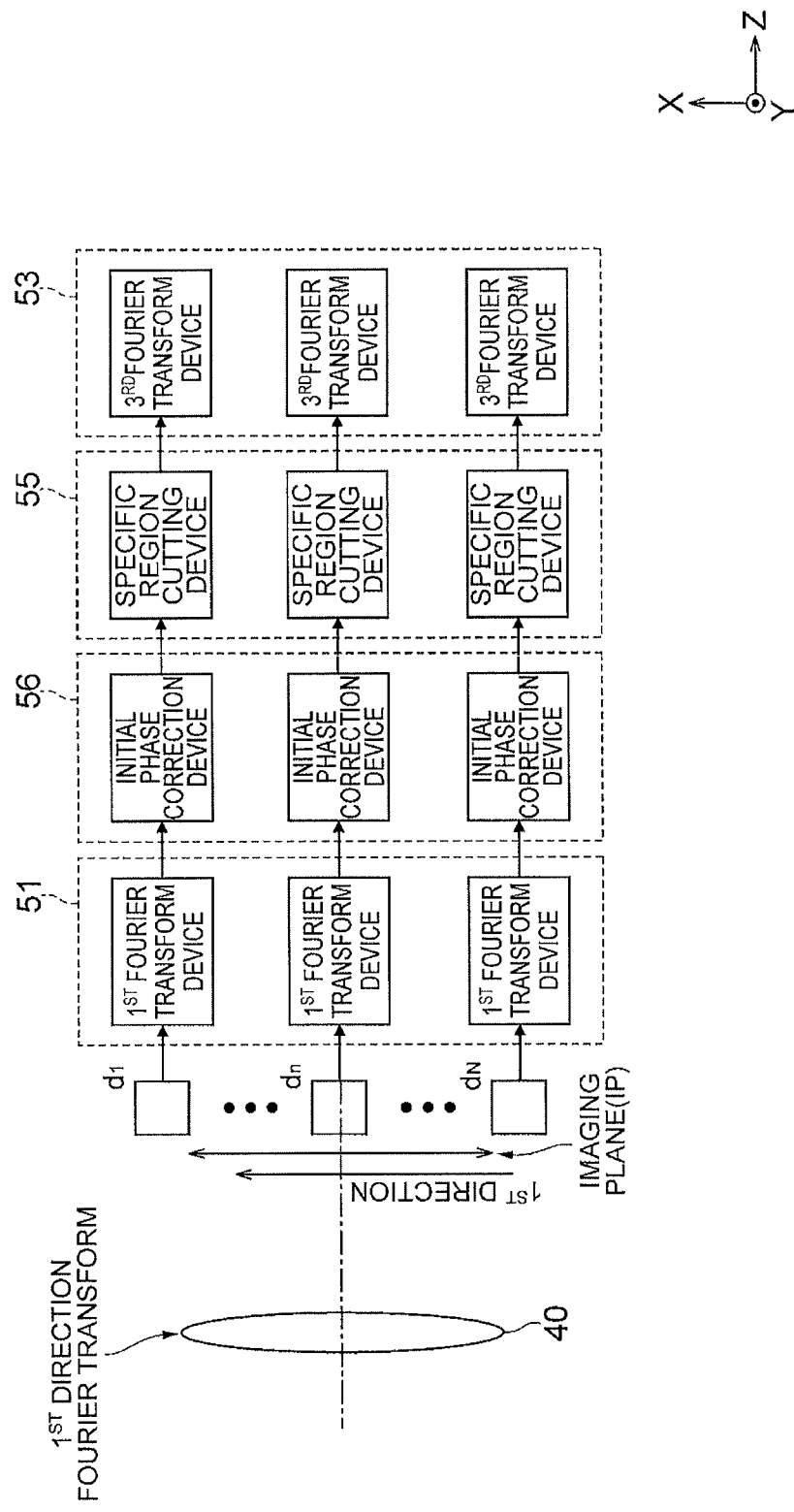
FIG. 33 is a block diagram illustrating structures of the photodetector 46 and arithmetic unit 50 in the fifth arrangement example.

FIG. 33 is a diagram illustrating the structure of the arithmetic unit 50 in the fifth arrangement example performing the foregoing arithmetic processing. The arithmetic unit 50 comprises the lens 40, a first Fourier transform device 51, a third Fourier transform device 53, an initial phase correction device 56, and a specific region cutting device 55. The lens 404 optically performs a Fourier transform of a Fraunhofer diffraction image of the object 2 produced on the back focal plane of the lens 403. The first Fourier transform device 51 performs a one-dimensional Fourier transform with respect to the time variable t of data $s_5(u', \omega)$ obtained by the preceding Fourier transform (Fourier transform with respect to the time variable t in the above-mentioned expression (16)). The initial phase correction device 56 corrects the data obtained by the one-dimensional Fourier transform with the initial phase $\phi_0$. The specific region cutting device 55 cuts out data in a region including the range of a Nyquist frequency $f_{nyq}$ in upper and lower region of the difference frequency $\Delta f$ from thus corrected data G (the above-mentioned expression (14)). The third Fourier transform device 53 performs a one-dimensional Fourier transform of thus cut-out data with respect to the temporal frequency $\omega_d$ (Fourier transform with respect to the temporal frequency w in the above-mentioned expression (15)). When attention is directed to the Fourier transform units, the lens 404, first Fourier transform device 51, and third Fourier transform device 53 are arranged in this order in the arithmetic unit 50 in the fifth arrangement example. Using such arithmetic unit 50, the signal $s_5(u', t)$ is subjected to arithmetic operations, whereby the image $g(\xi, \eta)$ of the object 2 is obtained. A Fraunhofer diffraction image appears on the back focal plane of the lens 403. The lens 404 further performs a Fourier transform, so as to form an image on the light-receiving surface of the photodetector 46. That is, the lens 404 optically performs Fourier transforms in the first and second directions and thus includes the action of the Fourier transform in the first direction. When compared with the arithmetic unit in the first arrangement example, the fifth arrangement example is equivalent to a state where the lens 404 optically acts as the fourth Fourier transform device 54 in the arithmetic unit of the first arrangement example.

Sixth Arrangement Example

In the observation device 1 in which the light-receiving surface of the photodetector 46 is arranged on a u"v" plane (plane where a Fresnel diffraction image of the object is formed) which is a given plane perpendicular to the optical axis in front or rear of the lens 40 in both of the first and second directions of the lens 40 as in the third arrangement example, a structure in which the order of arranging arithmetic devices in the arithmetic unit 50 of the third arrangement example is changed will now be explained as the sixth arrangement example. The lens 40 in the sixth example has a lens structure similar to that in the third arrangement example illustrated in FIG. 28.

The arithmetic unit 50 in the third arrangement example performs a first two-dimensional Fourier transform of the signal $s_3(u", t)$ issued from the photodetector 46, so as to yield $G(u, \Delta 107 +\omega_d)H(u)$ as in the expression (19). The first two-dimensional Fourier transform is equivalent to performing respective one-dimensional Fourier transforms with respect to the time variable t and the variable u". The arithmetic unit 50 in the third arrangement example divides a distribution $G(u, \omega_d)H(u)$, cutting out a frequency region including the range of a Nyquist frequency $f_{nyq}$ in upper and lower region of the difference frequency $\Delta\omega$ acting as the center frequency from the data $G(u, \Delta\omega+\omega_d)H(u)$, by a quadratic phase $H(u)$ and then performs a second two-dimensional inverse Fourier transform, so as to yield $g(\xi, \eta)$. The action of the second two-dimensional Fourier transform is equivalent to performing respective one-dimensional Fourier transforms with respect to the temporal frequency $\omega_d$ and the variable u.

When attention is directed to arithmetic operations in the first direction (u" and u' directions), it is constructed by the one-dimensional Fourier transform with respect to the variable u", the division by the quadratic phase $H(u)$ (quadratic phase dividing device 57), and the one-dimensional Fourier transform with respect to the variable u in this order. In the following, these arithmetic operations concerning the first direction will collectively be referred to as quadratic phase correction unit 60.

The arithmetic unit 50 in the third arrangement example is equivalent to a structure in which the quadratic phase dividing device 57 is added to the arithmetic unit 50 in the second arrangement example. The arithmetic unit 50 in the third arrangement example is also equivalent to a structure in which the quadratic phase correction unit 60 is added to the arrangement example 50 in the fifth arrangement example.

As the lens 40 in the sixth example, one having a structure including the objective lens 405 and a lens 406 such as those illustrated in FIG. 28 is used, while the photodetector 46 is arranged on a given plane perpendicular to the optical axis in front or rear thereof, as in the third example.

Figure 34:
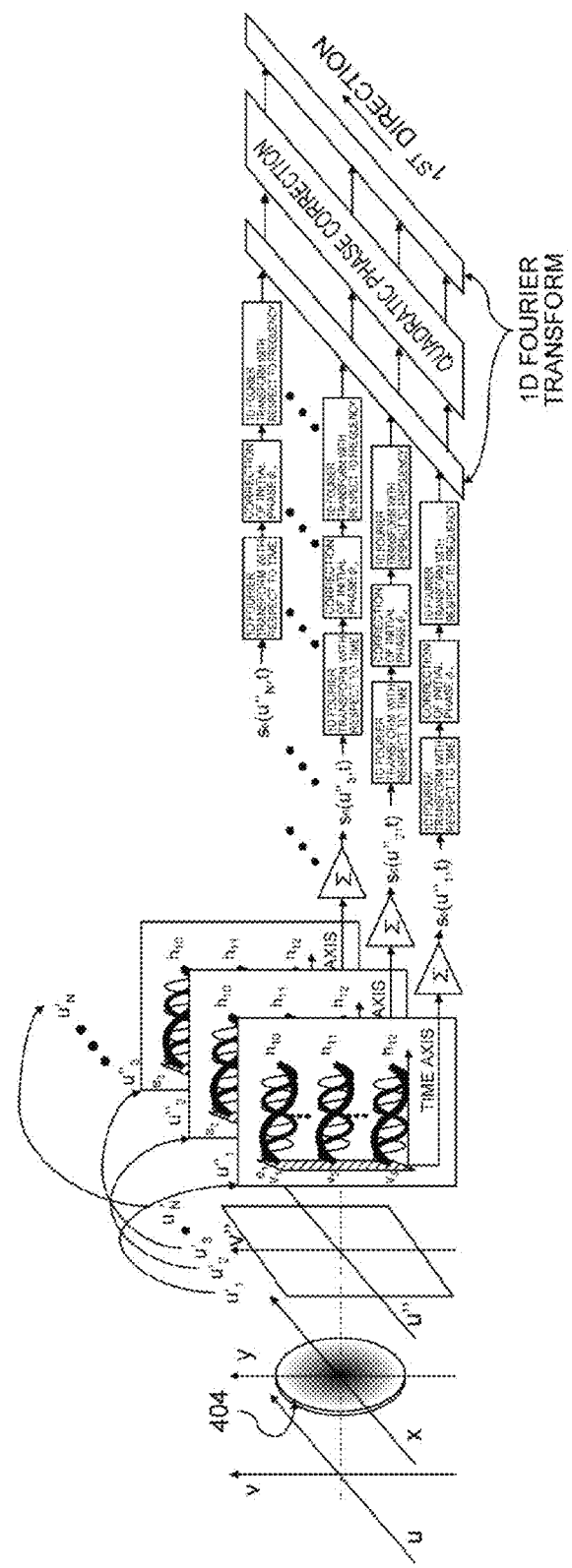
FIG. 34 is a schematic diagram of arithmetic operations performed by the arithmetic unit 50 in a sixth arrangement example.

FIG. 34 illustrates a schematic diagram of arithmetic operations performed by the arithmetic unit 50 in the sixth arrangement example. The sixth arrangement example includes the lens 40 similar to that in the third arrangement example, while the quadratic phase correction unit 60 is arranged behind the arithmetic unit 50 in the fifth arrangement example. In the sixth arrangement example, the arithmetic unit 50 performs the following arithmetic processing, so as to obtain the image of the object 2. That is, the arithmetic unit 50 acquires data of a signal $s_6(u'', t)$ employing the position u" on the u"v" plane and the time t as variables, performs a Fourier transform of the data of the signal $s_6(u'', t)$ with respect to the time variable t (Fourier transform with respect to the time variable t in the above-mentioned expression (19)), corrects the data obtained by this one-dimensional Fourier transform with the initial phase $\phi_0$, cuts out data in a region including the range of a Nyquist frequency $f_{nyq}$ in upper and lower region of the difference frequency $\Delta f$ from thus corrected data G (the above-mentioned expression (14)), performs a one-dimensional Fourier transform of thus cut-out data with respect to the temporal frequency $\omega_d$ (Fourier transform with respect to the temporal frequency $\omega$ in the above-mentioned expression (15)), does a one-dimensional Fourier transform of the data obtained by the Fourier transform with respect to the variable u" (Fourier transform with respect to the variable u" in the above-mentioned expression (19)), divides the result by H, so as to obtain G with respect to only u-direction of the uv plane (the above-mentioned expression (20)), and performs a one-dimensional Fourier transform of thus obtained data (Fourier transform with respect to the variable u in the above-mentioned expression (15)), thereby yielding the image $g(\xi, \eta)$ of the object 2.

As in the foregoing, the sixth arrangement example decomposes the two two-dimensional Fourier transforms in the third arrangement example into one-dimensional Fourier transforms in the first direction and other directions and rearranges these one-dimensional Fourier transforms, and its mathematical operation method is the same as that in the third arrangement example. The quadratic phase correction unit 60 exhibits the action in the first direction of the lens 404 in the second arrangement example together with the action in the first direction of the lens 406 constituting the lens 40 in the third arrangement example. Therefore, removing the lens 406 and the quadratic phase correction unit 60 from the sixth arrangement example and arranging the light-receiving surface of the photodetector 46 on the uv plane makes the first arrangement example.

Figure 35:
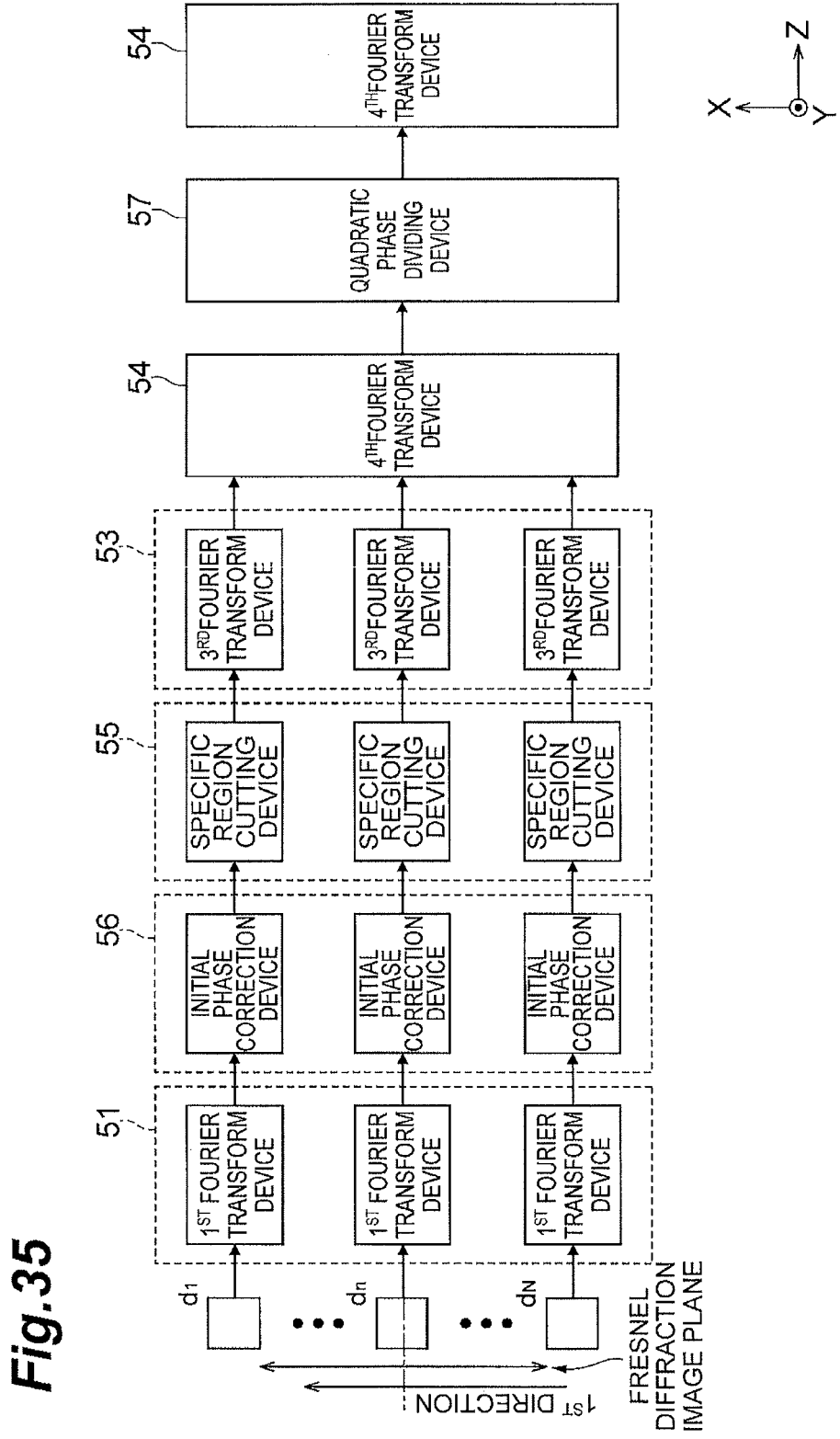
FIG. 35 is a block diagram illustrating structures of the photodetector 46 and arithmetic unit 50 in the sixth arrangement example.

FIG. 35 is a diagram illustrating the structure of the arithmetic unit 50 in the sixth arrangement example performing the foregoing arithmetic processing. The arithmetic unit 50 comprises a first Fourier transform device 51, a second Fourier transform unit 52, a specific region cutting device 55, an initial phase correction device 56, and a quadratic phase dividing device 57. The second Fourier transform unit 52 includes a third Fourier transform device 53 and two fourth Fourier transform devices 54. The first Fourier transform device 51 performs a one-dimensional Fourier transform of data of the signal $s_6(u'', t)$ employing the time t on the u"v" plane as a variable with respect to the time variable t (Fourier transform with respect to the time variable t in the above-mentioned expression (19)). The initial phase correction device 56 corrects the data obtained by the one-dimensional Fourier transform with the initial phase $\phi_0$. The specific region cutting device 55 cuts out data in a region including the range of a Nyquist frequency $f_{nyq}$ in upper and lower region of the difference frequency $\Delta f$ from thus corrected data (the above-mentioned expression (14)). The third Fourier transform device 53 performs a one-dimensional Fourier transform of thus cut-out data with respect to the temporal frequency $\omega_d$ (Fourier transform with respect to the temporal frequency $\omega$ in the above-mentioned expression (15)). The fourth Fourier transform device 54 arranged behind the third Fourier transform device 53 performs a one-dimensional Fourier transform with respect to the variable u" (Fourier transform with respect to the variable u" in the above-mentioned expression (19)). The quadratic phase dividing device 57 divides thus Fourier-transformed data by the quadratic phase H(u) (the above-mentioned expression (20)). The fourth Fourier transform device 54 arranged behind the quadratic phase dividing device 57 performs a one-dimensional Fourier transform with respect to the variable u (Fourier transform with respect to the variable u in the above-mentioned expression (15)). When attention is directed to the Fourier transform units, the first Fourier transform device 51, third Fourier transform device 53, and fourth Fourier transform devices 54, 54 are arranged in this order in the arithmetic unit 50 in the sixth arrangement example. The fourth Fourier transform device 54 arranged behind the third Fourier transform device 53 is not restricted to this position but may be arranged between the first Fourier transform device 51 and the third Fourier transform device 53, or in front of the first Fourier transform device 51, for example. The fourth Fourier transform device 54 arranged behind the other fourth Fourier transform device 54 is not restricted to this position but may be arranged between the first Fourier transform device 51 and the third Fourier transform device 53, or in front of the first Fourier transform device 51, for example. By using such arithmetic devices, the arithmetic unit 50 performs arithmetic operations for the signal $s_6(u'', t)$, thereby yielding the image $g(\xi, \eta)$ of the object 2.

The lens 40 arranged between the object 2 and the photodetector 46 in the observation device 1 of this embodiment exhibits the same action in the x and y directions for scattered light in the foregoing explanation. However, the optical system between the object 2 and the photodetector 46 may magnify or reduce the Fourier image by a relay optical system having an anamorphic magnification.

Seventh Arrangement Example

The seventh arrangement example will now be explained. The seventh arrangement example is the same as the first arrangement example except for the structure of the lens 40. In the seventh arrangement example, the light-receiving surface of the photodetector 46 is arranged on a plane where a Fraunhofer diffraction image of the object 2 is formed in the x direction (first direction) by the lens 40, which is also a plane where a Fraunhofer diffraction image of the object 2 is formed in the y direction (second direction). The lens 40 in the seventh arrangement example is arranged between the object 2 and the photodetector 46.

Figure 36:
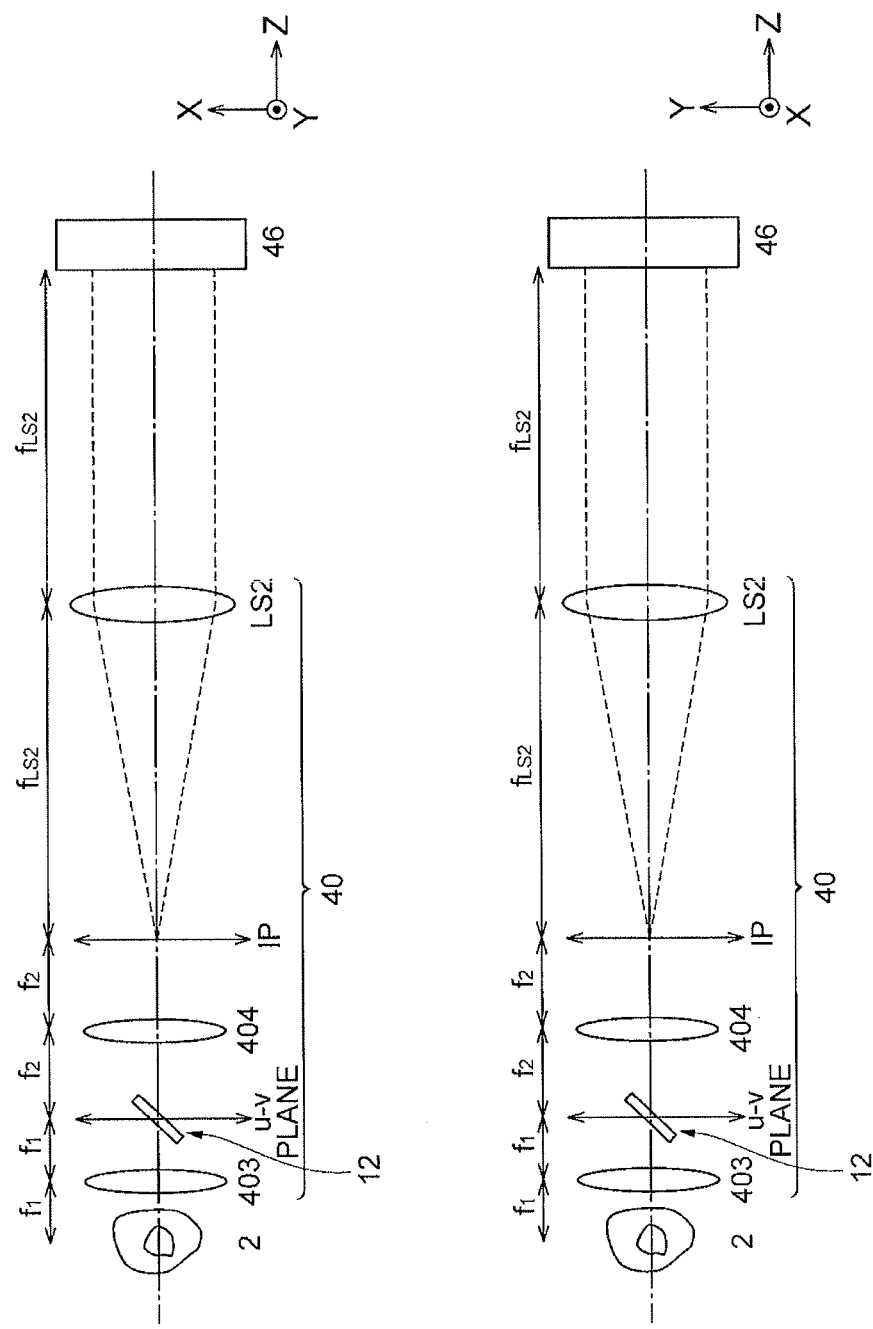
FIG. 36 is a diagram illustrating a structural example of the lens 40 in a seventh arrangement example.

FIG. 36 illustrates details of the lens 40 in the seventh arrangement example. In the seventh arrangement example, the lens 40 is constructed by three lenses composed of the lenses 403, 404 constituting the lens 40 in the second arrangement example and an additional lens LS2. Each of the three lenses constructing the lens 40 is a spherical lens. In the image-forming action by the lens, the spherical lenses exhibit the same actions in the x and y directions. The beam splitter 12 is arranged on the back focal plane of the lens 403 constituting the lens 40 so as to split the substantially zero-order light in two. The light reflected by the beam splitter 12 is fed to the lens 60 as the second light.

The lens 40 in the second arrangement example forms an object image on a plane IP. In each of the x and y directions, an image of the object 2 is once formed on the plane IP by the lenses 403, 404. The front focal plane of the lens LS2 coincides with the plane IP. The back focal plane of the lens LS2 coincides with the light-receiving surface of the photodetector 46. Thus, a Fraunhofer diffraction image of the object 2 is formed on the light-receiving surface of the photodetector 46 in each of the x and y directions of the lens.

A method of processing a signal obtained in the photodetector 46 by thus constructed lens 40 will now be explained. Let the coordinate system on the light-receiving surface of the photodetector 46 be the uv plane as in the first arrangement example. In the first arrangement example, Fraunhofer diffraction images appear on the uv plane in the u and v directions. In the seventh arrangement example, Fraunhofer diffraction images appear in the u and v directions. The seventh arrangement example differs from the first arrangement example in the structure of the lens 40.

Let $s_7(u, t)$ be a signal representing the sum of signals on a line parallel to the v direction. The arithmetic processing for obtaining the complex amplitude image $g(\xi, \eta)$ according to $s_7(u, t)$ issued from the photodetector 46 and the arithmetic device structure for performing this processing are the same as the arithmetic processing for obtaining the complex amplitude image $g(\xi, \eta)$ according to $s_1(u, t)$ obtained by the first arrangement example and the arithmetic device structure for performing this processing. Therefore, the arithmetic processing for obtaining the complex amplitude image $g(\xi, \eta)$ according to $s_7(u, t)$ issued from the photodetector 46 and the arithmetic device structure for performing this processing will not be explained.

Eighth Arrangement Example

The eighth arrangement example will now be explained. The eighth arrangement example is the same as the first arrangement example except for the structure of the lens 40. In the eighth arrangement example, the light-receiving surface of the photodetector 46 is arranged on a plane where a Fraunhofer diffraction image of the object 2 is formed in the x direction (first direction) by the lens 40, which is also a plane where an image of the object 2 is formed in the y direction (second direction). The lens 40 in the eighth arrangement example is arranged between the object 2 and the photodetector 46.

Figure 37:
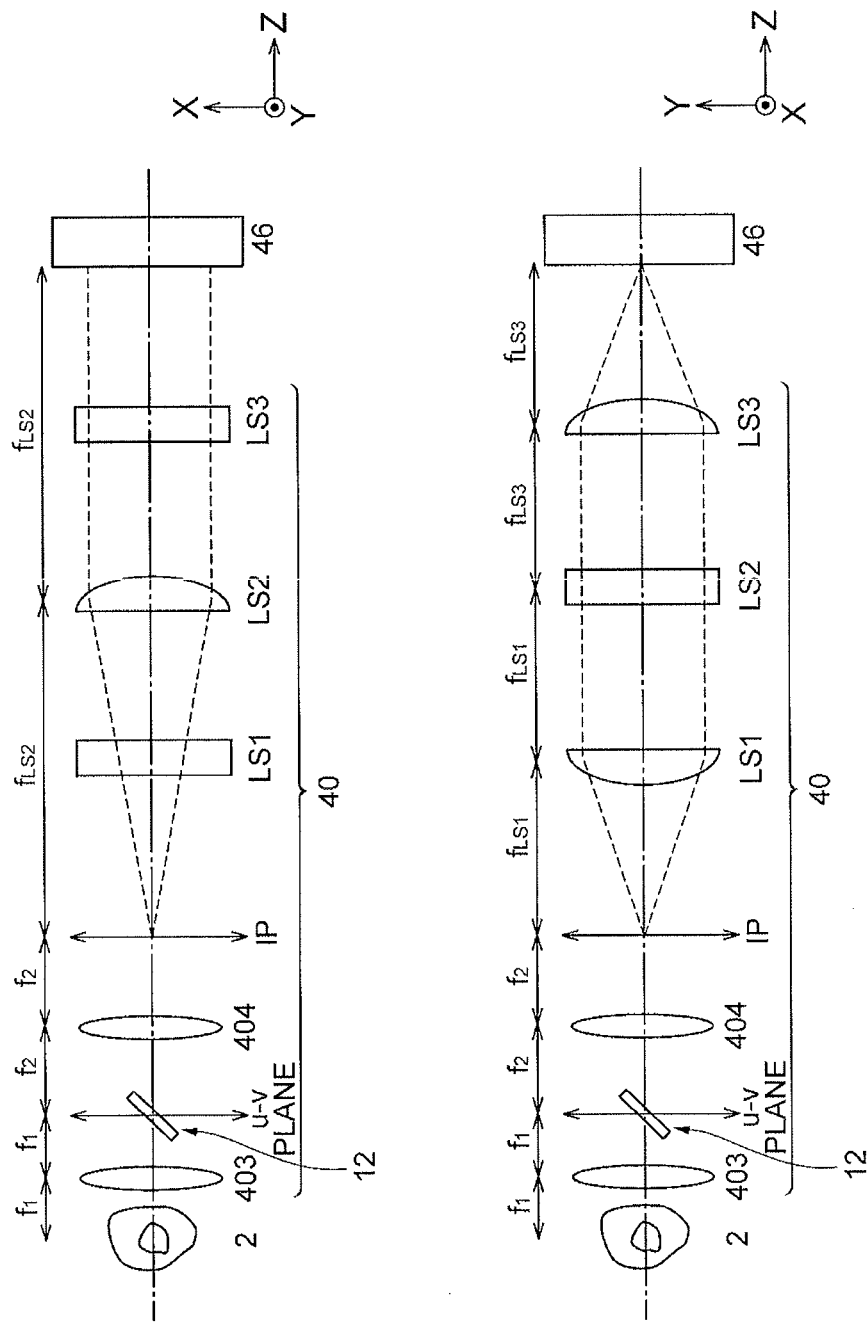
FIG. 37 is a diagram illustrating a structural example of the lens 40 in an eighth arrangement example.

FIG. 37 illustrates details of the lens 40 in the eighth arrangement example. In the eighth arrangement example, the lens 40 is constructed by five lenses composed of the lenses 403, 404 constituting the lens 40 in the second arrangement example and additional lenses LS1, LS2, LS3. In the five lenses constituting the lens 40, the lenses 403, 404 are spherical lenses, while the lenses LS1, LS2, LS3 are cylindrical lenses. In the image-forming action by the lens, the cylindrical lenses exhibit different actions in the x and y directions. Let $f_{LS1}$, $f_{LS2}$, and $f_{LS3}$ be the focal lengths of the lenses LS1, LS2, LS3, respectively. Suppose that these focal lengths have the relationships of $f_{LS1}=f_{LS3}$, and $f_{LS2}=2f_{LS1}=2f_{LS3}$. The beam splitter 12 is arranged on the back focal plane of the lens 403 constituting the lens 40 so as to split the substantially zero-order light in two. The light reflected by the beam splitter 12 is fed to the lens 60 as the second light.

In the x direction, the lenses LS1, LS3 have no curvature and thus do not contribute to forming images. Therefore, the lens structure in the x direction is equivalent to a structure in which only the lenses 403, 404, LS2 are arranged as illustrated in the upper side of FIG. 37. In the y direction, on the other hand, the lens LS2 has no curvature and thus does not contribute to forming images. Therefore, the lens structure in the y direction is equivalent to a structure in which only the lenses 403, 404, LS1, LS3 are arranged as illustrated in the lower side of FIG. 37.

In the x direction, an image of the object 2 is once formed on a plane IP by the lenses 403, 404. Subsequently, a Fraunhofer diffraction image of the image is formed on the light-receiving surface under an action of the lens LS2 which is the same as that in the seventh arrangement example. In the y direction, on the other hand, an image of the object 2 is once formed on the plane IP by the lenses 403, 404. The lenses LS1, LS3 constitute a so-called 4f optical system. The 4f optical system is an optical system in which the back focal plane of the lens LS1 coincides with the front focal plane of the lens LS3, so that an image of the front focal plane of the lens LS1 is formed on the back focal plane of the lens LS3. Thus, the Fraunhofer diffraction image and image of the object 2 are formed on the light-receiving surface of the photodetector 46 in the x and y directions, respectively, by the lens 40 in the eighth arrangement example.

A method of processing a signal obtained in the photodetector 46 by thus constructed lens 40 will now be explained. Let the coordinate system on the light-receiving surface of the photodetector 46 be the uv plane as in the first arrangement example. In the first arrangement example, Fraunhofer diffraction images appear on the uv plane in the u and v directions. In the eighth arrangement example, a Fraunhofer diffraction image and an object image appear in the u and v directions, respectively. Let $s_8(u, t)$ be a signal representing the sum of signals on a line parallel to the v direction. The arithmetic processing for obtaining the complex amplitude image $g(\xi, \eta)$ according to $s_8(u, t)$ issued from the photodetector 46 and the arithmetic device structure for performing this processing are the same as the arithmetic processing for obtaining the complex amplitude image $g(\xi, \eta)$ according to $s_1(u, t)$ obtained by the first arrangement example and the arithmetic device structure for performing this processing. Therefore, the arithmetic processing for obtaining the complex amplitude image $g(\xi, \eta)$ according to $s_8(u, t)$ issued from the photodetector 46 and the arithmetic device structure for performing this processing will not be explained.

Ninth Arrangement Example

The ninth arrangement example will now be explained. The ninth arrangement example is the same as the first arrangement example except for the structure of the lens 40. In the ninth arrangement example, the light-receiving surface of the photodetector 46 is arranged on a plane where a Fraunhofer diffraction image of the object 2 is formed in the x direction (first direction) by the lens 40, which is also a plane where a Fresnel diffraction image of the object is formed in the y direction (second direction). The lens 40 in the ninth arrangement example is arranged between the object 2 and the photodetector 46.

Figure 38:
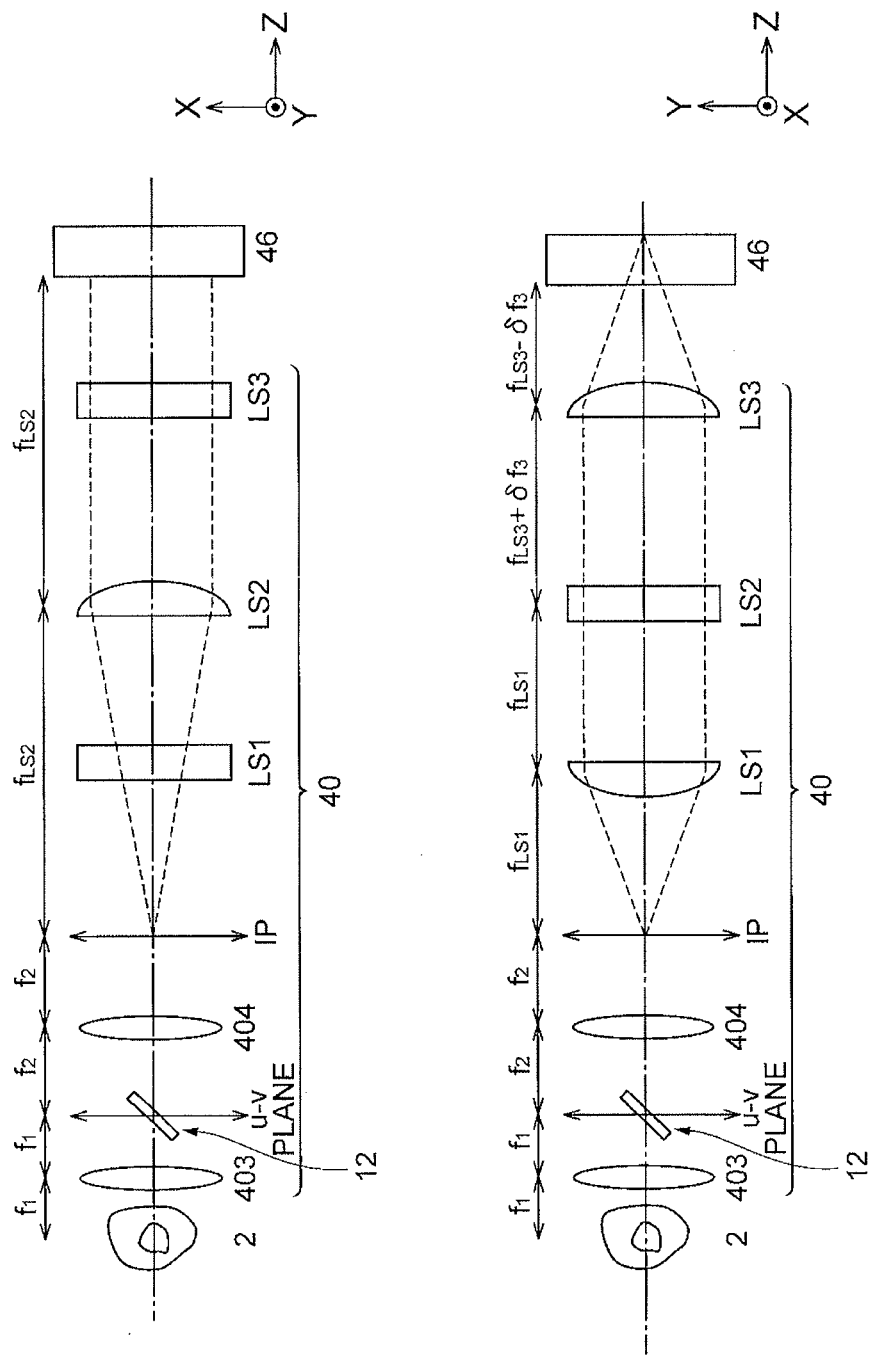
FIG. 38 is a diagram illustrating a structural example of the lens 40 in a ninth arrangement example.

FIG. 38 illustrates details of the lens 40 in the ninth arrangement example. In the ninth arrangement example, the lens 40 is constructed by five lenses composed of the lenses 403, 404 constituting the lens 40 in the second arrangement example and additional lenses LS1, LS2, LS3. In the five lenses constituting the lens 40, the lenses 403, 404 are spherical lenses, while the lenses LS1, LS2, LS3 are cylindrical lenses. In the image-forming action by the lens, the cylindrical lenses exhibit different actions in the x and y directions. The beam splitter 12 is arranged on the back focal plane of the lens 403 constituting the lens 40 so as to split the substantially zero-order light in two. The light reflected by the beam splitter 12 is fed to the lens 60 as the second light.

In the x direction, the lenses LS1, LS3 have no curvature and thus do not contribute to forming images. Therefore, the lens structure in the x direction is equivalent to a structure in which only the lenses 403, 404, LS2 are arranged as illustrated in the upper side of FIG. 38. In the y direction, on the other hand, the lens LS2 has no curvature and thus does not contribute to forming images. Therefore, the lens structure in the y direction is equivalent to a structure in which only the lenses 403, 404, LS1, LS3 are arranged as illustrated in the lower side of FIG. 38.

In the x direction, an image of the object 2 is once formed on a plane IP by the lenses 403, 404. Subsequently, a Fraunhofer diffraction image of the image is formed on the light-receiving surface of the photodetector 46 under an action of the lens LS2 which is the same as that in the seventh arrangement example. In the y direction, on the other hand, an image of the object 2 is once formed on the plane IP by the lenses 403, 404. The lenses LS1, LS3 do not construct a so-called 4f optical system. That is, as illustrated in the lower side of FIG. 38, the front focal plane of the lens LS3 does not coincide with the back focal plane of the lens LS1. Therefore, none of images of the object 2 and Fourier images thereof is formed on the light-receiving surface of the photodetector 46. Thus, the Fraunhofer and Fresnel diffraction images of the object 2 are formed on the light-receiving surface of the photodetector 46 in the x and y directions, respectively, by the lens 40.

A method of processing a signal obtained in the photodetector 46 by thus constructed lens 40 will now be explained. Let the coordinate system on the light-receiving surface of the photodetector 46 be the uv plane as in the first arrangement example. In the first arrangement example, Fraunhofer diffraction images appear on the uv plane in the u and v directions. In the ninth arrangement example, the Fraunhofer and Fresnel diffraction images of the object appear in the u and v directions, respectively. Let $s_9(u, t)$ be a signal representing the sum of signals on a line parallel to the v direction. The arithmetic processing for obtaining the complex amplitude image $g(\xi, \eta)$ according to $s_9(u, t)$ issued from the photodetector 46 and the arithmetic device structure for performing this processing are the same as the arithmetic processing for obtaining the complex amplitude image $g(\xi, \eta)$ according to $s_1(u, t)$ obtained by the first arrangement example and the arithmetic device structure for performing this processing. Therefore, the arithmetic processing for obtaining the complex amplitude image $g(\xi, \eta)$ according to $s_9(u, t)$ issued from the photodetector 46 and the arithmetic device structure for performing this processing will not be explained.

Tenth Arrangement Example

The tenth arrangement example will now be explained. The tenth arrangement example is the same as the second or fifth arrangement example except for the structure of the lens 40. In the tenth arrangement example, the light-receiving surface of the photodetector 46 is arranged on a plane where an image of the object 2 is formed in the x direction (first direction) by the lens 40, which is also a plane where a Fraunhofer diffraction image of the object 2 is formed in the y direction (second direction). The lens 40 in the tenth arrangement example is arranged between the object 2 and the photodetector 46.

Figure 39:
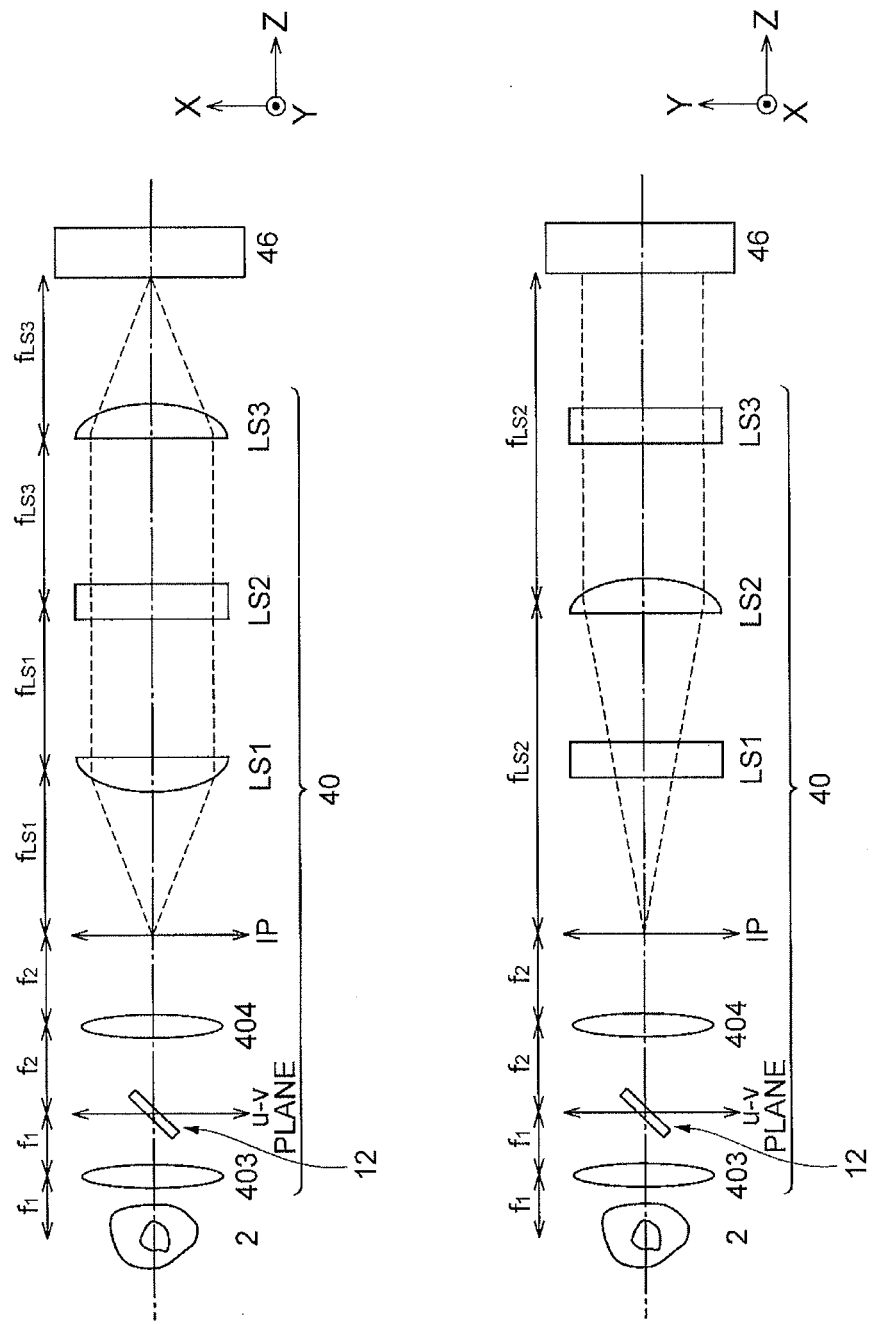
FIG. 39 is a diagram illustrating a structural example of the lens 40 in a tenth arrangement example.

FIG. 39 illustrates details of the lens 40 in the tenth arrangement example. In the tenth arrangement example, the lens 40 is constructed by five lenses composed of the lenses 403, 404 constituting the lens 40 in the second arrangement example and additional lenses LS1, LS2, LS3. In the five lenses constituting the lens 40, the lenses 403, 404 are spherical lenses, while the lenses LS1, LS2, LS3 are cylindrical lenses. In the image-forming action by the lens, the cylindrical lenses exhibit different actions in the x and y directions. The beam splitter 12 is arranged on the back focal plane of the lens 403 constituting the lens 40 so as to split the substantially zero-order light in two. The light reflected by the beam splitter 12 is fed to the lens 60 as the second light.

In the x direction, the lens LS2 has no curvature and thus does not contribute to forming images. Therefore, the lens structure in the x direction is equivalent to a structure in which only the lenses 403, 404, LS1, LS3 are arranged as illustrated in the upper side of FIG. 39. In the y direction, on the other hand, the lenses LS1, LS3 have no curvature and thus do not contribute to forming images. Therefore, the lens structure in the y direction is equivalent to a structure in which only the lenses 403, 404, LS2 are arranged as illustrated in the lower side of FIG. 39.

In the x direction, an image of the object 2 is once formed on a plane IP by the lenses 403, 404. The lenses LS1, LS3 constitute a so-called 4f optical system. The 4f optical system is an optical system in which the back focal plane of the lens LS1 coincides with the front focal plane of the lens LS3, so that an image of the front focal plane of the lens LS1 is formed on the back focal plane of the lens LS3. In the y direction, on the other hand, an image of the object 2 is once formed on the plane IP by the lenses 403, 404. Subsequently, a Fraunhofer diffraction image of the image is formed on the light-receiving surface of the photodetector 46 under an action of the lens LS2 which is the same as that in the seventh arrangement example. Thus, the image and Fraunhofer diffraction image of the object 2 are formed on the light-receiving surface of the photodetector 46 in the x and y directions, respectively, by the lens 40.

A method of processing a signal obtained in the photodetector 46 by thus constructed lens 40 will now be explained. Let the coordinate system on the light-receiving surface of the photodetector 46 be the u'v' plane as in the second arrangement example. In the second or fifth arrangement example, images of the object 2 appear on the u'v' plane in the u' and v' directions. In the tenth arrangement example, an image of the object 2 and a Fraunhofer diffraction image of the object appear in the u' and v' directions, respectively. Let $s_{10}(u', t)$ be a signal representing the sum of signals on a line parallel to the v' direction. The arithmetic processing for obtaining the complex amplitude image $g(\xi, \eta)$ according to $s_{10}(u', t)$ issued from the photodetector 46 and the arithmetic device structure for performing this processing are the same as the arithmetic processing for obtaining the complex amplitude image $g(\xi, \eta)$ according to $s_2(u', t)$ or $s_5(u', t)$ obtained by the second or fifth arrangement example and the arithmetic device structure for performing this processing. That is, the light source 10, lens 40, photodetector 46, first Fourier transform device 51, fourth Fourier transform device 54, third Fourier transform device 53, and fourth Fourier transform device 54 are arranged in this order when employing the structure of the second arrangement example. The light source 10, lens 40, photodetector 46, first Fourier transform device 51, and third Fourier transform device 53 are arranged in this order when employing the structure of the fifth arrangement example. Therefore, the arithmetic processing for obtaining the complex amplitude image $g(\xi, \eta)$ according to $s_{10}(u', t)$ issued from the photodetector 46 and the arithmetic device structure for performing this processing will not be explained.

Eleventh Arrangement Example

The eleventh arrangement example will now be explained. The eleventh arrangement example is the same as the second or fifth arrangement example except for the structure of the lens 40. In the eleventh arrangement example, the light-receiving surface of the photodetector 46 is arranged on a plane where an image of the object 2 is formed in the x direction (first direction) by the lens 40, which is also a plane where an image of the object 2 is formed in the y direction (second direction). The lens 40 in the eleventh arrangement example is arranged between the object 2 and the photodetector 46.

Figure 40:
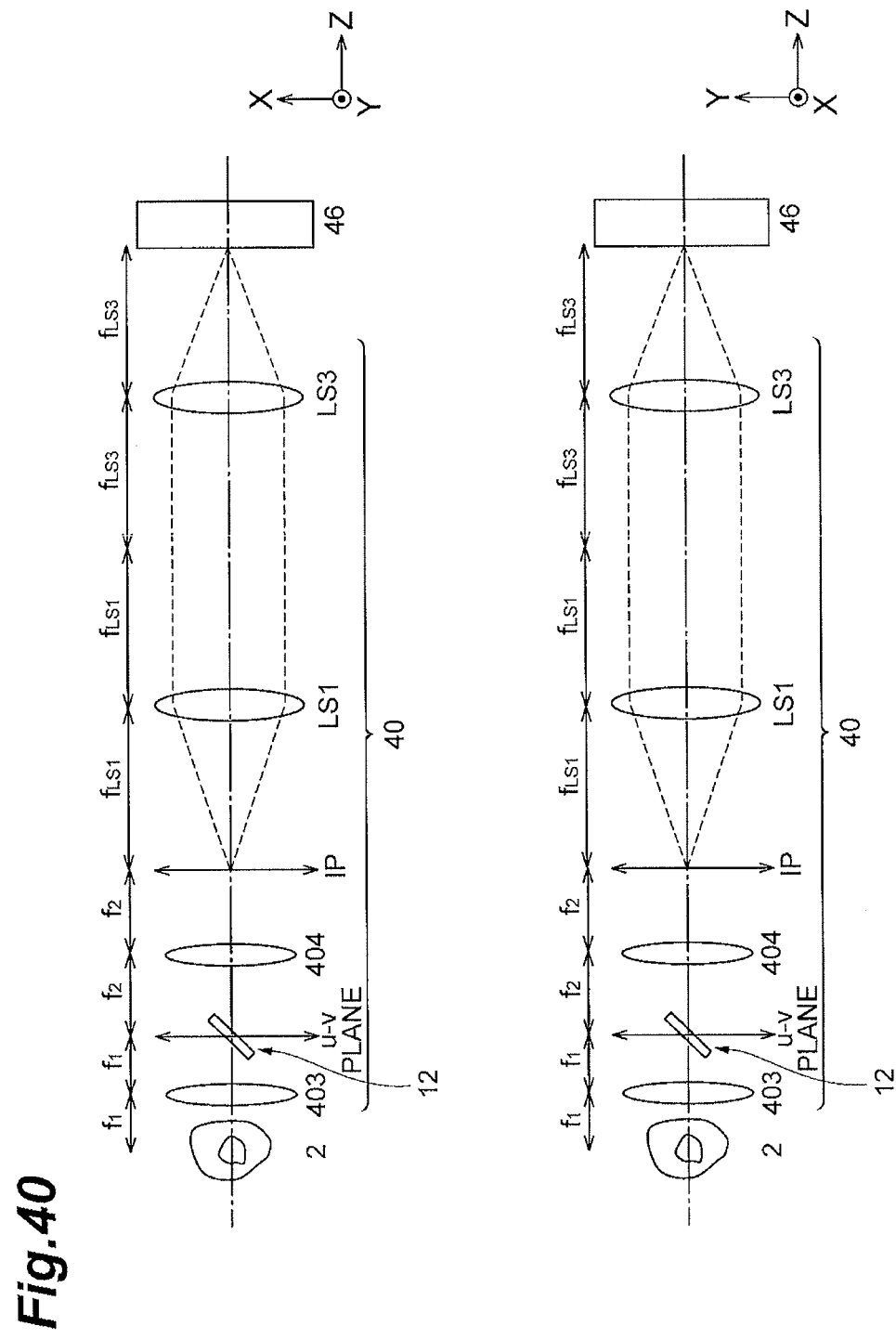
FIG. 40 is a diagram illustrating a structural example of the lens 40 in an eleventh arrangement example.

FIG. 40 illustrates details of the lens 40 in the eleventh arrangement example. In the eleventh arrangement example, the lens 40 is constructed by four lenses composed of the lenses 403, 404 constituting the lens 40 used in the second arrangement example and additional lenses LS1, LS3. The four lenses constituting the lens 40 are spherical lenses. In the image-forming action by the lens, these spherical lenses exhibit the same action in the x and y directions. The beam splitter 12 is arranged on the back focal plane of the lens 403 constituting the lens 40 so as to split the substantially zero-order light in two. The light reflected by the beam splitter 12 is fed to the lens 60 as the second light.

Therefore, in each of the x and y directions, an image of the object 2 is once formed on a plane IP by the lenses 403, 404. The lenses LS1, LS3 constitute a so-called 4f optical system. The 4f optical system is an optical system in which the back focal plane of the lens LS1 coincides with the front focal plane of the lens LS3, so that an image of the front focal plane of the lens LS1 is formed on the back focal plane of the lens LS3. Thus, the lens 40 forms an image of the object 2 on the light-receiving surface of the photodetector 46 in each of the x and y directions.

A method of processing a signal obtained in the photodetector 46 by thus constructed lens 40 will now be explained. Let the coordinate system on the light-receiving surface of the photodetector 46 be the u'v' plane as in the second arrangement example. In the second or fifth arrangement example, images of the object 2 appear on the u'v' plane in the u' and v' directions. Similarly, images of the object 2 appear on the u'v' plane in the u' and v' directions in the eleventh arrangement example. The eleventh arrangement example differs from the second arrangement example in the structure of the lens 40. Let $s_{11}(u', t)$ be a signal representing the sum of signals on a line parallel to the v' direction. The arithmetic processing for obtaining the complex amplitude image $g(\xi, \eta)$ according to $s_{11}(u', t)$ issued from the photodetector 46 and the arithmetic device structure for performing this processing are the same as the arithmetic processing for obtaining the complex amplitude image $g(\xi, \eta)$ according to $s_2(u', t)$ or $s_5(u', t)$ obtained by the second or fifth arrangement example and the arithmetic device structure for performing this processing. That is, the light source 10, lens 40, photodetector 46, first Fourier transform device 51, fourth Fourier transform device 54, third Fourier transform device 53, and fourth Fourier transform device 54 are arranged in this order when employing the structure of the second arrangement example. The light source 10, lens 40, photodetector 46, first Fourier transform device 51, and third Fourier transform device 53 are arranged in this order when employing the structure of the fifth arrangement example. Therefore, the arithmetic processing for obtaining the complex amplitude image $g(\xi, \eta)$ according to $s_{11}(u', t)$ issued from the photodetector 46 and the arithmetic device structure for performing this processing will not be explained.

Twelfth Arrangement Example

The twelfth arrangement example will now be explained. The twelfth arrangement example is the same as the second or fifth arrangement example except for the structure of the lens 40. In the twelfth arrangement example, the light-receiving surface of the photodetector 46 is arranged on a plane where an image of the object 2 is formed in the x direction (first direction) by the lens 40, which is also a plane where a Fresnel diffraction image of the object 2 is formed in the y direction (second direction). The lens 40 in the twelfth arrangement example is arranged between the object 2 and the photodetector 46.

Figure 41:
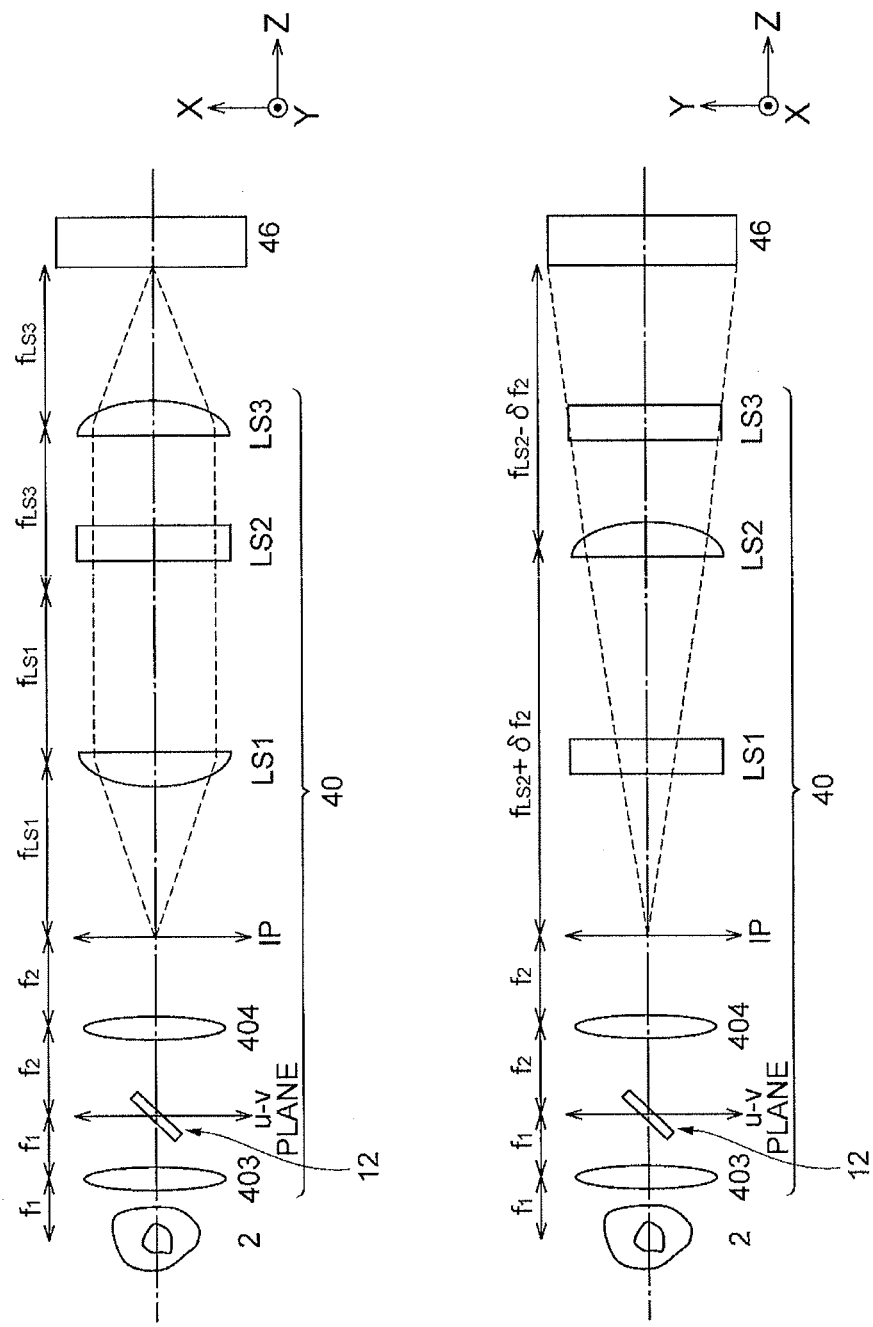
FIG. 41 is a diagram illustrating a structural example of the lens 40 in a twelfth arrangement example.

FIG. 41 illustrates details of the lens 40 in the twelfth arrangement example. In the twelfth arrangement example, the lens 40 is constructed by five lenses composed of the lenses 403, 404 constituting the lens 40 used in the second arrangement example and additional lenses LS1, LS2, LS3. In the five lenses constituting the lens 40, the lenses 403, 404 are spherical lenses, while the lenses LS1, LS2, LS3 are cylindrical lenses. In the image-forming action by the lens, these cylindrical lenses exhibit different actions in the x and y directions. The beam splitter 12 is arranged on the back focal plane of the lens 403 constituting the lens 40 so as to split the substantially zero-order light in two. The light reflected by the beam splitter 12 is fed to the lens 60 as the second light.

In the x direction, the lens LS2 has no curvature and thus does not contribute to forming images. Therefore, the lens structure in the x direction is equivalent to a structure in which only the lenses 403, 404, LS1, LS3 are arranged as illustrated in the upper side of FIG. 41. In the y direction, on the other hand, the lenses LS1, LS3 have no curvature and thus do not contribute to forming images. Therefore, the lens structure in the y direction is equivalent to a structure in which only the lenses 403, 404, LS2 are arranged as illustrated in the lower side of FIG. 41.

In the x direction, an image of the object 2 is once formed on a plane IP by the lenses 403, 404. The lenses LS1, LS3 constitute a so-called 4f optical system. The 4f optical system is an optical system in which the back focal plane of the lens LS1 coincides with the front focal plane of the lens LS3, so that an image of the front focal plane of the lens LS1 is formed on the back focal plane of the lens LS3. In the y direction, on the other hand, an image of the object 2 is once formed on the plane IP by the lenses 403, 404. The front focal plane of the lens LS2 differs from the plane IP of the image of the object 2, while the back focal plane of the lens LS2 differs from the light-receiving surface of the photodetector 46. Therefore, a Fresnel diffraction image of the image is formed on the light-receiving surface. Thus, the image and Fresnel diffraction image of the object 2 are formed on the light-receiving surface of the photodetector 46 in the x and y directions, respectively, by the lens 40 in the twelfth arrangement example.

A method of processing a signal obtained in the photodetector 46 by thus constructed lens 40 will now be explained. Let the coordinate system on the light-receiving surface of the photodetector 46 be the u'v' plane as in the second or fifth arrangement example. In the second or fifth arrangement example, images of the object 2 appear on the u'v' plane in the u' and v' directions. In the twelfth arrangement example, an image of the object 2 and a Fresnel diffraction image of the object appear in the u' and v' directions, respectively. Let $s_{12}(u', t)$ be a signal representing the sum of signals on a line parallel to the v' direction. The arithmetic processing for obtaining the complex amplitude image $g(\xi, \eta)$ according to $s_{12}(u', t)$ issued from the photodetector 46 and the arithmetic device structure for performing this processing are the same as the arithmetic processing for obtaining the complex amplitude image $g(\xi, \eta)$ according to $s_2(u', t)$ or $s_5(u', t)$ obtained by the second or fifth arrangement example and the arithmetic device structure for performing this processing. That is, the light source 10, lens 40, photodetector 46, first Fourier transform device 51, fourth Fourier transform device 54, third Fourier transform device 53, and fourth Fourier transform device 54 are arranged in this order when employing the structure of the second arrangement example. The light source 10, lens 40, photodetector 46, first Fourier transform device 51, and third Fourier transform device 53 are arranged in this order when employing the structure of the fifth arrangement example. Therefore, the arithmetic processing for obtaining the complex amplitude image $g(\xi, \eta)$ according to $s_{12}(u', t)$ issued from the photodetector 46 and the arithmetic device structure for performing this processing will not be explained.

Thirteenth Arrangement Example

The thirteenth arrangement example will now be explained. The thirteenth arrangement example is the same as the third or sixth arrangement example except for the structure of the lens 40. In the thirteenth arrangement example, the light-receiving surface of the photodetector 46 is arranged on a plane where a Fresnel diffraction image of the object 2 is formed in the x direction (first direction) by the lens 40, which is also a plane where a Fraunhofer diffraction image of the object 2 is formed in the y direction (second direction). The lens 40 in the thirteenth arrangement example is arranged between the object 2 and the photodetector 46.

Figure 42:
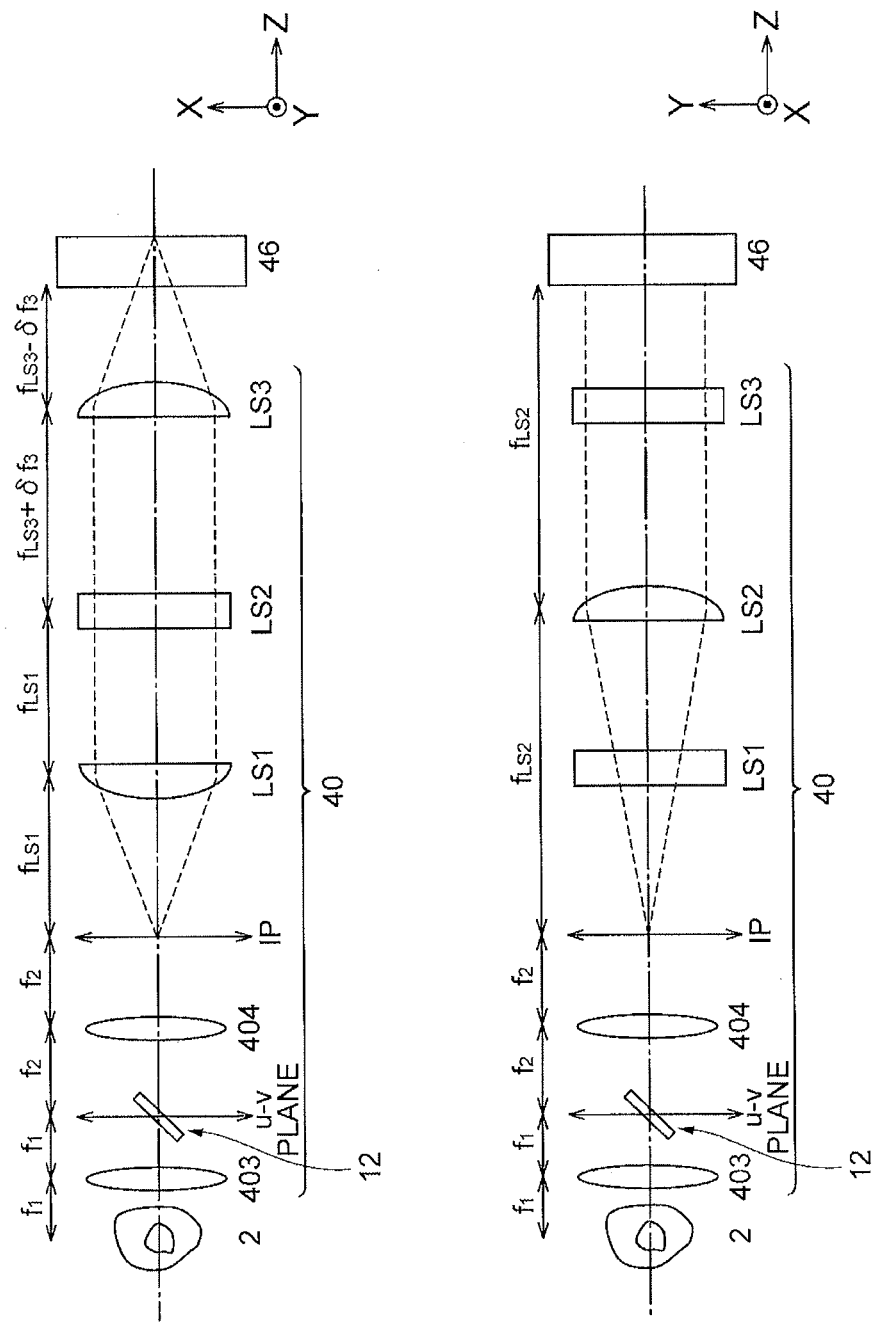
FIG. 42 is a diagram illustrating a structural example of the lens 40 in a thirteenth arrangement example.

FIG. 42 illustrates details of the lens 40 in the thirteenth arrangement example. In the thirteenth arrangement example, the lens 40 is constructed by five lenses composed of the lenses 403, 404 constituting the lens 40 used in the second arrangement example and additional lenses LS1, LS2, LS3. In the five lenses constituting the lens 40, the lenses 403, 404 are spherical lenses, while the lenses LS1, LS2, LS3 are cylindrical lenses. In the image-forming action by the lens, these cylindrical lenses exhibit different actions in the x and y directions. The beam splitter 12 is arranged on the back focal plane of the lens 403 constituting the lens 40 so as to split the substantially zero-order light in two. The light reflected by the beam splitter 12 is fed to the lens 60 as the second light.

In the x direction, the lens LS2 has no curvature and thus does not contribute to forming images. Therefore, the lens structure in the x direction is equivalent to a structure in which only the lenses 403, 404, LS1, LS3 are arranged as illustrated in the upper side of FIG. 42. In the y direction, on the other hand, the lenses LS1, LS3 have no curvature and thus do not contribute to forming images. Therefore, the lens structure in the y direction is equivalent to a structure in which only the lenses 403, 404, LS2 are arranged as illustrated in the lower side of FIG. 42.

In the x direction, an image of the object 2 is once formed on a plane IP by the lenses 403, 404. The lenses LS1, LS3 do not construct a so-called 4f optical system. That is, as illustrated in the upper side of FIG. 42, the front focal plane of the lens LS3 does not coincide with the back focal plane of the lens LS1. Therefore, none of images of the object 2 and Fraunhofer diffraction images thereof is formed on the light-receiving surface. In the y direction, on the other hand, an image of the object 2 is once formed on the plane IP by the lenses 403, 404. Subsequently, a Fraunhofer diffraction image of the image is formed on the light-receiving surface under an action of the lens LS2 which is the same as that in the seventh arrangement example. Thus, the Fresnel and Fraunhofer diffraction images of the object 2 are formed on the light-receiving surface of the photodetector 46 in the x and y directions, respectively, by the lens 40.

A method of processing a signal obtained in the photodetector 46 by thus constructed lens 40 will now be explained. Let the coordinate system on the light-receiving surface of the photodetector 46 be the u"v" plane as in the third or sixth arrangement example. In the third or sixth arrangement example, Fresnel diffraction images of the object 2 appear on the u"v" plane in the u" and v" directions. In the thirteenth arrangement example, the Fresnel and Fraunhofer diffraction images of the object appear in the u" and v" directions, respectively. Let $s_{13}(u", t)$ be a signal representing the sum of signals on a line parallel to the v" direction. The arithmetic processing for obtaining the complex amplitude image $g(\xi, \eta)$ according to $s_{13}(u", t)$ issued from the photodetector 46 and the arithmetic device structure for performing this processing are the same as the arithmetic processing for obtaining the complex amplitude image $g(\xi, \eta)$ according to $s_3(u", t)$ or $s_6(u", t)$ obtained by the third or sixth arrangement example and the arithmetic device structure for performing this processing. Therefore, the arithmetic processing for obtaining the complex amplitude image $g(\xi, \eta)$ according to $s_{13}(u", t)$ issued from the photodetector 46 and the arithmetic device structure for performing this processing will not be explained.

Fourteenth Arrangement Example

The fourteenth arrangement example will now be explained. The fourteenth arrangement example is the same as the third or sixth arrangement example except for the structure of the lens 40. In the fourteenth arrangement example, the light-receiving surface of the photodetector 46 is arranged on a plane where a Fresnel diffraction image of the object 2 is formed in the x direction (first direction) by the lens 40, which is also a plane where an image of the object 2 is formed in the y direction (second direction). The lens 40 in the fourteenth arrangement example is arranged between the object 2 and the photodetector 46.

Figure 43:
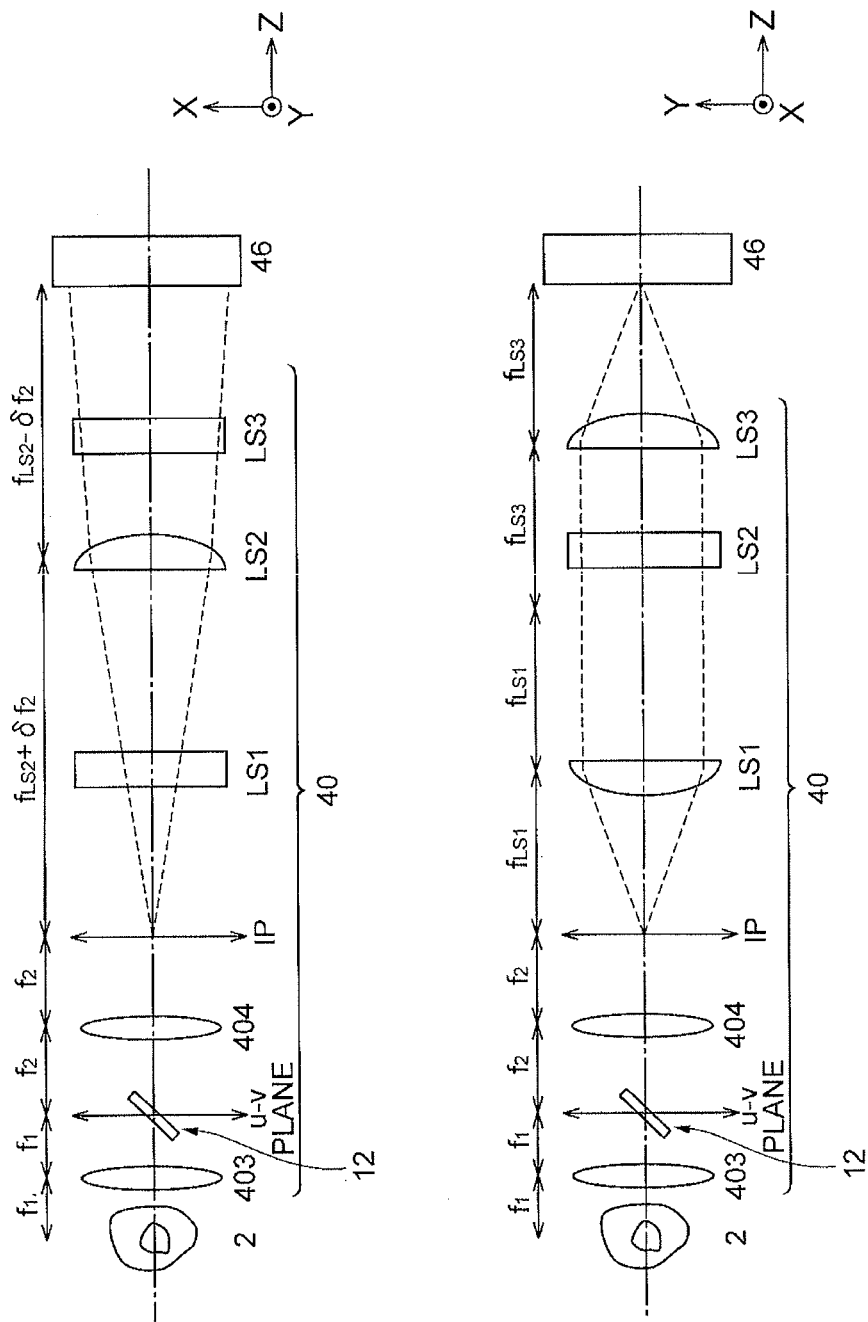
FIG. 43 is a diagram illustrating a structural example of the lens 40 in a fourteenth arrangement example.

FIG. 43 illustrates details of the lens 40 in the fourteenth arrangement example. In the fourteenth arrangement example, the lens 40 is constructed by five lenses composed of the lenses 403, 404 constituting the lens 40 used in the second arrangement example and additional lenses LS1, LS2, LS3. In the five lenses constituting the lens 40, the lenses 403, 404 are spherical lenses, while the lenses LS1, LS2, LS3 are cylindrical lenses. In the image-forming action by the lens, these cylindrical lenses exhibit different actions in the x and y directions. The beam splitter 12 is arranged on the back focal plane of the lens 403 constituting the lens 40 so as to split the substantially zero-order light in two. The light reflected by the beam splitter 12 is fed to the lens 60 as the second light.

In the x direction, the lenses LS1, LS3 have no curvature and thus do not contribute to forming images. Therefore, the lens structure in the x direction is equivalent to a structure in which only the lenses 403, 404, LS2 are arranged as illustrated in the upper side of FIG. 43. In the y direction, on the other hand, the lens LS2 has no curvature and thus does not contribute to forming images. Therefore, the lens structure in the y direction is equivalent to a structure in which only the lenses 403, 404, LS1, LS3 are arranged as illustrated in the lower side of FIG. 43.

In the x direction, an image of the object 2 is once formed on a plane IP by the lenses 403, 404. The front focal plane of the lens LS2 differs from the plane IP of the image of the object 2, while the back focal plane of the lens LS2 differs from the light-receiving surface of the photodetector 46. Therefore, a Fresnel diffraction image of the image is formed on the light-receiving surface. In the y direction, on the other hand, an image of the object 2 is once formed on the plane IP by the lenses 403, 404. The lenses LS1, LS3 constitute a so-called 4f optical system. The 4f optical system is an optical system in which the back focal plane of the lens LS1 coincides with the front focal plane of the lens LS3, so that an image of the front focal plane of the lens LS1 is formed on the back focal plane of the lens LS3. Thus, the Fresnel diffraction image and image of the object 2 are formed on the light-receiving surface of the photodetector 46 in the x and y directions, respectively, by the lens 40.

A method of processing a signal obtained in the photodetector 46 by thus constructed lens 40 will now be explained. Let the coordinate system on the light-receiving surface of the photodetector 46 be the u"v" plane as in the third or sixth arrangement example. In the third or sixth arrangement example, Fresnel diffraction images of the object 2 appear on the u"v" plane in the u" and v" directions. In the fourteenth arrangement example, the Fresnel diffraction image and image of the object 2 appear in the u" and v" directions, respectively. Let $s_{14}(u", t)$ be a signal representing the sum of signals on a line parallel to the v" direction. The arithmetic processing for obtaining the complex amplitude image $g(\xi,$ η) according to $s_{14}(u'', t)$ issued from the photodetector 46 and the arithmetic device structure for performing this processing are the same as the arithmetic processing for obtaining the complex amplitude image $g(\xi, \eta)$ according to $s_3(u'', t)$ or $s_6(u'', t)$ obtained by the third or sixth arrangement example and the arithmetic device structure for performing this processing. Therefore, the arithmetic processing for obtaining the complex amplitude image $g(\xi, \eta)$ according to $s_{14}(u'', t)$ issued from the photodetector 46 and the arithmetic device structure for performing this processing will not be explained.

Fifteenth Arrangement Example

The fifteenth arrangement example will now be explained. The fifteenth arrangement example is the same as the third or sixth arrangement example except for the structure of the lens 40. In the fifteenth arrangement example, the light-receiving surface of the photodetector 46 is arranged on a plane where a Fresnel diffraction image of the object 2 is formed in the x direction (first direction) by the lens 40, which is also a plane where a Fresnel diffraction image of the object 2 is formed in the y direction (second direction). The lens 40 in the fifteenth arrangement example is arranged between the object 2 and the photodetector 46.

Figure 44:
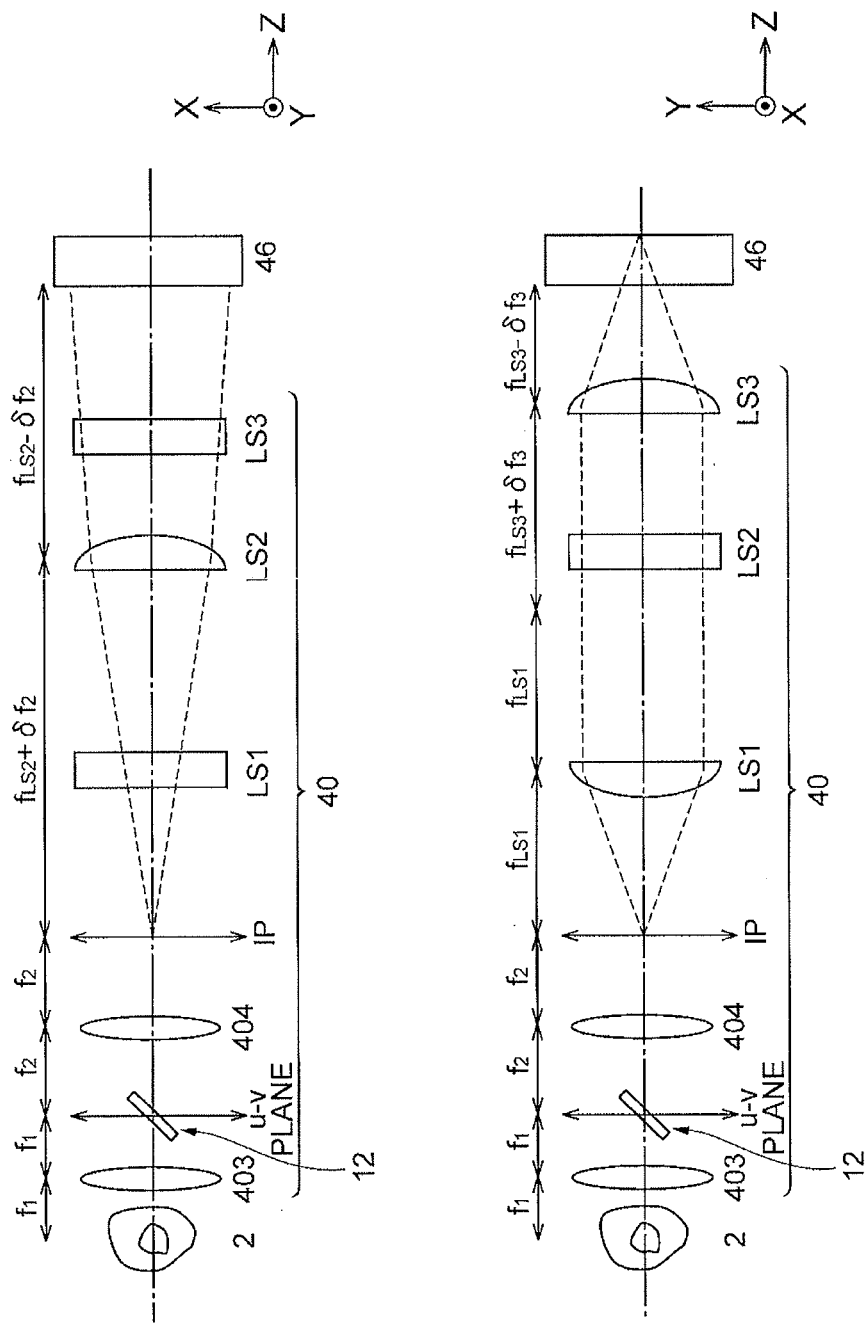
FIG. 44 is a diagram illustrating a structural example of the lens 40 in a fifteenth arrangement example.

FIG. 44 illustrates details of the lens 40 in the fifteenth arrangement example. In the fifteenth arrangement example, the lens 40 is constructed by five lenses composed of the lenses 403, 404 constituting the lens 40 used in the second arrangement example and additional lenses LS1, LS2, LS3. In the five lenses constituting the lens 40, the lenses 403, 404 are spherical lenses, while the lenses LS1, LS2, LS3 are cylindrical lenses. In the image-forming action by the lens, these cylindrical lenses exhibit different actions in the x and y directions. The beam splitter 12 is arranged on the back focal plane of the lens 403 constituting the lens 40 so as to split the substantially zero-order light in two. The light reflected by the beam splitter 12 is fed to the lens 60 as the second light.

In the x direction, the lenses LS1, LS3 have no curvature and thus do not contribute to forming images. Therefore, the lens structure in the x direction is equivalent to a structure in which only the lenses 403, 404, LS2 are arranged as illustrated in the upper side of FIG. 44. In the y direction, on the other hand, the lens LS2 has no curvature and thus does not contribute to forming images. Therefore, the lens structure in the y direction is equivalent to a structure in which only the lenses 403, 404, LS1, LS3 are arranged as illustrated in the lower side of FIG. 44.

In the x direction, an image of the object 2 is once formed on a plane IP by the lenses 403, 404. The front focal plane of the lens LS2 differs from the plane IP of the image of the object 2, while the back focal plane of the lens LS2 differs from the light-receiving surface of the photodetector 46. Therefore, a Fresnel diffraction image of the image is formed on the light-receiving surface. In the y direction, on the other hand, an image of the object 2 is once formed on the plane IP by the lenses 403, 404. The lenses LS1, LS3 do not construct a so-called 4f optical system. That is, as illustrated in the lower side of FIG. 44, the front focal plane of the lens LS3 does not coincide with the back focal plane of the lens LS1. Therefore, none of images of the object 2 and Fraunhofer diffraction images thereof is formed on the light-receiving surface. Thus, the Fresnel diffraction images of the object 2 are formed on the light-receiving surface of the photodetector 46 in both of the x and y directions by the lens 40.

A method of processing a signal obtained in the photodetector 46 by thus constructed lens 40 will now be explained. Let the coordinate system on the light-receiving surface of the photodetector 46 be the $u''v''$ plane as in the third or sixth arrangement example. In the third or sixth arrangement example, Fresnel diffraction images of the object 2 appear on the $u''v''$ plane in the $u''$ and $v''$ directions. The Fresnel diffraction images of the object 2 also appear in the $u''$ and $v''$ directions in the fifteenth arrangement example. The fifteenth arrangement example differs from the third or sixth arrangement example in the structure of the lens 40. Let $s_{15}(u'', t)$ be a signal representing the sum of signals on a line parallel to the $v''$ direction. The arithmetic processing for obtaining the complex amplitude image $g(\xi, \eta)$ according to $s_{15}(u'', t)$ issued from the photodetector 46 and the arithmetic device structure for performing this processing are the same as the arithmetic processing for obtaining the complex amplitude image $g(\xi, \eta)$ according to $s_3(u'', t)$ or $s_6(u'', t)$ obtained by the third or sixth arrangement example and the arithmetic device structure for performing this processing. Therefore, the arithmetic processing for obtaining the complex amplitude image $g(\xi, \eta)$ according to $s_{15}(u'', t)$ issued from the photodetector 46 and the arithmetic device structure for performing this processing will not be explained.

Figure 45:
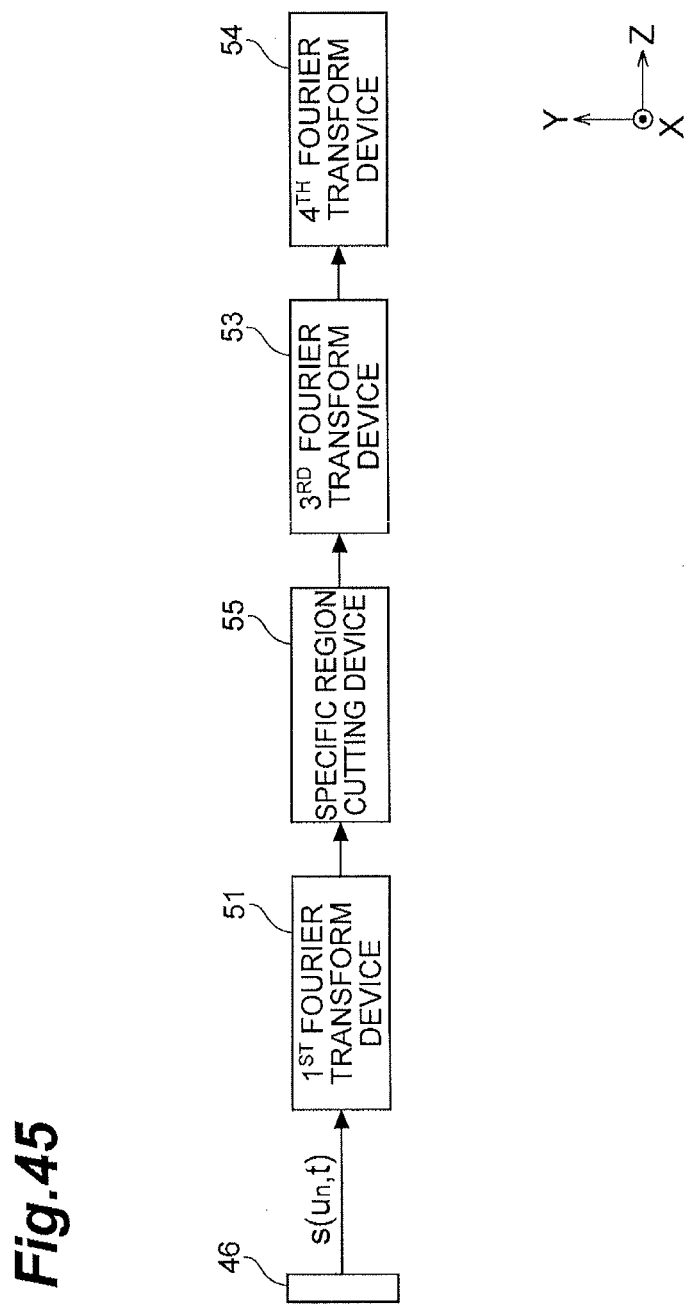
FIG. 45 is a block diagram illustrating a schematic arithmetic device structure in the first to fifteenth arrangement examples.

As illustrated in FIG. 45, the arithmetic unit 50 in each of the first to fifteenth arrangement examples is constituted by a first Fourier transform device 51 which is an arithmetic device for performing a one-dimensional Fourier transform with respect to the time variable t, a specific region cutting device 55 which is an arithmetic device for cutting out data of a region including the range of a Nyquist frequency $f_{nyq}$ about the difference frequency $\Delta f$ acting as the center, a third Fourier transform device 53 which is an arithmetic device for performing a one-dimensional Fourier transform with respect to the temporal frequency, and a fourth Fourier transform device 54 which is an arithmetic device for performing a one-dimensional Fourier transform with respect to the first direction. The four kinds of arithmetic devices mentioned above will also be collectively referred to as basic arithmetic devices in the following in this specification.

In each of the first to fifteenth arrangement examples, photodetectors 46 and arithmetic units 50 are arranged in parallel in a direction (X direction) perpendicular to the sheet of FIG. 45. In the photodetectors 46 and arithmetic units 50 arranged in parallel, FIG. 45 illustrates the photodetector 46 and arithmetic unit 50 at position $u_n$. Each of FIGS. 46 to 50, 56, 61, and 62 in the following also illustrates one set of the photodetector 46 and arithmetic unit 50 at the position $u_n$ among the photodetectors 46 and arithmetic units 50 arranged in parallel in a direction (X direction) perpendicular to the drawing sheet. The position $u_n$ will also be written as $u'_n$ and $u''_n$ according to the arrangement examples.

Sixteenth Arrangement Example

The sixteenth arrangement example will now be explained. The sixteenth arrangement example differs from the first to fifteenth arrangement examples in that it includes a plurality of photodetectors 46 and a summing device (summing device) 58 for yielding the sum of outputs from the plurality of photodetectors 46. Consequently, the sixteenth arrangement example differs from the first to fifteenth arrangement examples in the arrangement of the basic arithmetic devices.

The sixteenth arrangement example is constituted by one light source 10, one lens 40, M (M>1) photodetectors 46 (a plurality of detectors), and an arithmetic unit 50 including a plurality of basic arithmetic devices and a summing device 58.

In the sixteenth arrangement example, the M photodetectors 46 are arranged in a row in the second direction. The m-th photodetector 46m in the second direction outputs data representing the sum in the second direction at each position of the first direction at each time.

The arithmetic unit 50 in the sixteenth arrangement example includes the summing device 58 that is an arithmetic device for receiving outputs of the M photodetectors arranged in a row in the second direction and issuing the sum of 1 to M. The summing device 58 may receive outputs of M basic arithmetic devices inputting outputs of the M photodetectors 46 arranged in a row in the second direction and issue the sum of 1 to M.

Figure 46:
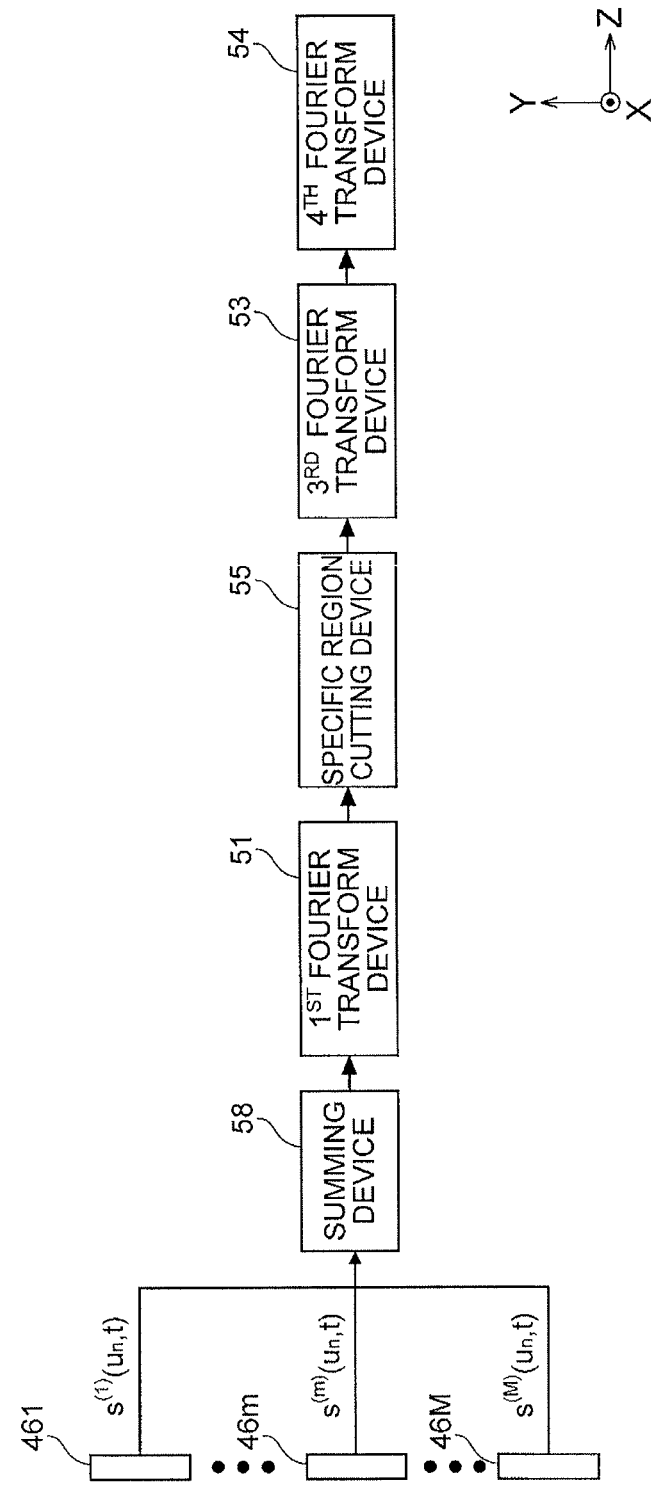
FIG. 46 is a block diagram illustrating a schematic arithmetic device structure in a sixteenth arrangement example.

When located in front of the first Fourier transform device 51 as illustrated in FIG. 46, the summing device 58 receives M signals issued from the M photodetectors. The summing device 58 also obtains the sum of 1 to M for the M signals at each time and outputs the result at each time.

Figure 47:
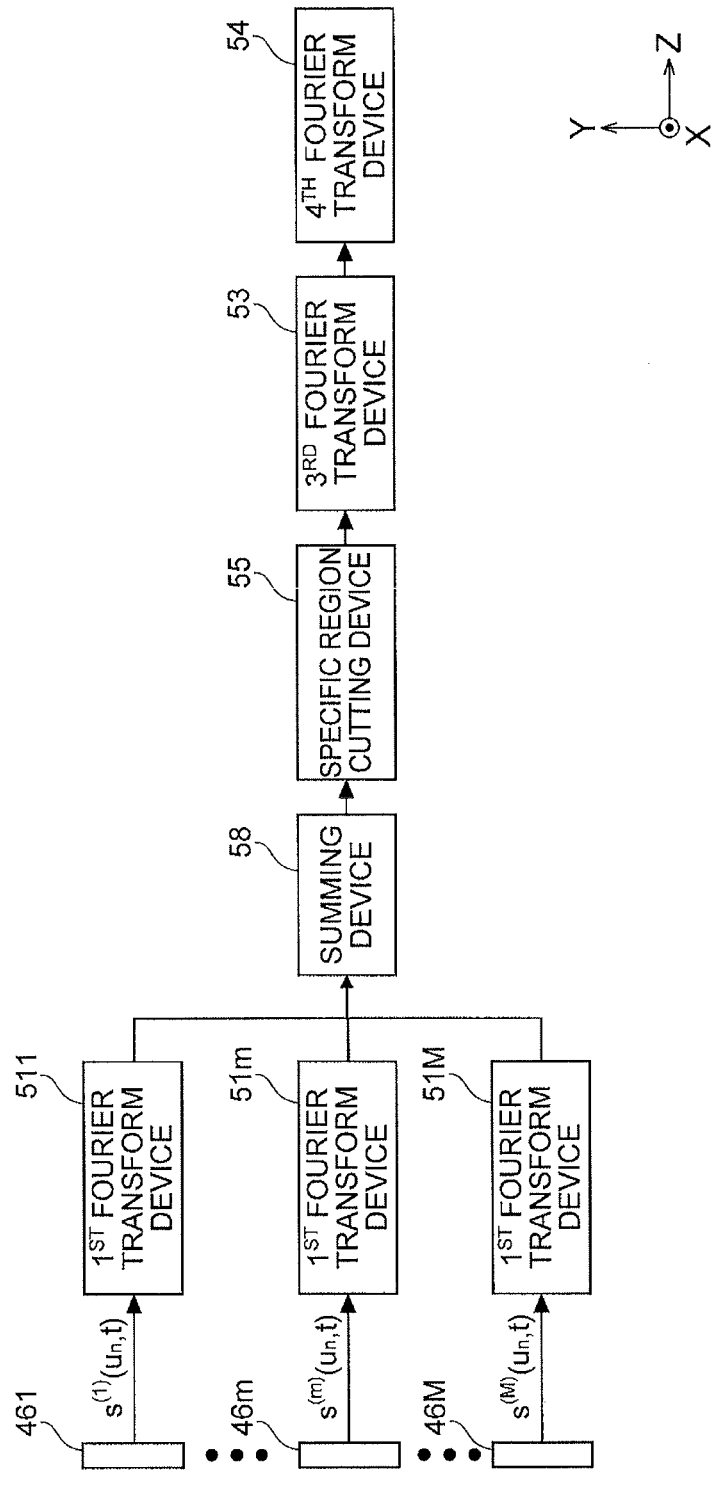
FIG. 47 is a block diagram illustrating a modified example of the schematic arithmetic device structure in the sixteenth arrangement example.
Figure 48:
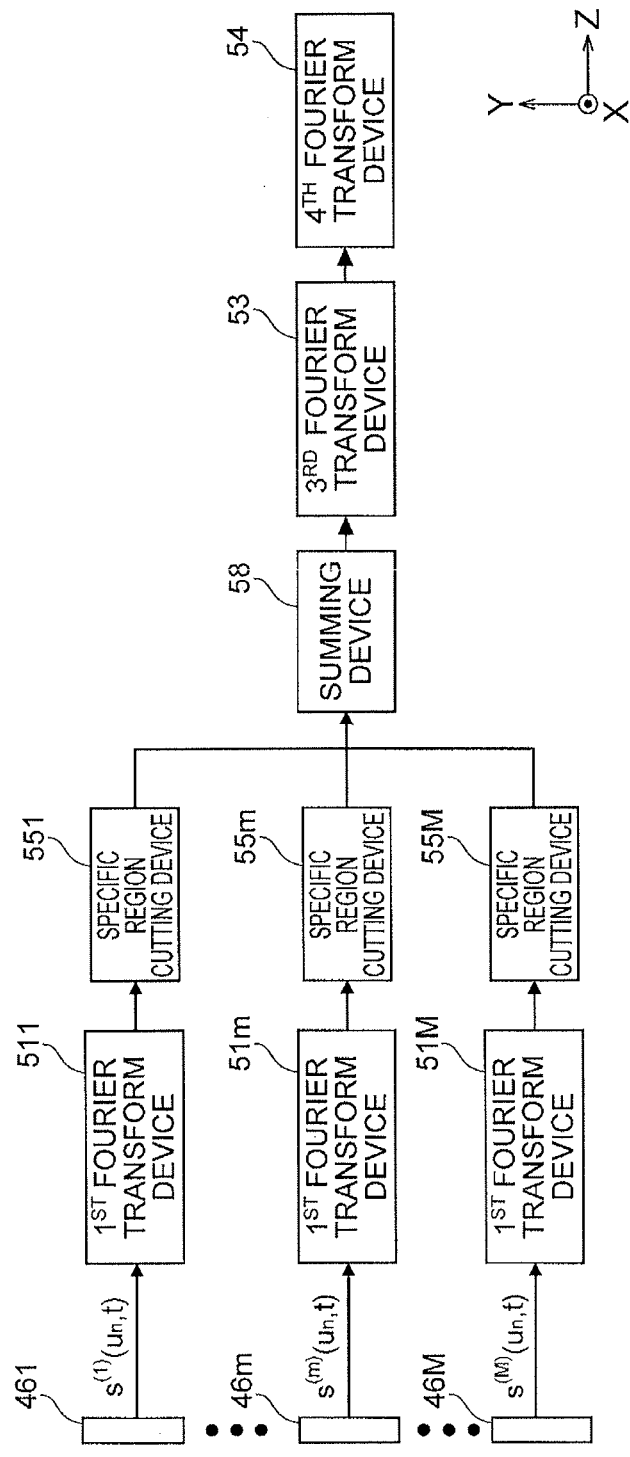
FIG. 48 is a block diagram illustrating a modified example of the schematic arithmetic devic structure in the sixteenth arrangement example.

When located between the first and third Fourier transform devices 51, 53 as illustrated in FIGS. 47 and 48, the summing device 58 receives M signals issued from the first Fourier transform device 51. The summing device 58 also obtains the sum of 1 to M for the M signals at each temporal frequency and outputs the result at each temporal frequency.

Figure 49:
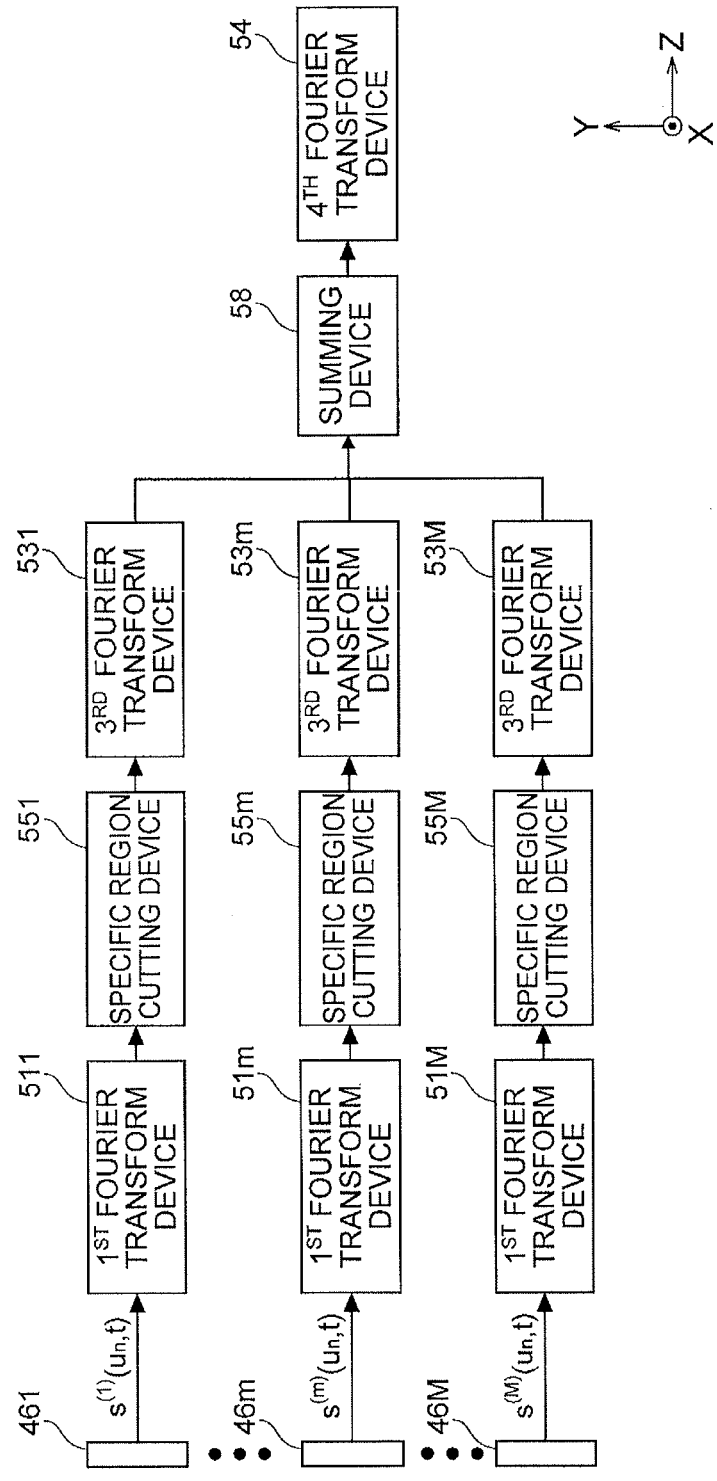
FIG. 49 is a block diagram illustrating a modified example of the schematic arithmetic device structure in the sixteenth arrangement example.
Figure 50:
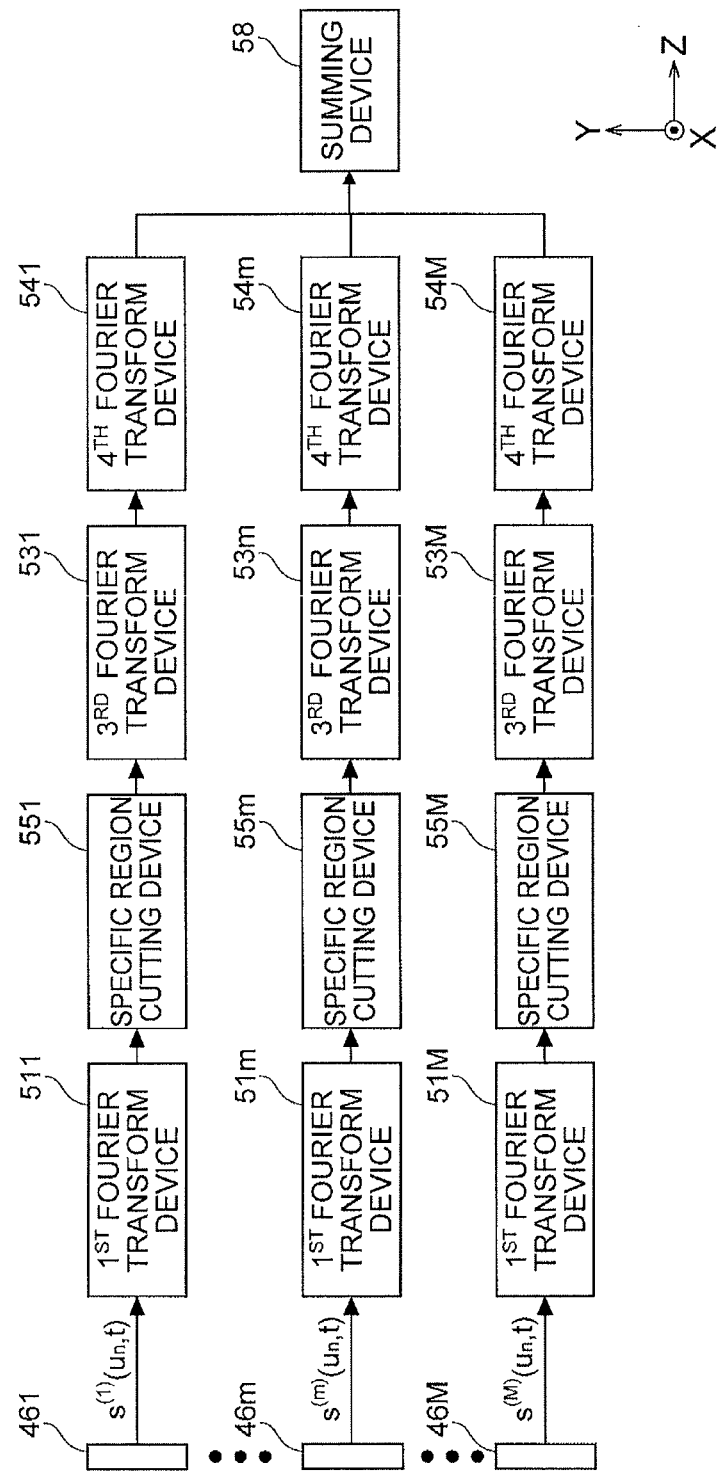
FIG. 50 is a block diagram illustrating a modified example of the schematic arithmetic device structure in the sixteenth arrangement example.

When located behind the third Fourier transform device 53 as illustrated in FIGS. 49 and 50, the summing device 58 receives M signals issued from the third Fourier transform device 53. The summing device 58 also obtains the sum of 1 to M for the M signals at each time and outputs the result at each time.

The output of the summing device 58 will now be explained. When located between the first and third Fourier transform devices 51, 53, the summing device 58 obtains the sum of 1 to M according to the following expression (24) at each temporal frequency $\omega(=\Delta\omega+\omega_d)$. Here, $S^{(m)}(u, \omega)$ represents the output signal of the first Fourier transform device 51 receiving output data $s^{(m)}(u, t)$ of the m-th detector arranged in the second direction and Fourier-transforming them with respect to the time variable t. Due to the linearity of the Fourier transform, the Fourier transform operator $FT_t$ in the middle of the expression (24) is exchangeable with the summation operator $\Sigma$, whereby the rightmost side of the expression (24) is obtained.

[Math. 24]

$$\sum_{m=1}^{M} S^{(m)}(u, \omega) = \sum_{m=1}^{M} FT_t[s^{(m)}(u, t)] \quad (24)$$
$$= FT_t\left[\sum_{m=1}^{M} s^{(m)}(u, t)\right]$$

The term on which the one-dimensional Fourier transform operator $FT_t$ with respect to the time variable t acts in the rightmost side represents the sum s(u, t) of 1 to M of the waveforms $s^{(m)}(u, t)$ issued from the M photodetectors. That is, the summing device 58 provided in the arithmetic unit sends out the output of the first Fourier transform device 51 receiving the signals issued from any of the detectors in the first to fifteenth arrangement examples. Therefore, the sixteenth arrangement example can also be regarded as a structure in which a part of the detector outputting the sum of the signals in the second direction at each time is included in the arithmetic unit.

When located behind the third Fourier transform device 53, on the other hand, the summing device 58 obtains the sum of 1 to M according to the following expression (25) at each time. Here, $s'^{(m)}(u, t)$ represents the output data of the third Fourier transform device 53m. The output of the m-th detector arranged in the second direction is connected to the input of the third Fourier transform device 53m through the first Fourier transform device 51m and specific region cutting device 55m. The one-dimensional Fourier transform of $s'^{(m)}(u, t)$ with respect to the time variable t is $S'^{(m)}(u, \omega_d)$. The term on which the one-dimensional Fourier transform operator $FT_\omega$ acts in the right side of the expression (25) represents output data of the specific region cutting device 55. Therefore, the input of the specific region cutting device 55 is a signal $S^{(m)}(u, \Delta\omega+\omega_d)$ whose frequency is shifted by the difference frequency $\Delta\omega$ indicated in the left side of the expression (26). The rightmost side of the expression (26) represents the sum of 1 to M of the waveforms $s^{(m)}(u, t)$ issued from the M photodetectors.

[Math. 25]

$$\sum_{m=1}^{M} s'^{(m)}(u, t) = \sum_{m=1}^{M} FT_\omega^{-1}[S'^{(m)}(u, \omega_d)] \quad (25)$$

[Math. 26]

$$\sum_{m=1}^{M} FT_\omega^{-1}[S^{(m)}(u, \Delta\omega + \omega_d)] = \sum_{m=1}^{M} s^{(m)}(u, t) \quad (26)$$
$$= s(u, t)$$

That is, the output of the summing device 58 provided in the arithmetic unit coincides with the signal issued from the detector in each of the first to fifteenth arrangement example, whereby the sixteenth arrangement example can be regarded as a structure in which a part of the detector outputting the sum of the signals in the second direction at each time is included in the arithmetic unit.

An example of the sixteenth arrangement example will now be explained. The lens 40 similar to that in the first arrangement example illustrated in FIG. 12 was used in the sixteenth arrangement example. That is, the light-receiving surface of the photodetector 46 was arranged on the back focal plane in the first direction of the lens 40, which was also the back focal plane in the second direction of the lens 40. As the photodetector 46, a digital CCD camera equipped with two-dimensionally arranged 640×480 pixels, each having a pixel size of 8.3×8.3 μm, was used. Its frame rate $f_{CCD}$ was 30 Hz. Let m and n be the pixel numbers in the v and u directions, respectively. The photodetector 46 was arranged such that an object moved in a direction parallel to the v direction. Only a region having 312×312 pixels in the 640×480 pixels in total of the photodetector 46 was used for an experiment. Therefore, M=N=312. Here, M and N represent the numbers of pixels in the vertical and horizontal directions, respectively, while their lower-case letters m and n indicate their corresponding pixel numbers.

Figure 51:
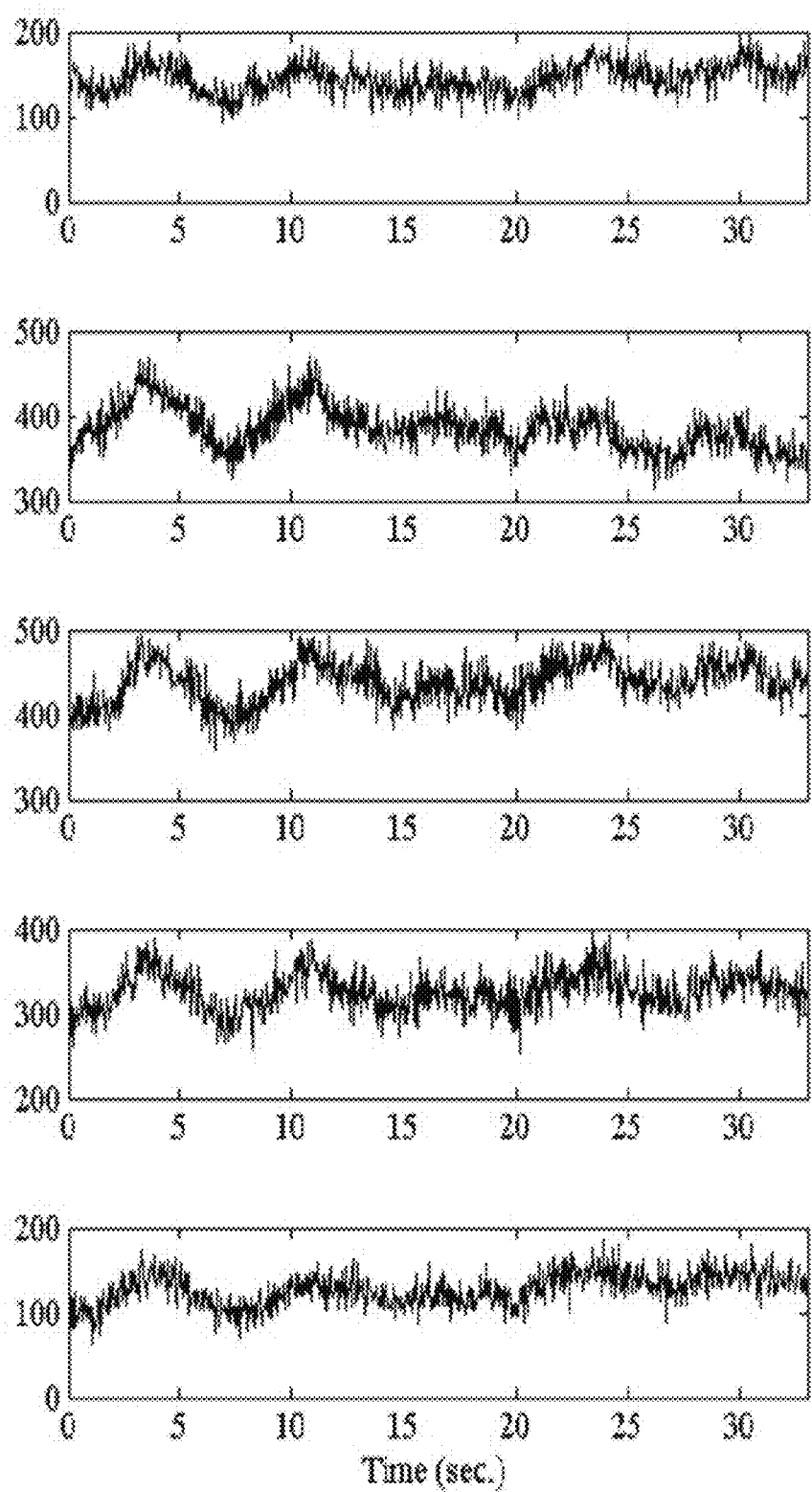
FIG. 51 is a graph illustrating a temporal waveform $s^{(m)}(u, t)$ in the sixteenth arrangement example.
Figure 52:
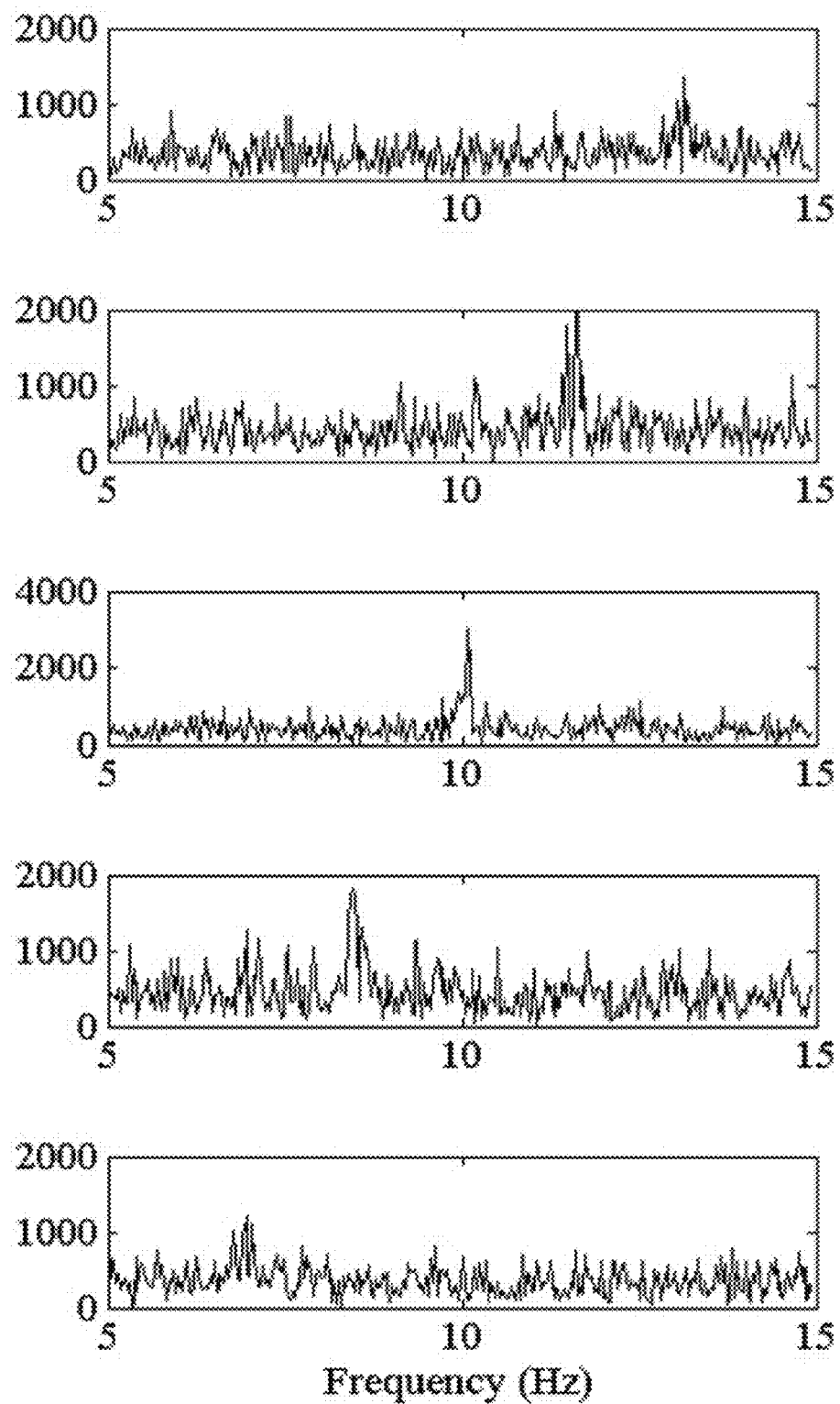
FIG. 52 is a graph illustrating a frequency spectrum $S^{(m)}(u, \omega)$ in the sixteenth arrangement example.

That is, the photodetector 46 in the sixteenth arrangement example is a photodetector in which M one-dimensional line sensors, each comprising N light-receiving pixels $d_n^{(m)}$ arranged in the first direction, are arranged in the second direction. Let $S^{(m)}(u, \omega)$ be the waveform obtained after Fourier-transforming the temporal waveform $s^{(m)}(u, t)$ issued from each light-receiving pixel $d_n^{(m)}$ with respect to the time variable t. FIG. 51 represent the temporal waveforms $s^{(m)}(u, t)$. FIG. 52 represents $S^{(m)}(u, \omega)$.

Figure 53:
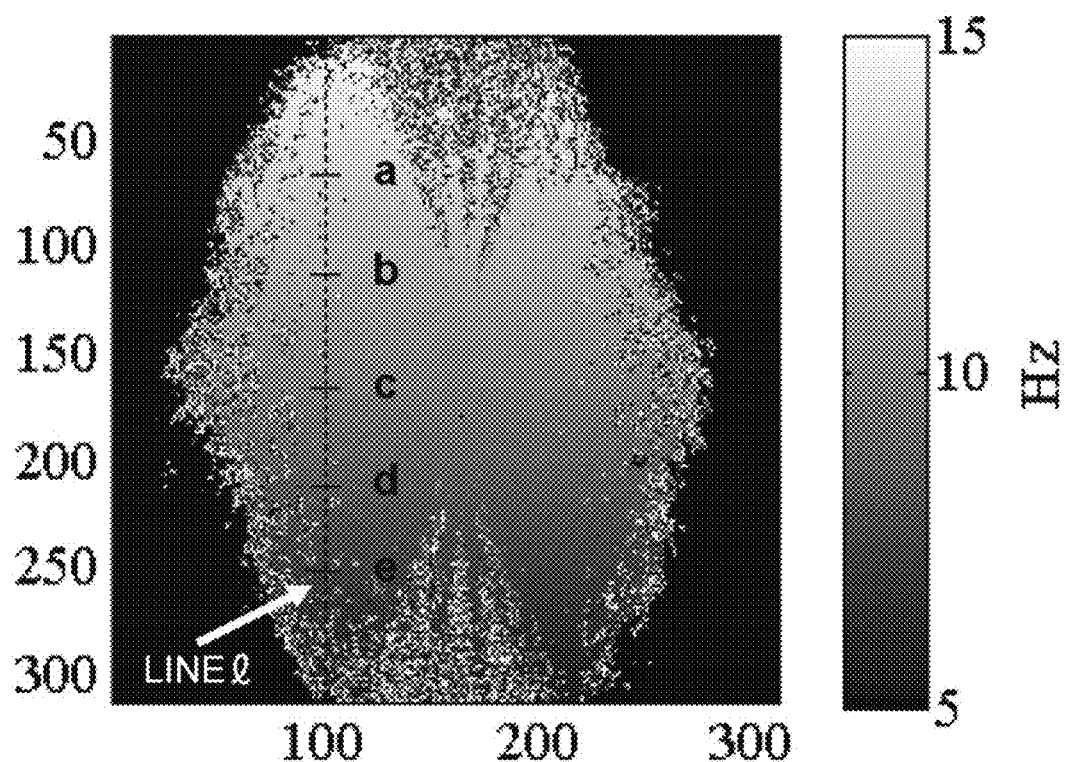
FIG. 53 is a chart illustrating a frequency having the maximum amplitude at each position (m, n) in pseudocolor display.
Figure 54:
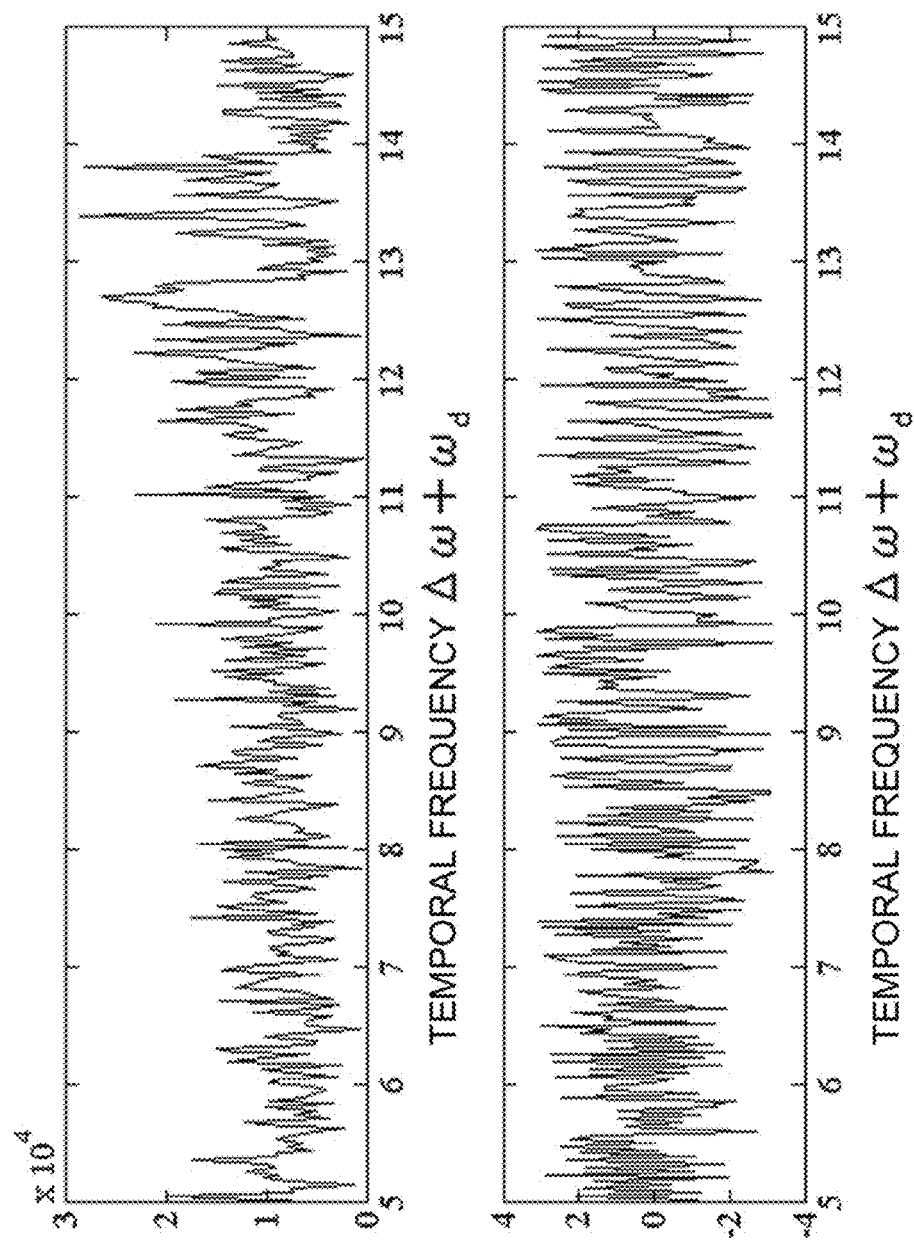
FIG. 54 is a chart illustrating the amplitude and phase of a frequency spectrum $S(u_1, \omega)$ as a result of summing signals from the pixels on a line 1.

FIG. 53 is a chart illustrating a frequency having the maximum amplitude at each position (m, n) in the temporal frequency spectrum $S^{(m)}(u, \omega)$ in pseudocolor display. In FIG. 53, a) to e) are observation points of the waveforms represented in FIGS. 51 and 52. FIG. 54 illustrates results of output at each temporal frequency from the summing device 58 having received the output $S^{(m)}(u_1, \omega)$ on a line 1 (position $u_1$) in the output of the first Fourier transform device 51 and yielded the sum of $S^{(m)}(u_1, \omega)$ on the line 1 at each temporal frequency.

Figure 55:
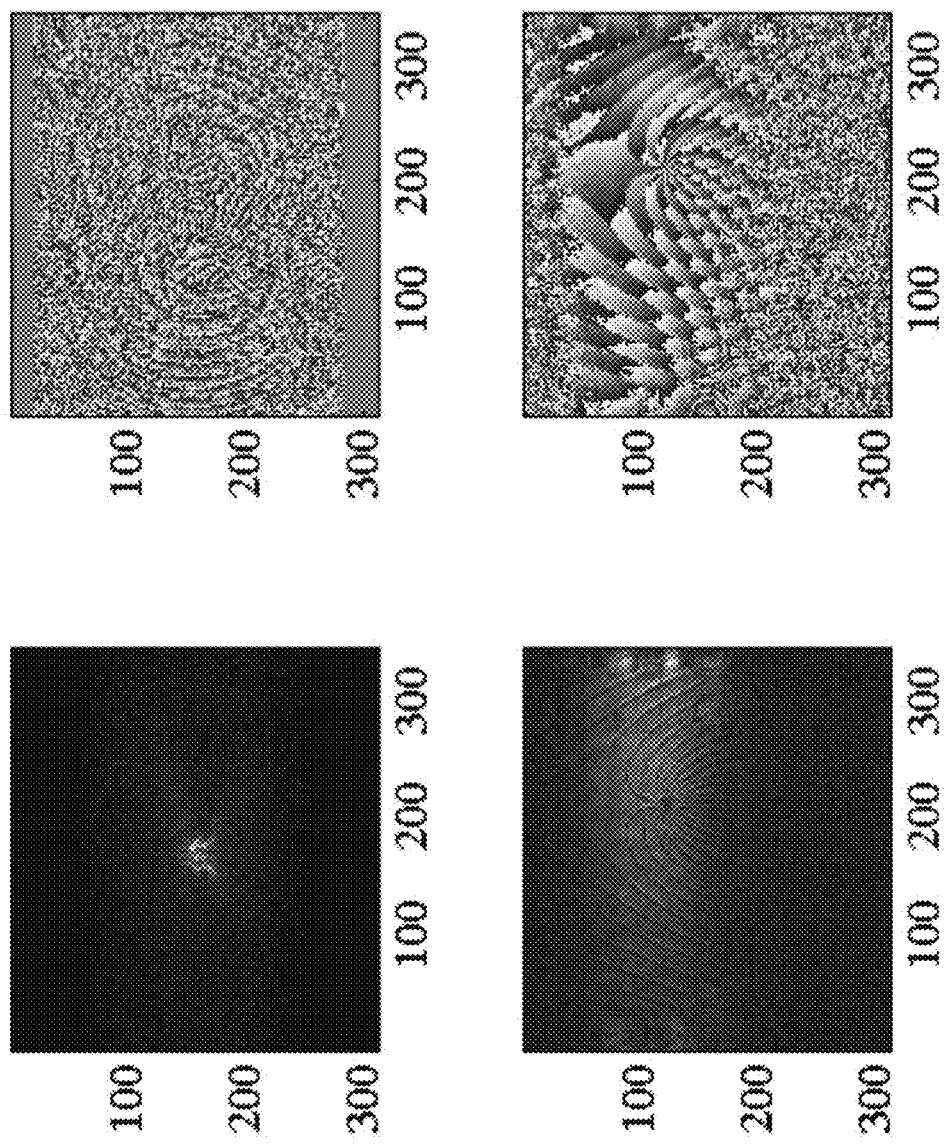
FIG. 55 is a diagram illustrating $G(u, 107_d)$ and complex amplitude image g in the sixteenth arrangement example.

From the expression (24), the output of the summing device 58 corresponds to $G(u, \Delta\omega+\omega_d)$ in the first arrangement example, so that the method of operating the data $G(u, \Delta\omega+\omega_d)$ is the same as that in the first arrangement example. The upper side in FIG. 55 illustrates the amplitude image (upper left) and phase image (upper right) obtained when a frequency region including a range of a Nyquist frequency $f_{nyq}$=5 Hz in upper and lower region of $\Delta f$=10 Hz acting as the center frequency was cut out by the specific region cutting device 55. As a result, the complex amplitude image of the object 2 was obtained by arithmetic operations similar to those in the first arrangement example as illustrated in the lower side of FIG. 55.

As in the foregoing, the object 2 moving at the speed of 100 μm/sec could be captured without blurring under the conditions where $\Delta f$=10 Hz, $f_{CCD}$=30 Hz, and Nyquist frequency $f_{nyq}$=5 Hz. One still image was obtained from 1000 interference images acquired within a capture time of about 33 seconds.

Seventeenth Arrangement Example

The seventeenth arrangement example has a structure including a plurality of photodetectors 46 and the summing device 58 as in the sixteenth arrangement example. That is, the seventeenth arrangement example is constituted by one light source 10, one lens 40, M (M>1) photodetectors 46, and an arithmetic unit 50 as with the sixteenth arrangement example. The arithmetic unit 50 includes a plurality of basic arithmetic devices and a summing device 58 for yielding the sum of outputs from the photodetectors 46. That is, the seventeenth arrangement example comprises a plurality of detectors, while the arithmetic unit 50 further comprises the summing device 58 for yielding the sum of outputs from the plurality of detectors.

When the lens 40 and the arithmetic unit 50 are regarded as an arithmetic unit, the lens 40 is incorporated in the arithmetic unit in the seventeenth arrangement example. The seventeenth arrangement example has a structure in which an arithmetic device for performing a Fourier transform or Fresnel transform with respect to the second direction (hereinafter referred to as second direction converter 59) is added to the arithmetic unit 50 of the first arrangement example. The second direction converter for performing the Fourier transform or Fresnel transform with respect to the second direction corresponds to the converter recited in the claims.

Figure 56:
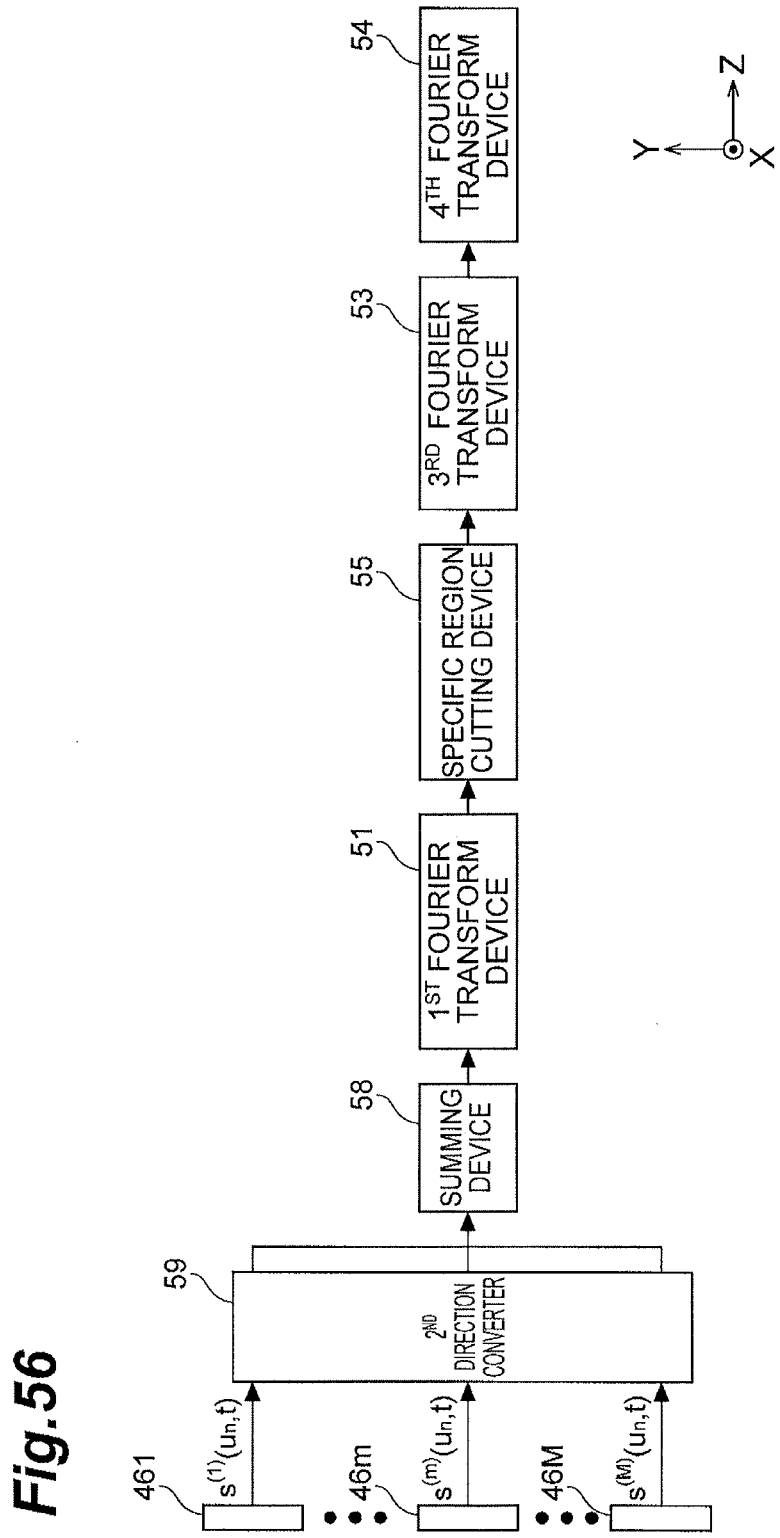
FIG. 56 is a block diagram illustrating a modified example of the schematic arithmetic device structure in an eighteenth example.
Figure 61:
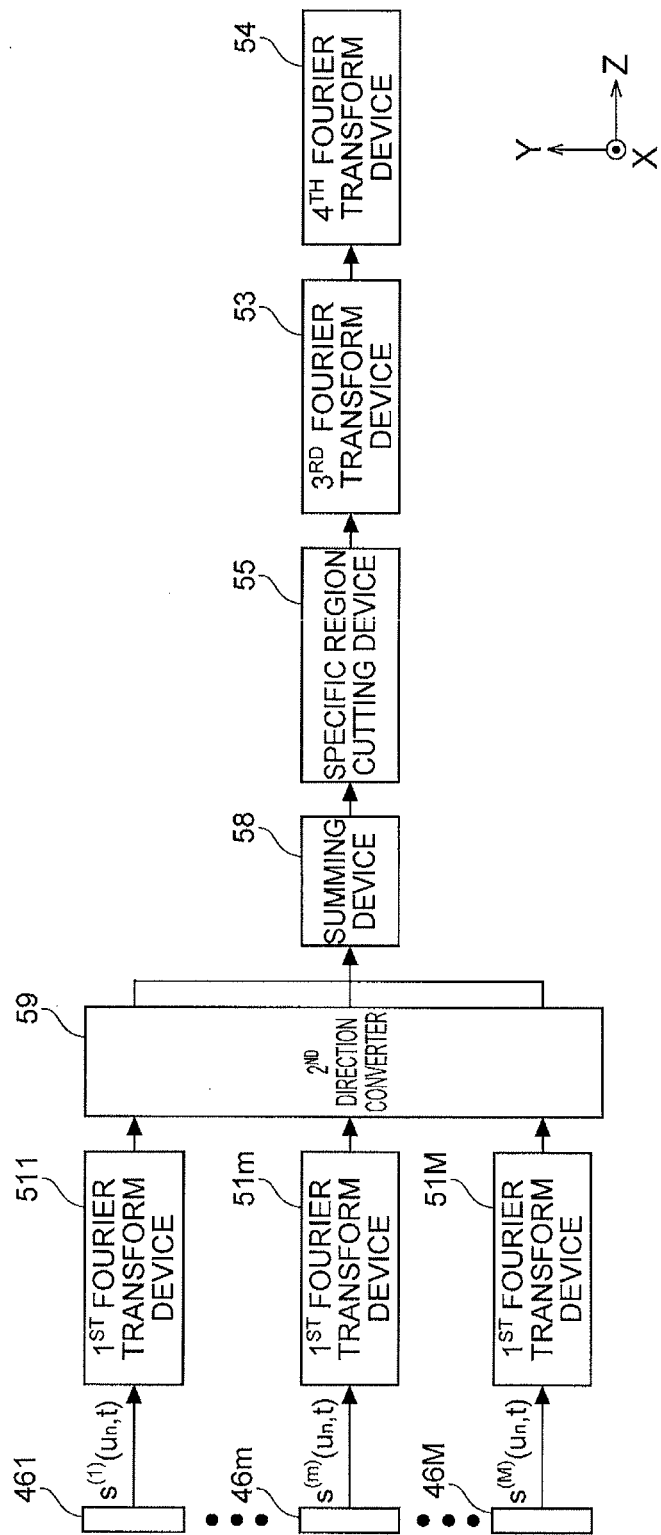
FIG. 61 is a block diagram illustrating a structure in a modified example of seventeenth to nineteenth arrangement examples.
Figure 62:
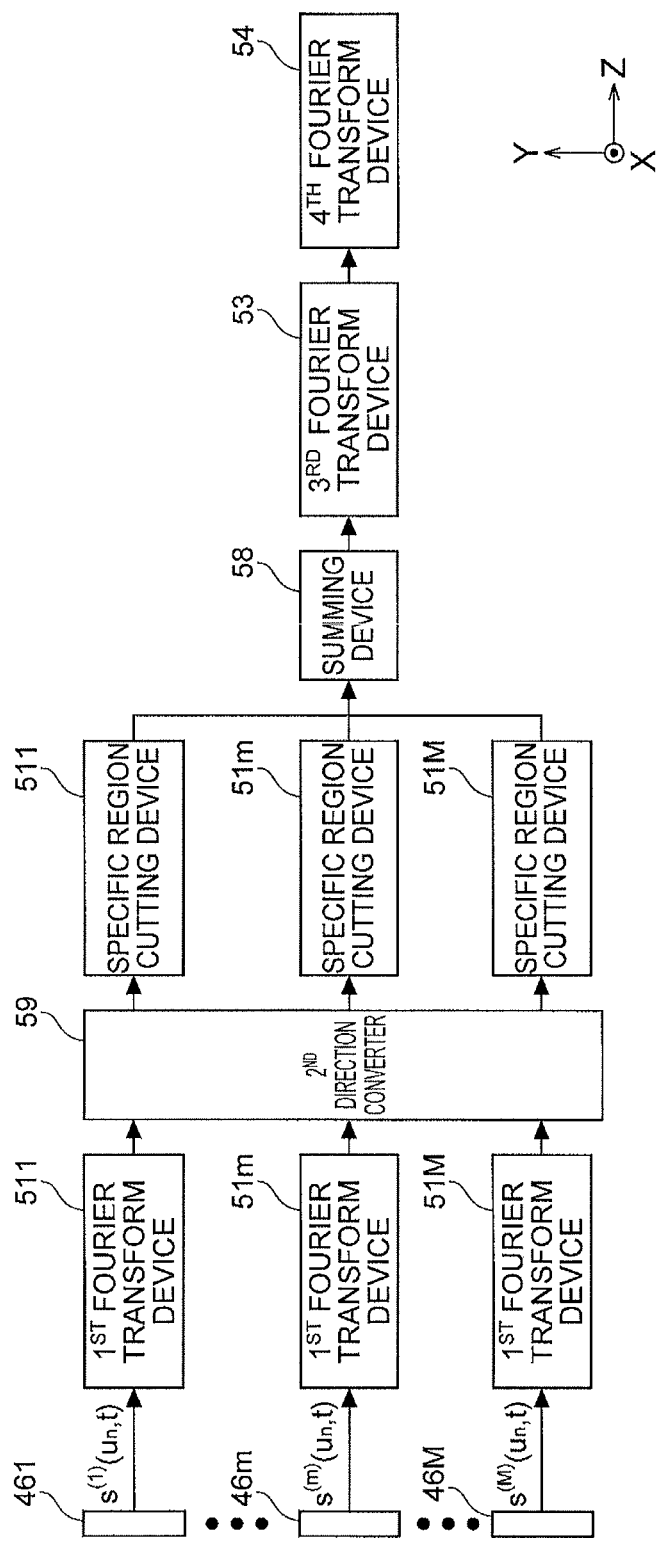
FIG. 62 is a block diagram illustrating a structure in a modified example of the seventeenth to nineteenth arrangement examples.

As illustrated in FIGS. 56, 61, and 62, the second direction converter 59 is arranged in front of the summing device 58 within the arithmetic unit 50 that receives outputs from the photodetectors 46. The second direction converter 59, regardless of its arithmetic operation position, receives M outputs at a position m ($v_m$, $v'_m$, $v''_m$) and issues the result of the arithmetic operation.

When the second direction converter 59 is a Fourier transform unit, it is equivalent to the eighth arrangement example in which a Fraunhofer diffraction image and an object image are received on the light-receiving surface of the photodetector 46 in the first and second directions, respectively. That is, the lens 40 used in the first arrangement example and the second direction converter 59 constitute the lens 40 in the eighth arrangement example.

When the second direction converter 59 is a Fresnel transform unit, it is equivalent to the ninth arrangement example in which a Fraunhofer diffraction image and a Fresnel diffraction image are received on the light-receiving surface of the photodetector 46 in the first and second directions, respectively. That is, the lens 40 used in the first arrangement example and the second direction converter 59 constitute the lens 40 in the ninth arrangement example.

Eighteenth Arrangement Example

The eighteenth arrangement example has a structure including a plurality of photodetectors 46 and the summing device 58 as in the sixteenth arrangement example. That is, the eighteenth arrangement example is constituted by one light source 10, one lens 40, M (M>1) photodetectors 46, and an arithmetic unit 50 including a plurality of basic arithmetic devices and the summing device 58 as with the sixteenth arrangement example. That is, the eighteenth arrangement example comprises a plurality of detectors, while the arithmetic unit 50 further comprises the summing device 58 for yielding the sum of outputs from the plurality of detectors.

When the lens 40 and the arithmetic unit 50 are regarded as an arithmetic unit, the lens 40 is incorporated in the arithmetic unit in the eighteenth arrangement example. The eighteenth arrangement example has a structure in which a second direction converter 59 for performing a Fourier transform or Fresnel transform with respect to the second direction (i.e., with respect to m) is added to the arithmetic unit 50 of the second arrangement example.

As illustrated in FIGS. 56, 61, and 62, the second direction converter 59 is arranged in front of the summing device 58 within the arithmetic unit 50 that receives outputs from the photodetectors. The second direction converter 59, regardless of its arithmetic operation position, receives M outputs at a position m ($v_m$, $v'_m$, $v''_m$) and issues the result of the arithmetic operation.

When the second direction converter 59 is a Fourier transform unit, it is equivalent to the tenth arrangement example in which an object image and a Fraunhofer diffraction image are received on the light-receiving surface of the photodetector 46 in the first and second directions, respectively. That is, the lens 40 used in the second arrangement example and the second direction converter 59 constitute the lens 40 in the tenth arrangement example.

When the second direction converter 59 is a Fresnel transform unit, it is equivalent to the twelfth arrangement example in which an object image and a Fresnel diffraction image are received on the light-receiving surface of the photodetector 46 in the first and second directions, respectively. That is, the lens 40 used in the second arrangement example and the second direction converter 59 constitute the lens 40 in the twelfth arrangement example.

An example of the eighteenth arrangement example will now be explained. The lens 40 similar to that in the second arrangement example illustrated in FIG. 22 was used in the eighteenth arrangement example. That is, the light-receiving surface of the photodetector 46 was arranged such that an object image was formed on the light-receiving surface of the photodetector 46 in each of the first and second directions. The second direction converter 59 received outputs from the M photodetectors at each time and fed the results of arithmetic operations to the summing device 58. FIG. 56 illustrates a block diagram of this example.

As the photodetector 46, a digital CCD camera equipped with two-dimensionally arrayed 640×480 pixels, each having a pixel size of 8.3×8.3 μm, was used. Its frame rate $f_{CCD}$ was 30 Hz. Let m and n be the pixel numbers in the v' and u' directions, respectively. The photodetector 46 was arranged such that an object moved in a direction parallel to the v' direction. Only a region having 312×312 pixels in the 640× 480 pixels in total of the photodetector 46 was used for an experiment. Therefore, M=N=312. Here, M and N represent the numbers of pixels in the vertical and horizontal directions, respectively, while their lower-case letters m and n indicate their corresponding pixel numbers.

Figure 57:
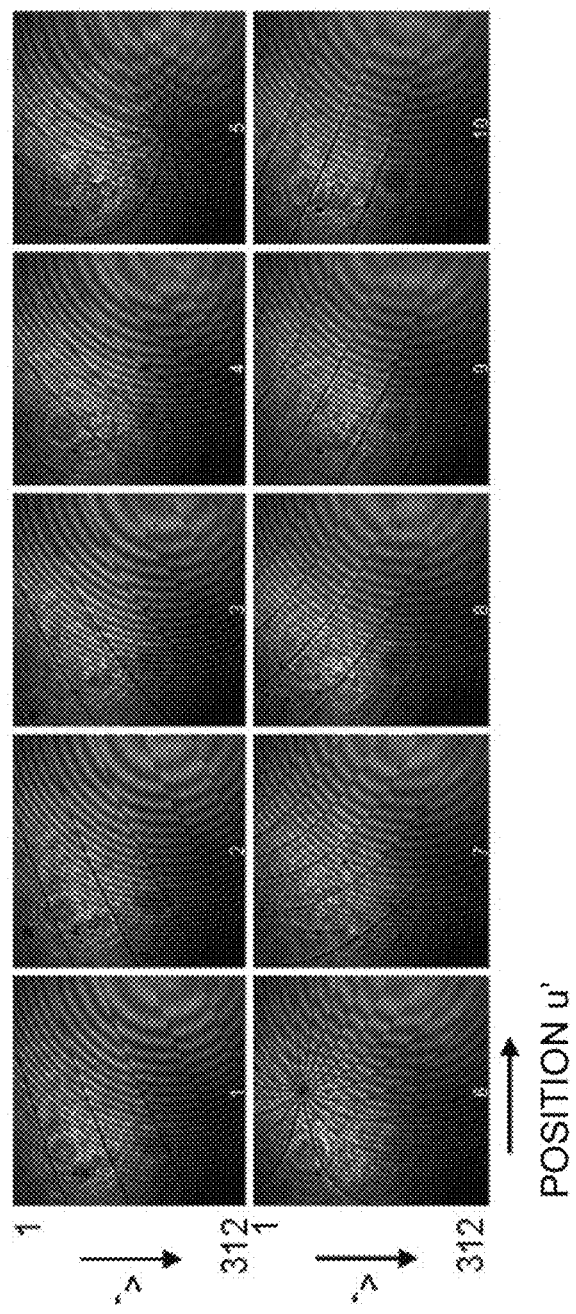
FIG. 57 is a diagram illustrating input images in a second direction converter in the eighteenth arrangement example.

In the eighteenth arrangement example, the sample illustrated in FIG. 24 was measured as the object 2. FIG. 57 illustrates M pieces of input data at the position u' fed to the second direction converter 59 at each time (numbers 1 to 10 in the diagram corresponding to times). The second direction converter 59 performed a Fourier transform.

The waveform $\mathrm{Re}[\mathrm{FT}_m[s^{(m)}(u', t)]]$ issued from the second direction converter 59 is sent to the summing device 58, where the sum is taken with respect to m, so as to yield s(u', t). $\mathrm{FT}_m$ represents a one-dimensional Fourier transform with respect to the variable m. Re is an operator for taking a real part of a complex number. Since the lens 40 used in the second arrangement example and the second direction converter 59 construct the lens 40 in the tenth arrangement example, the data issued from the summing device 58 are the same as the signals issued from the detectors in the tenth arrangement example. Since the tenth arrangement example has been explained as one in which the signals issued from its detectors are operated in the same method as in the second arrangement example, the eighteenth arrangement example yields the complex amplitude image g(ξ, η) by the arithmetic operation method of the second arrangement example.

Figure 58:
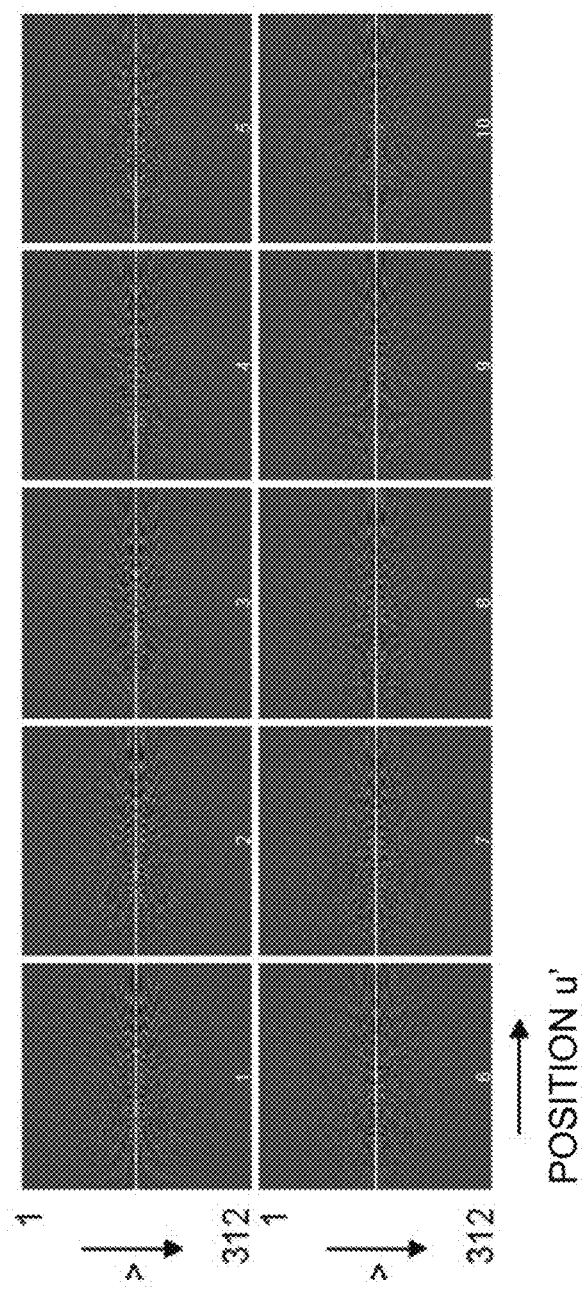
FIG. 58 is a diagram illustrating output images in the second direction converter in the eighteenth arrangement example.
Figure 59:
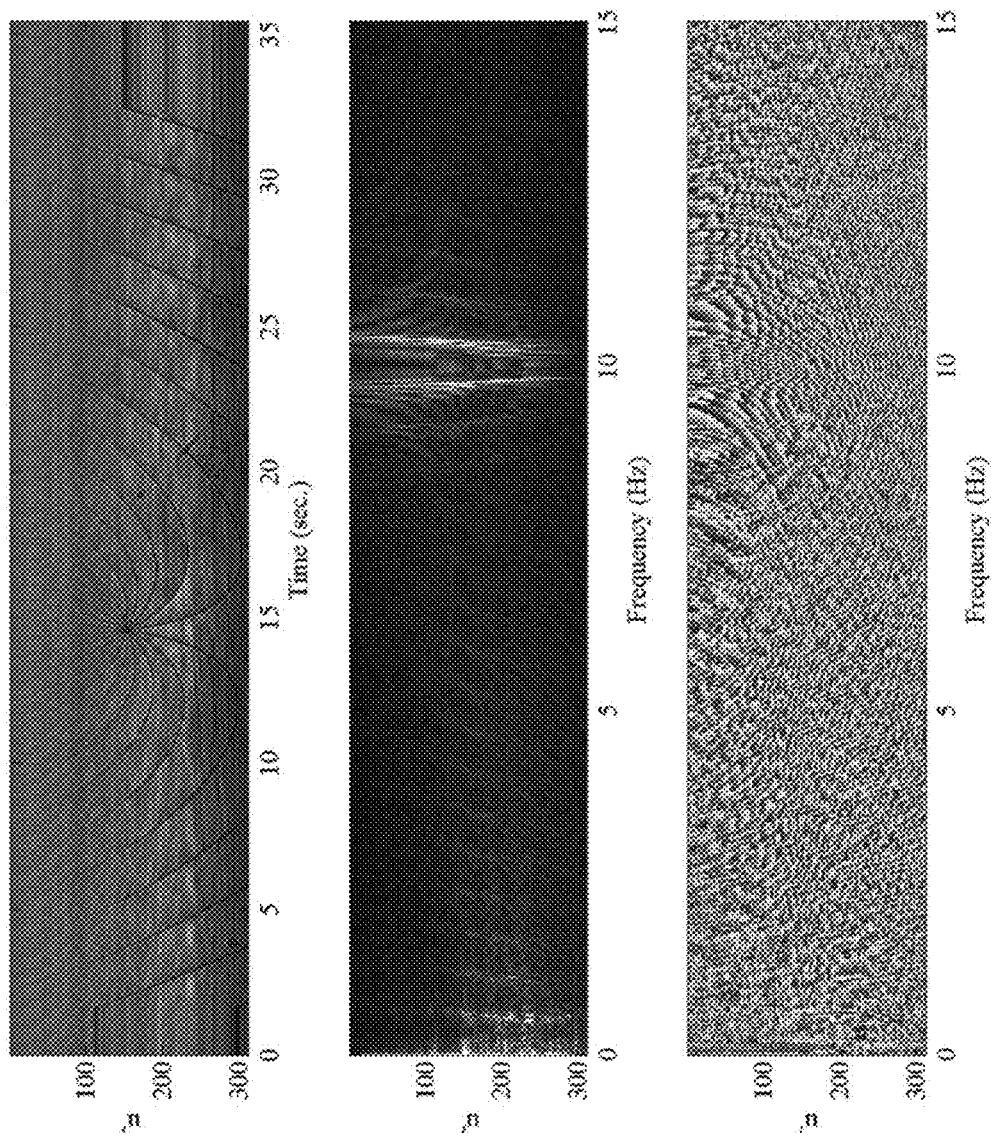
FIG. 59 is a diagram illustrating data obtained by the eighteenth example.

FIG. 57 illustrates input images of the second direction converter 59 in the eighteenth arrangement example. FIG. 58 represents M pieces of output data at the position u' issued from the second direction converter 59 at each time. The upper part of FIG. 59 illustrates data issued at each time from the summing device 58 having acquired the sum of 1 to M at each time. The middle part of FIG. 59 illustrates the amplitude image in the output one-dimensionally Fourier-transformed with respect to the time variable t by the first Fourier transform device 51. The lower side of FIG. 59 illustrates the phase image in the output one-dimensionally Fourier-transformed with respect to the time variable t by the first Fourier transform device 51.

Figure 60:
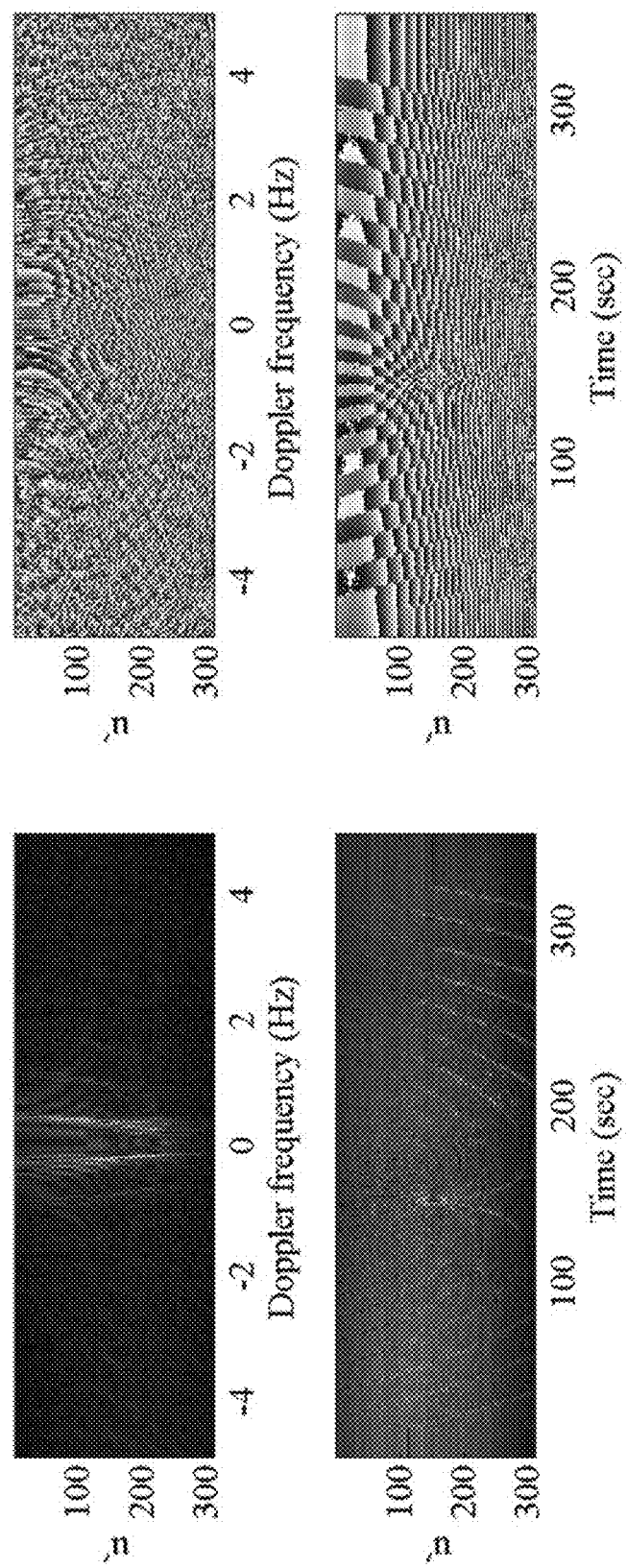
FIG. 60 is a diagram illustrating data obtained by the eighteenth example.

The upper part of FIG. 60 illustrates results of outputs from the specific region cutting device, with its left and right sides representing the amplitude image and phase image, respectively. The lower side of FIG. 60 illustrates results of a one-dimensional Fourier transform with respect to the temporal frequency by the third Fourier transform device 53, with its left and right sides representing the amplitude image and phase image, respectively.

Nineteenth Arrangement Example

The nineteenth arrangement example has a structure including a plurality of photodetectors 46 and the summing device 58 as in the sixteenth arrangement example. That is, the nineteenth arrangement example is constituted by one light source 10, one lens 40, M (M>1) photodetectors 46, and an arithmetic unit 50 including a plurality of basic arithmetic devices and the summing device 58 as with the sixteenth arrangement example. That is, the nineteenth arrangement example comprises a plurality of detectors, while the arithmetic unit 50 further comprises the summing device 58 for yielding the sum of outputs from the plurality of detectors.

When the lens 40 and the arithmetic unit 50 are regarded as an arithmetic unit, the lens 40 is incorporated in the arithmetic unit 50 in the nineteenth arrangement example. The nineteenth arrangement example has a structure in which a second direction converter 59 for performing a Fourier transform or Fresnel transform with respect to the second direction (i.e., with respect to m) is added to the arithmetic unit 50 of the third arrangement example.

As illustrated in FIGS. 56, 61, and 62, the arithmetic operation position of the second direction converter 59 is arranged in front of the summing device 58 within the arithmetic unit that receives outputs from the detectors. The second direction converter 59, regardless of its arithmetic operation position, receives M outputs at a position m ($v_m$, $v'_m$, $v''_m$) and issues the result of the arithmetic operation.

When the second direction converter 59 is a Fourier transform unit, it is equivalent to the fifteenth arrangement example in which Fresnel diffraction images are received on the light-receiving surface of the photodetector 46 in the first and second directions. That is, the lens 40 used in the third arrangement example and the second direction converter 59 constitute the lens 40 in the fifteenth arrangement example.

When the second direction converter 59 is a Fresnel transform unit, it is equivalent to the fifteenth arrangement example in which Fresnel diffraction images are received on the light-receiving surface of the photodetector 46 in the first and second directions. That is, the lens 40 used in the third arrangement example and the second direction converter 59 constitute the lens 40 in the fifteenth arrangement example.

The arithmetic operation position of the second direction converter 59 where the outputs from the photodetectors 46 are received in the arithmetic unit 50 will now be explained. It is the position of the lens 40 when the second direction converter 59 is included in the lens 40. When not included in the lens 40, the second direction converter 59 is arranged in front of the summing device 58 receiving outputs from the photodetectors 46 within the arithmetic unit 50.

When the second direction converter 59 is located between the detector and the first Fourier transform device 51, the input of the second direction converter 59 receives outputs from the M photodetectors at each time and issues the result of arithmetic operations at each time.

When the second direction converter 59 is located between the first and third Fourier transform devices 51, 53, the input of the second direction converter 59 receives outputs from the M photodetectors at each temporal frequency and issues the result of arithmetic operations at each temporal frequency.

When the second direction converter 59 is located behind the third Fourier transform device 53, the input of the second direction converter 59 receives outputs from the M photodetectors at each time and issues the result of arithmetic operations at each time.

Twentieth Arrangement Example

The twentieth arrangement example will now be explained. In the first to nineteenth arrangement examples, a method described in Literature 1 (Gabriel Popescu, "Fourier phase microscopy for investigation of biological structures and dynamics," Optics letters, 29, 2503, (2004)) was used for separating zero-order light and higher-order light (non-Doppler-shifted light and Doppler-shifted light) in the object light (scattered light from the object). That is, the lens 40 is arranged between the object 2 and the light-receiving surface of the photodetector 46. The lens 40 temporarily forms a Fraunhofer diffraction image between the object 2 and the light-receiving surface of the photodetector 46. The substantially zero-order light concentrating in the vicinity of the center of the Fraunhofer diffraction image is employed as the reference light.

Figure 63:
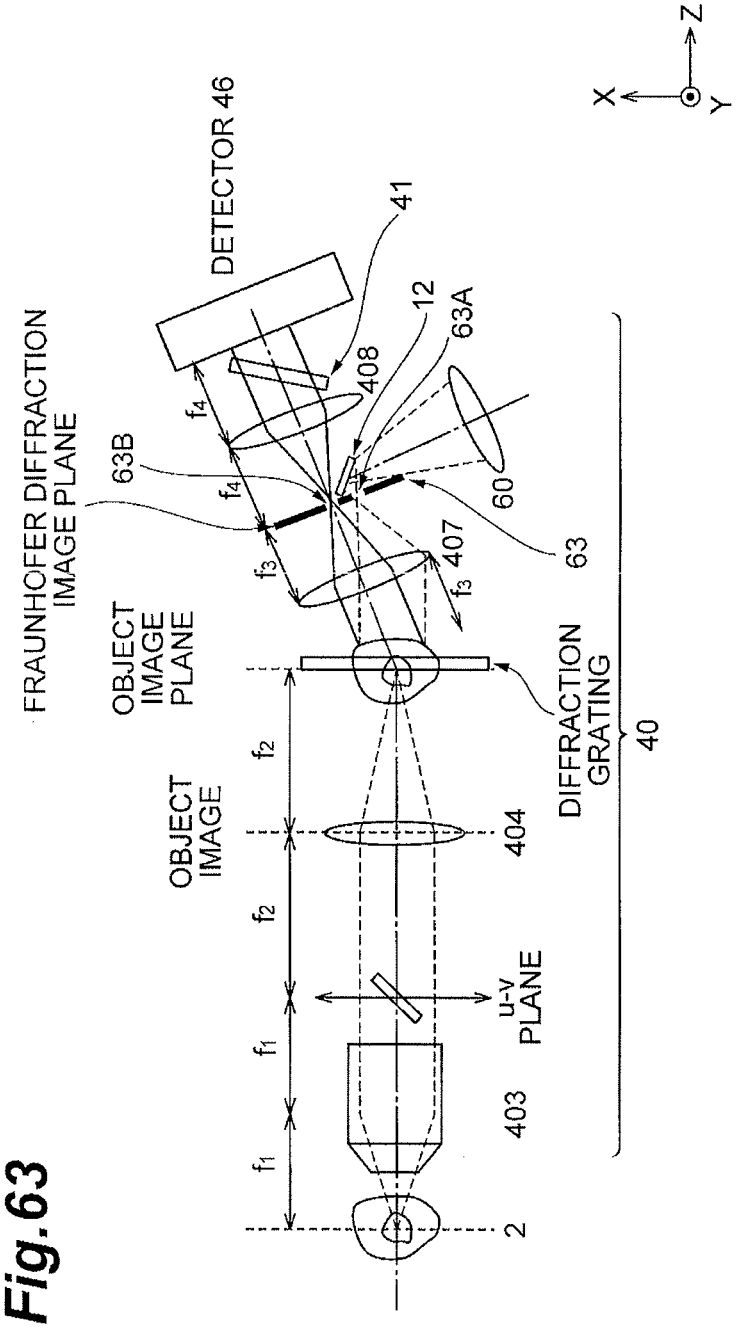
FIG. 63 is a diagram illustrating a lens structure in a twentieth arrangement example.

The twentieth arrangement example uses the diffraction grating described in Literature 2 (Gabriel Popescu, "Diffraction phase microscopy for quantifying cell structure and dynamics," Optics letters, 31, 775, (2006)) as a method for extracting the substantially zero-order light. FIG. 63 illustrates a specific optical system therefor.

As illustrated in FIG. 63, the lens 40 is arranged between the object 2 and the light-receiving surface of the photodetector 46. The lens 40 temporarily forms a Fraunhofer diffraction image subsequent to the object image between the object 2 and the light-receiving surface of the photodetector 46. The lens 40 in the twentieth arrangement example is constituted by the lens 40 in the second arrangement example and lenses 407, 408 for relaying the object image formed by the lens 40. The lenses 407, 408 construct a 4f optical system. The lens 40 in the twentieth arrangement example is constituted by four spherical lenses.

Constructing the lens 40 as mentioned above forms an object image of the object 2 between the lenses 404, 407, and a Fraunhofer diffraction image of the object 2 between the lenses 407, 408. The planes where the object image and Fraunhofer diffraction image are formed will be referred to as object image plane and Fraunhofer diffraction image plane, respectively.

A diffraction grating and the beam splitter 12 are arranged on the object image plane and Fraunhofer diffraction image plane, respectively. The diffraction grating forms a plurality of Fraunhofer diffraction images on the Fraunhofer diffraction image plane. Among them, the zero-order and +first-order diffraction images will be referred to as the zero-order diffraction image and first-order diffraction image, respectively. The direction of grooves of the diffraction grating coincides with the X direction. Therefore, the zero-order and +first-order diffraction images are arranged like a line perpendicular to the Y direction by the diffraction grating.

A pinhole 63 comprises two holes formed so as to cover therein the substantially zero-order light in the zero-order diffraction image and the first-order diffraction image, which are produced by the diffraction grating, respectively. In the zero-order diffraction image, the light transmitted through the hole (pinhole 63A) opened so as to cover the substantially zero-order light therein becomes the second light, which is fed to the first modulator through the beam splitter 12 and lens 60. The light transmitted through the hole (pinhole 63A) opened so as to cover the substantially zero-order light therein becomes the second light, which is fed to the first modulator by way of the beam splitter 12 and lens 60. The light transmitted through the hole (pinhole 63B) opened so as to cover the first-order diffraction image therein becomes the first light, which is fed to the lens 408. That is, the diffraction grating and pinholes 63A, 63B, which separate the first light and second light from each other, act like the beam splitter 12 in the first to nineteenth arrangement examples.

The beam splitter 12 in the twentieth arrangement example may be a mirror which reflects light without transmitting it therethrough. The beam splitter 12 feeds the lens 60 with the light transmitted through the hole (pinhole 63A) opened so as to cover the substantially zero-order light in the pinhole 63. The front focal plane of the lens 60 is on the same plane as the pinhole 63, while the front focal point of the lens 60 coincides with the center of the pinhole 63A. The foregoing structure can extract the substantially zero-order light as the reference light in the twentieth arrangement example as in the first to nineteenth arrangement examples.

When the speed of the object 2 changes, a frequency modulation occurs in the Doppler signal, whereby the finally obtained image of the object 2 elongates or shorten in the flow direction in the observation device 1 of this embodiment. Preferably, for correcting such elongation or shortening, the observation device 1 of this embodiment further comprises a speed detector for detecting the moving speed of the object 2. Preferably, the arithmetic unit 50 performs a correction for the change in speed of the object 2 according to the speed of the object 2 detected by the speed detector when a one-dimensional or two-dimensional Fourier transform with respect to a time variable. The sampling interval of the signals issued from the photodetector 46 may be based on the speed of the object 2 detected by the speed detector.

The speed detector, for which a given one is usable, can also determine the moving speed of the object 2 by detecting the frequency of the signal at the position where the scattered light reaches the back focal plane of the lens 40 according to the relationship between the moving speed and the Doppler shift frequency. In this case, the speed detector may detect a split part of the light directed from the beam splitter 41 to the photodetector 46 on the Fourier plane or include a pixel independently provided in a part of the light-receiving surface of the photodetector 46. Preferably, the pixel has such an area as to exhibit a resolution of the moving speed derived from the relationship between the moving speed V of the object 2 and the Doppler frequency $f_d$.

In the first arrangement example in the observation device 1 of this embodiment, the light (zero-order light) not scattered by the object 2 in the light $L_0$ irradiating the object 2 is converged at one point by the lens 40. For preventing such zero-order light from wholly reaching the light-receiving surface of the photodetector 46, the neutral density filter 45 for attenuating the zero-order light is preferably provided. It is also preferred for the object 2 to be irradiated with the light $L_0$ having such a beam cross section that the zero-order light occurs less. Preferably, the optical intensity reaching the photodetector 46 when no object 2 exists between the light source 10 and the photodetector 46 is taken into account into correcting the intensity distribution $A_0$.

The foregoing explains a case where the object 2 moves in one direction on the $\xi\eta$ plane. The present invention is also applicable to a case where the object 2 moves back and forth in the $\zeta$ direction (direction of the optical axis of the lens 40) perpendicular to the $\xi\eta$ plane. In this case, a Doppler shift occurs radially on the back focal plane of the lens, whereby a photodetector having a circular pixel array structure in which each pixel extends radially is used.

Though the foregoing explanation mainly represents examples in which the phase image of the object is acquired by transmitted illumination, it can also be acquired by reflected illumination as a matter of course. While light in the single longitudinal mode is preferably utilized as the light source for detecting the Doppler shift frequency with high sensitivity, it is not restrictive. For example, using broadband light can also acquire information concerning the depth of phase objects. For measuring the Doppler shift frequency of each wavelength component, light having a fixed phase relationship between wavelength components is preferably used as the wideband light. As such a light source, a mode-locked laser can be used, for example. The mode-locked laser has discrete wavelength components and thus is a very effective light source for detecting the Doppler shift frequency.

Industrial Applicability

Recently, using the term "label-free" as a keyword, attention has been directed to a technique for visualizing cells as the object 2 without staining, so as to discriminate them and so forth. This technique is applied to the observation and diagnosis of cells (cytodiagnosis) for the purpose of retaining cells cultured in vitro to an in vivo state, such as regenerative medicine. On the other hand, circulating tumor cells (CTC), which have recently been attracting attention, are contained in normal nucleated blood cells (i.e., leukocytes) at a rate of about one per 10 million, so that tests must be done rapidly in order to enhance their detectability. The present invention is applicable to such a field. The present invention is also applicable to flow cytometry yielding high throughput. The present invention can observe the moving object 2 by using a one-dimensional photodetector as the photodetector 46, so as to improve the frame rate, and let the object 2 such as cells to flow at high speed, thereby increasing the throughput in testing. Cell specimens and tissue specimens attached to glass slides can also be imaged with favorable contrast without staining. Complex amplitude images can also be obtained under reflected light as in metallographic microscopes.

Reference Signs List

1 ... observation device; 2 ... object; 10 ... light source; 11 ... illumination lens; 12 ... beam splitter; 20 ... first modulator; 21 ... first signal generator; 22 ... first amplifier; 30 ... second modulator; 31 ... second signal generator; 32 ... second amplifier; 40 ... lens; 41 ... beam splitter; 42, 43 ... mirror; 44 ... lens; 45 ... neutral density filter; 46 ... photodetector; 50 ... arithmetic unit; 51 ... first Fourier transform device; 52 ... second Fourier transform unit; 53 ... third Fourier transform device; 54 ... fourth Fourier transform device; 55 ... specific region cutting device; 56 ... initial phase correction device; 57 ... quadratic phase dividing device; 58 ... summing device; 59 ... second direction converter; 60 ... quadratic phase correction unit

The invention claimed is:

1. A phase image acquisition device comprising:
a light source configured to emit light to irradiate a moving object;
a first optical system configured to split the emitted light in two behind the object so as to yield first light and second light, and modulate the second light with a modulator;
a second optical system configured to cause a heterodyne interference between the first light and the modulated second light;
a detection unit comprising a light-receiving surface that has pixels arrayed in a first direction and configured to receive light being heterodyne interfered on the light-receiving surface, and output data representing a sum in a second direction of light having reached each pixel on the light-receiving surface, at each position in the first direction at each time, wherein the first direction is a direction on the light-receiving surface yielding a fixed Doppler shift effect caused by a movement of the object and perpendicular to a moving direction of the object, and the second direction is a direction orthogonal to the first direction and parallel to the moving direction of the object; and
an arithmetic unit comprising a calculator and configured to perform a one-dimensional Fourier transform of data employing the position in the first direction on the light-receiving surface and time as variables with respect to a time variable and a two-dimensional Fourier transform of the Fourier-transformed data, so as to yield data obtained by the two-dimensional Fourier transform as an image of the object.

2. The phase image acquisition device according to claim 1, wherein the arithmetic unit comprises:
a first Fourier transform device configured to perform the one-dimensional Fourier transform with respect to the time variable; and
a second Fourier transform unit configured to perform the two-dimensional Fourier transform; and
wherein the second Fourier transform unit comprises a third Fourier transform device configured to perform a one-dimensional Fourier transform with respect to a frequency and a fourth Fourier transform device configured to perform a one-dimensional Fourier transform with respect to the first direction.

3. The phase image acquisition device according to claim 2, further comprising a lens arranged between the light source and the detection unit;
wherein the light-receiving surface of the detection unit is arranged on a back focal plane in the first direction of the lens, while serving as a back focal plane in the second direction of the lens; and
wherein the light source, lens, detection unit, first Fourier transform device, third Fourier transform device, and fourth Fourier transform device are arranged in sequence.

4. The phase image acquisition device according to claim 2, further comprising a lens arranged between the light source and the detection unit;
wherein the light-receiving surface of the detection unit is arranged on a plane where a Fraunhofer diffraction image of the object is formed by the lens in the first direction, while serving as a plane where a Fraunhofer diffraction image of the object is formed in the second direction; and
wherein the light source, lens, detection unit, first Fourier transform device, third Fourier transform device, and fourth Fourier transform device are arranged in sequence.

5. The phase image acquisition device according to claim 2, further comprising a lens arranged between the light source and the detection unit;
wherein the light-receiving surface of the detection unit is arranged on a plane where a Fraunhofer diffraction image of the object is formed by the lens in the first direction, while serving as a plane where an image of the object is formed in the second direction; and
wherein the light source, lens, detection unit, first Fourier transform device, third Fourier transform device, and fourth Fourier transform device are arranged in sequence.

6. The phase image acquisition device according to claim 2, further comprising a lens arranged between the light source and the detection unit;
wherein the light-receiving surface of the detection unit is arranged on a plane where a Fraunhofer diffraction image of the object is formed by the lens in the first direction, while serving as a plane where a Fresnel diffraction image of the object is formed in the second direction; and
wherein the light source, lens, detection unit, first Fourier transform device, third Fourier transform device, and fourth Fourier transform device are arranged in sequence.

7. The phase image acquisition device according to claim 2, further comprising a lens arranged between the light source and the detection unit;
wherein the light-receiving surface of the detection unit is arranged on a plane where an image of the object is formed by the lens in the first direction, while serving as a plane where a Fraunhofer diffraction image of the object is formed in the second direction;
wherein the light source, lens, detection unit, first Fourier transform device, fourth Fourier transform device, third Fourier transform device, and fourth Fourier transform device are arranged in sequence; and
wherein the lens performs the one-dimensional Fourier transform with respect to the first direction.

8. The phase image acquisition device according to claim 2, further comprising a lens arranged between the light source and the detection unit;

wherein the light-receiving surface of the detection unit is arranged on a plane where an image of the object is formed by the lens in the first direction, while serving as a plane where an image of the object is formed in the second direction;

wherein the light source, lens, detection unit, first Fourier transform device, fourth Fourier transform device, third Fourier transform device, and fourth Fourier transform device are arranged in sequence; and wherein the lens performs the one-dimensional Fourier transform with respect to the first direction.

9. The phase image acquisition device according to claim 2, further comprising a lens arranged between the light source and the detection unit;

wherein the light-receiving surface of the detection unit is arranged on a plane where an image of the object is formed by the lens in the first direction, while serving as a plane where a Fresnel diffraction image of the object is formed in the second direction;

wherein the light source, lens, detection unit, first Fourier transform device, fourth Fourier transform device, third Fourier transform device, and fourth Fourier transform device are arranged in sequence; and wherein the lens performs the one-dimensional Fourier transform with respect to the first direction.

10. The phase image acquisition device according to claim 2, further comprising a lens arranged between the light source and the detection unit;

wherein the light-receiving surface of the detection unit is arranged on a plane where a Fresnel diffraction image of the object is formed by the lens in the first direction, while serving as a plane where a Fraunhofer diffraction image of the object is formed in the second direction; and wherein the light source, lens, detection unit, first Fourier transform device, third Fourier transform device, fourth Fourier transform device, and fourth Fourier transform device are arranged in sequence.

11. The phase image acquisition device according to claim 2, further comprising a lens arranged between the light source and the detection unit;

wherein the light-receiving surface of the detection unit is arranged on a plane where a Fresnel diffraction image of the object is formed by the lens in the first direction, while serving as a plane where an image of the object is formed in the second direction; and wherein the light source, lens, detection unit, first Fourier transform device, third Fourier transform device, fourth Fourier transform device, and fourth Fourier transform device are arranged in sequence.

12. The phase image acquisition device according to claim 2, further comprising a lens arranged between the light source and the detection unit;

wherein the light-receiving surface of the detection unit is arranged on a plane where a Fresnel diffraction image of the object is formed by the lens in the first direction, while serving as a plane where a Fresnel diffraction image of the object is formed in the second direction; and wherein the light source, lens, detection unit, first Fourier transform device, third Fourier transform device, fourth Fourier transform device, and fourth Fourier transform device are arranged in sequence.

13. The phase image acquisition device according to claim 2, further comprising a lens arranged between the light source and the detection unit;

wherein the light-receiving surface of the detection unit is arranged on a plane where a Fresnel diffraction image of the object is formed by the lens in the first direction, while serving as a plane where a Fresnel diffraction image of the object is formed in the second direction; and wherein the light source, lens, detection unit, first Fourier transform device, fourth Fourier transform device, third Fourier transform device, and fourth Fourier transform device are arranged in sequence.

14. The phase image acquisition device according to claim 1, wherein the arithmetic unit performs the two-dimensional Fourier transform of data in a region including a range of a Nyquist frequency in upper and lower region of a difference frequency between first and second modulation frequencies in the data obtained by the one-dimensional Fourier transform with respect to the time variable.

15. A phase image acquisition device comprising:

a light source configured to emit light to irradiate a moving object;

a first optical system configured to split the emitted light in two behind the object so as to yield first light and second light, and modulate the second light with a modulator;

a second optical system configured to cause a heterodyne interference between the first light and the modulated second light:, a detection unit comprising a light-receiving surface that has pixels arrayed in a first direction and configured to receive light being heterodyne interfered on the light-receiving surface, and output data representing a sum in a second direction of light having reached each pixel on the light-receiving surface, at each position in the first direction at each time, wherein the first direction is a direction on the light-receiving surface yielding a fixed Doppler shift effect caused by a movement of the object and perpendicular to a moving direction of the object, and the second direction is a direction orthogonal to the first direction and parallel to the moving direction of the object;

an arithmetic unit comprising a calculator and configured to perform, for data employing a position in the first direction on the light-receiving surface and time as variables, a one-dimensional Fourier transform with respect to a time variable, a one-dimensional Fourier transform with respect to the frequency, and a one-dimensional Fourier transform with respect to the first direction, so as to yield data obtained by the one-dimensional Fourier transforms as an image of the object.

16. The phase image acquisition device according to claim 15, further comprising a lens arranged between the light source and the detection unit;

wherein the arithmetic unit comprises a first Fourier transform device configured to perform the one-dimensional Fourier transform with respect to the time variable and a third Fourier transform device configured to perform the one-dimensional Fourier transform with respect to a frequency, wherein the light-receiving surface of the detection unit is arranged on a plane where an image of the object is formed by the lens in the first direction, while serving as a plane where an image of the object is formed in the second direction;

wherein the light source, lens, detection unit, first Fourier transform device, and third Fourier transform device are arranged in sequence; and wherein the lens performs the one-dimensional Fourier transform with respect to the first direction.

17. The phase image acquisition device according to claim 15, further comprising a lens arranged between the light source and the detection unit;
  wherein the arithmetic unit comprises a first Fourier transform device configured to perform the one-dimensional Fourier transform with respect to the time variable and a third Fourier transform device configured to perform the one-dimensional Fourier transform with respect to a frequency;
  wherein the light-receiving surface of the detection unit is arranged on a plane where an image of the object is formed by the lens in the first direction, while serving as a plane where a Fraunhofer diffraction image of the object is formed in the second direction;
  wherein the light source, lens, detection unit, first Fourier transform device, and third Fourier transform device are arranged in sequence; and
  wherein the lens performs the one-dimensional Fourier transform with respect to the first direction.

18. The phase image acquisition device according to claim 15, further comprising a lens arranged between the light source and the detection unit;
  wherein the arithmetic unit comprises a first Fourier transform device configured to perform the one-dimensional Fourier transform with respect to the time variable and a third Fourier transform device configured to perform the one-dimensional Fourier transform with respect to a frequency;
  wherein the light-receiving surface of the detection unit is arranged on a plane where an image of the object is formed by the lens in the first direction, while serving as a plane where a Fresnel diffraction image of the object is formed in the second direction; and
  wherein the light source, lens, detection unit, first Fourier transform device, and third Fourier transform device are arranged in sequence; and
  wherein the lens performs the one-dimensional Fourier transform with respect to the first direction.

19. The phase image acquisition device according to claim 15, wherein the arithmetic unit further comprises an initial phase correction device configured to correct an initial phase included in the data obtained by the one-dimensional Fourier transform with respect to the time variable.

20. The phase image acquisition device according to claim 15, wherein the detection unit comprises a plurality of photodetectors; and
  wherein the arithmetic unit further comprises an output summing amplifier configured to yield a sum of outputs from the plurality of photodetectors.

21. The phase image acquisition device according to claim 15, wherein the arithmetic unit further comprises a converter configured to perform a Fourier transform or Fresnel transform with respect to the second direction.

22. The phase image acquisition device according to claim 15, wherein the arithmetic unit performs the one-dimensional Fourier transform with respect to the frequency and the one-dimensional Fourier transform with respect to the first direction of data in a region including a range of a Nyquist frequency in upper and lower region of a difference frequency between first and second modulation frequencies in the data obtained by the one-dimensional Fourier transform with respect to the time variable.

23. The phase image acquisition device according to claim 15, further comprising a speed detector configured to detect a moving speed of the object;
  wherein, during the one-dimensional Fourier transform with respect to the time variable, the arithmetic unit corrects a change in the speed of the object according to the moving speed.

24. The phase image acquisition device according to claim 15, wherein the irradiation of the object with the light is performed in an optical arrangement of transmitted illumination.

25. The phase image acquisition device according to claim 15, wherein the irradiation of the object with the light is performed in an optical arrangement of reflected illumination.

26. The phase image acquisition device according to claim 15, wherein the light source generates light in a single longitudinal mode.

27. The phase image acquisition device according to claim 15, wherein the light source generates wideband light.

28. The phase image acquisition device according to claim 27, wherein the light source generates a mode-locked laser.

* * * * *